(12) United States Patent
Ferber et al.

(10) Patent No.: US 11,963,799 B2
(45) Date of Patent: Apr. 23, 2024

(54) SYSTEMS AND METHODS FOR NON-INVASIVE BLOOD PRESSURE MEASUREMENT

(71) Applicant: ITAMAR MEDICAL SPRY 2021, LIMITED PARTNERSHIP, Caesarea (IL)

(72) Inventors: Elad Ferber, Mountain View, CA (US); Pierre-Jean Cobut, Menlo Park, CA (US); Ramkrishnan Narayanan, San Jose, CA (US); Derya Gol Gungor, Sunnyvale, CA (US)

(73) Assignee: ITAMAR MEDICAL SPRY 2021, LIMITED PARTNERSHIP, Caesarea (IL)

( * ) Notice: Subject to any disclaimer, the term of this patent is extended or adjusted under 35 U.S.C. 154(b) by 0 days.

(21) Appl. No.: 18/151,576

(22) Filed: Jan. 9, 2023

(65) Prior Publication Data
US 2023/0200739 A1    Jun. 29, 2023

Related U.S. Application Data

(63) Continuation of application No. 16/907,041, filed on Jun. 19, 2020, now abandoned, which is a
(Continued)

(51) Int. Cl.
*A61B 5/00* (2006.01)
*A61B 5/0205* (2006.01)
(Continued)

(52) U.S. Cl.
CPC .......... *A61B 5/7221* (2013.01); *A61B 5/0002* (2013.01); *A61B 5/0008* (2013.01);
(Continued)

(58) Field of Classification Search
CPC ... A61B 5/0002; A61B 5/7221; A61B 5/0008; A61B 5/0064; A61B 5/0205;
(Continued)

(56) References Cited

U.S. PATENT DOCUMENTS

| | | |
|---|---|---|
| 5,309,916 A | 5/1994 | Hatschek |
| 6,331,162 B1 | 12/2001 | Mitchell |

(Continued)

FOREIGN PATENT DOCUMENTS

| | | |
|---|---|---|
| EP | 2448475 | 5/2012 |
| EP | 2687154 | 8/2019 |

(Continued)

OTHER PUBLICATIONS

Breiman, Leo, "Random Forests", Machine Learning, 2001, pp. 5-32, vol. 45, No. 1.
(Continued)

*Primary Examiner* — Joel F Brutus
(74) *Attorney, Agent, or Firm* — ITAMAR MEDICAL SPRY 2021, LIMITED PARTNERSHIP

(57) ABSTRACT

Systems and methods for non-invasive blood pressure measurement are disclosed. In some embodiments, a system comprises a wearable member configured to generate first and second signals, and a blood pressure calculation system. The blood pressure calculation system a pre-processing module configured to filter noise from the signals, and a wave selection module configured to identify subsets of waves of the signals, a feature extraction module configured to generate sets of feature vectors form the subsets of waves, and a blood pressure processing module configured to calculate an arterial blood pressure value based on the sets of feature vectors and an empirical blood pressure calculation model, the empirical blood pressure calculation model configured to receive the sets of feature vectors as input
(Continued)

values. The blood pressure calculation system further includes a communication module configured to provide a message including or being based on the arterial blood pressure value.

38 Claims, 31 Drawing Sheets

Related U.S. Application Data continuation of application No. 15/368,504, filed on Dec. 2, 2016, now abandoned.

(60) Provisional application No. 62/262,532, filed on Dec. 3, 2015, provisional application No. 62/262,540, filed on Dec. 3, 2015, provisional application No. 62/262,342, filed on Dec. 2, 2015.

(51) Int. Cl.

| | |
|---|---|
| *A61B 5/021* | (2006.01) |
| *A61B 5/024* | (2006.01) |
| *A61B 5/08* | (2006.01) |
| *A61B 5/117* | (2016.01) |
| *A61B 5/145* | (2006.01) |
| *A61B 5/1455* | (2006.01) |
| *G16H 40/67* | (2018.01) |

(52) U.S. Cl.
CPC .......... *A61B 5/0022* (2013.01); *A61B 5/0064* (2013.01); *A61B 5/0205* (2013.01); *A61B 5/021* (2013.01); *A61B 5/02125* (2013.01); *A61B 5/02141* (2013.01); *A61B 5/024* (2013.01); *A61B 5/02416* (2013.01); *A61B 5/0806* (2013.01); *A61B 5/0816* (2013.01); *A61B 5/117* (2013.01); *A61B 5/14532* (2013.01); *A61B 5/14535* (2013.01); *A61B 5/14539* (2013.01); *A61B 5/14546* (2013.01); *A61B 5/1455* (2013.01); *A61B 5/14551* (2013.01); *A61B 5/4872* (2013.01); *A61B 5/6802* (2013.01); *A61B 5/6816* (2013.01); *A61B 5/6823* (2013.01); *A61B 5/6824* (2013.01); *A61B 5/6829* (2013.01); *A61B 5/7203* (2013.01); *A61B 5/721* (2013.01); *A61B 5/7264* (2013.01); *A61B 5/7267* (2013.01); *A61B 5/7275* (2013.01); *A61B 5/7278* (2013.01); *A61B 5/7435* (2013.01); *G16H 40/67* (2018.01)

(58) Field of Classification Search
CPC ..... A61B 5/021; A61B 5/024; A61B 5/02416; A61B 5/0806; A61B 5/0816
See application file for complete search history.

(56) References Cited

U.S. PATENT DOCUMENTS

| | | | |
|---|---|---|---|
| 8,430,817 B1 | 4/2013 | Al-Ali et al. | |
| 8,478,403 B2 | 7/2013 | Wenzel et al. | |
| 8,554,297 B2 | 10/2013 | Moon et al. | |
| 8,849,610 B2 | 9/2014 | Molettiere et al. | |
| 9,028,405 B2 | 5/2015 | Tran | |
| 9,706,964 B2 | 7/2017 | Ferber et al. | |
| 9,717,436 B2 | 8/2017 | Narayan et al. | |
| 10,226,188 B2 | 3/2019 | Watson et al. | |
| 10,463,283 B2 | 11/2019 | Ferber et al. | |
| 2003/0036685 A1* | 2/2003 | Goodman | G16H 70/20 |
| | | | 600/300 |
| 2004/0138540 A1 | 7/2004 | Baker, Jr. et al. | |
| 2006/0122476 A1 | 6/2006 | Van Slyke | |
| 2006/0211942 A1 | 9/2006 | Hoctor et al. | |
| 2007/0055163 A1* | 3/2007 | Asada | A61B 5/6838 |
| | | | 600/490 |
| 2008/0039731 A1 | 2/2008 | McCombie et al. | |
| 2009/0326349 A1 | 12/2009 | McGonigle et al. | |
| 2010/0324384 A1 | 12/2010 | Moon et al. | |
| 2011/0257489 A1 | 10/2011 | Banet et al. | |
| 2012/0029363 A1 | 2/2012 | Lund | |
| 2012/0136261 A1 | 5/2012 | Sethi et al. | |
| 2012/0179011 A1 | 7/2012 | Moon et al. | |
| 2012/0215275 A1 | 8/2012 | Wenzel et al. | |
| 2013/0079657 A1 | 3/2013 | Ochs et al. | |
| 2013/0197322 A1 | 8/2013 | Tran | |
| 2014/0031652 A1 | 1/2014 | Baker, Jr. | |
| 2014/0143064 A1 | 5/2014 | Tran | |
| 2014/0164611 A1 | 6/2014 | Molettiere et al. | |
| 2014/0201126 A1 | 7/2014 | Zadeh et al. | |
| 2014/0243633 A1 | 8/2014 | Addison et al. | |
| 2014/0316226 A1 | 10/2014 | Ferber et al. | |
| 2015/0057554 A1 | 2/2015 | Watson et al. | |
| 2015/0065889 A1 | 3/2015 | Gandelman et al. | |
| 2015/0351699 A1 | 12/2015 | Addison et al. | |
| 2016/0029898 A1 | 2/2016 | Leboeuf et al. | |
| 2016/0135704 A1 | 5/2016 | Zhang | |
| 2016/0242700 A1 | 8/2016 | Ferber et al. | |
| 2016/0270708 A1 | 9/2016 | Tateda et al. | |
| 2016/0287110 A1 | 10/2016 | Morris et al. | |

FOREIGN PATENT DOCUMENTS

| | | |
|---|---|---|
| WO | 2015107268 | 7/2015 |
| WO | 2015116891 | 8/2015 |

OTHER PUBLICATIONS

European Patent Application No. 16756390.7 Search Report dated Sep. 12, 2018.
European Patent Application No. 16756390.7, Examination Report dated Jun. 11, 2019.
Fuke, Sawa et al., "Blood Pressure Estimation from Pulse Wave Velocity Measured on the Chest", 35th Annual International Conference of the IEEE Engineering in Medicine and Biology Society (EMBC), Oct. 2013, pp. 6107-6110.
International Application No. PCT/US2016/019636, International Search Report and Written Opinion dated May 11, 2016.
Kurylak, Yuriy et al., "A Neural Network-based Method for Continuous Blood Pressure Emulation from a PPG Signal", 2013 IEEE International Instrumentation and Measurement Technology Conference (I2MTC), May 2013, pp. 280-283.
Martin-Martinez, Diego et al., "Stochastic Modeling of the PPG Signal: A Synthesis-by-Analysis Approach With Applications", IEEE Transactions on Biomedical Engineering, Apr. 2013, pp. 2432-2441, vol. 60, No. 9.
Monte-Moreno, Enric, "Non-Invasive Estimate of Blood Glucose and Blood Pressure from a Photoplethysmograph by Means of Machine Learning Techniques", Artificial Intelligence in Medicine, Oct. 2011, pp. 127-138, vol. 53, No. 2.
Tamura, Toshiyo et al., "Wearable Photoplethysmographhic Sensors—Past and Present", Electronics, Apr. 2014, pp. 282-302, vol. 3, No. 2.
Wikipedia Foundation, Inc., "Continuous Noninvasive Arterial Pressure", Wikipedia Online Encyclopedia Entry located at https://en.wikipedia.org/wiki/Continuous_noninvasive_arterial_pressure, Aug. 8, 2015.
Deshmane, Anagha Vishwas, "False Arrhythmia Alarm Suppression Using ECG, ABP, and Photoplethysmogram," Master's Thesis, Massachusetts Institute of Technology, Sep. 2009.
Silva, Ikaro et al., "Signal Quality Estimation with Multichannel Adaptive Filtering in Intensive Care Settings," IEEE Transactions in Biomedical Engineering, vol. 59, No. 9, pp. 2476-2485, Sep. 2012.
European Patent Application No. 16871673.6, Search Report dated Jun. 3, 2019.
European Patent Application No. 16871674.4, Search Report dated Jun. 3, 2019.

(56) References Cited

OTHER PUBLICATIONS

European Patent Application No. 16871678.5, Search Report dated Jun. 3, 2019.
International Application No. PCT/US2016/064838, International Search Report and Written Opinion dated Mar. 29, 2017.
International Application No. PCT/US2016/064843, International Search Report and Written Opinion dated Apr. 3, 2017.
International Application No. PCT/US2016/064848, International Search Report and Written Opinion dated Mar. 27, 2017.

* cited by examiner

[2   0.5640  0.2540  0.5025  0.1999  0.4672  0.1777  0.4278  0.1599  0.3389  0.1439  0.2692  0.1286
0.2286  0.1135  0.1836  0.0975  0.1226  0.0794  0.8057  0.5109  0.3123  1.7755  -0.0038  0.7883  0.3677
2.4038  -0.0820  -0.1100  -0.8483  0.0966  -0.2134  -0.3745  0.2508 ]

SYSTEMS AND METHODS FOR NON-INVASIVE BLOOD PRESSURE MEASUREMENT

CROSS-REFERENCE TO RELATED APPLICATIONS

The present application is a continuation of U.S. Nonprovisional patent application Ser. No. 16/907,041, filed Jun. 19, 2020, entitled "SYSTEMS AND METHODS FOR NON-INVASIVE BLOOD PRESSURE MEASUREMENT", which is a continuation of U.S. Nonprovisional patent application Ser. No. 15/368,504, filed Dec. 2, 2016, entitled "SYSTEMS AND METHODS FOR NON-INVASIVE BLOOD PRESSURE MEASUREMENT", which claims the benefit of U.S. Provisional Patent Application No. 62/262,540, filed Dec. 3, 2015, entitled "PREDICTION OF BLOOD PRESSURE FROM PPG DATA," U.S. Provisional Patent Application No. 62/262,532, filed Dec. 3, 2015, entitled "VALIDITY AND CLASSIFICATION FOR BIOLOGICAL SIGNAL RECOGNITION," and U.S. Provisional Patent Application No. 62/262,342, filed Dec. 2, 2015, entitled "RESPIRATORY RAIL ESTIMATION USING OCR MULTISPECTRAL DATA," which are incorporated herein by reference.

BACKGROUND

Technical Field

Embodiments of the present inventions relate generally to blood metrics measurement. More specifically, embodiments of the present inventions relate to non-invasive blood pressure measurement.

Description of Related Art

Wearable activity monitoring devices are growing in popularity. These devices aim to facilitate achieving a user's goal such as to lose weight, to increase physical activity, or simply to improve overall health. Many such devices may interface with computer software to allow visualization of the recorded data. Nevertheless, most devices are evolved cousins of pedometers, which measure the number of steps a user takes. Even though additional functions such as tallying the distance a user travels or calculating calorie consumptions may be added, these devices lack the ability to measure blood metrics.

Blood pressure is an important factor in both heart health and overall health. For example, elevated blood pressure may result in coronary artery disease, heart failure and hypertrophy. Accordingly, blood pressure monitoring has become an important component of patient health. Typically, blood pressure is monitored using a blood pressure gauge with an inflatable cuff. However, such devices are often uncomfortable and unable to provide continuous blood pressure measurement.

SUMMARY

An exemplary system comprises an energy transmitter, an energy receiver, and an analyzer. The energy transmitter may project energy at a first wavelength and a second wavelength into tissue of a user, the first wavelength and the second wavelength being associated with at least one nutrient of a set of nutrients in blood of the user. The energy receiver may generate a composite signal based on a fraction of the energy at the first wavelength and the second wavelength, the fraction of the energy being received through the tissue of the user. The analyzer may separate the composite signal into a first signal corresponding to the first wavelength and a second signal corresponding to the second wavelength, and detect, in the blood of the user, a concentration of the at least one nutrient of the set of nutrients based on the first signal and the second signal.

The fraction of the energy may be received by the energy receiver after the fraction of the energy is reflected by the tissue of the user. The system may comprise a wearable member. The energy transmitter and the energy receiver may be secured to the wearable member such that the energy transmitter and the energy receiver are in contact or in proximity with the tissue. The analyzer may be further configured to determine a set of blood metrics based on the first signal and the second signal, the concentration of at least one nutrient of the set of nutrients being determined based on the determined set of blood metrics. The system may further comprise a user interface configured to display at least some of the set of blood metrics. The analyzer may be further configured to compare a blood metric of the set of blood metric to a threshold and to generate an alert if the blood metric exceeds the threshold. The set of blood metrics may comprise a blood glucose concentration.

The analyzer may be further configured to determine a first AC component and a first DC component of the first signal, to determine a second AC component and a second DC component of the second signal, wherein the concentration of a nutrient of the set of nutrients is detected based on the first AC component, the first DC component, the second AC component, and the second DC component. The system may further comprise a motion detector configured to measure a level of motion, and the analyzer is configured to compare the level of motion to a threshold and to discount a measurement of the composite signal when the level of motion exceeds the threshold. A nutrient of the set of nutrients may comprise glucose.

An exemplary method may comprise projecting energy at a first wavelength and a second wavelength into tissue of a user, the first wavelength and the second wavelength being associated with at least one nutrient of a set of nutrients in blood of the user, generating a composite signal based on a fraction of the energy at the first wavelength and the second wavelength, the fraction of the energy being received through the tissue of the user, separating the composite signal into a first signal corresponding to the first wavelength and a second signal corresponding to the second wavelength, and detecting, in the blood of the user, a concentration of the at least one nutrient of the set of nutrients based on the first signal and the second signal.

Another exemplary system may comprise an energy transmitter, an energy receiver, and an analyzer. The energy transmitter may be configured to project energy at a first wavelength and a second wavelength into tissue of a user, the first wavelength and the second wavelength being associated with, in blood of the user, at least one component. The at least one component being at least one of one of glucose, hemoglobin, triglycerides, cholesterol, bilirubin, protein, albumin, blood pH, Hematocrit, cortisol, and/or electrolytes. The energy receiver may be configured to generate a composite signal based on a fraction of the energy at the first wavelength and the second wavelength, the fraction of the energy being received through the tissue of the user. The analyzer may be configured to separate the composite signal into a first signal corresponding to the first wavelength and a second signal corresponding to the second wavelength, and to detect, in the blood of the user, a concentration of the at least one component based on the first signal and the second signal.

Other features and aspects of various embodiments will become apparent from the following detailed description, taken in conjunction with the accompanying drawings, which illustrate, by way of example, the features of such embodiments.

Typically, blood pressure is measured non-invasively with a sphygmomanometer.

However, such devices are often uncomfortable and do not permit continuous blood pressure measurement. Some embodiments described herein include systems and methods for non-invasive continuous blood pressure measurement. For example, a blood metrics measurement apparatus may generate multi-channel signals (e.g., PPG signals) which may be provided to a blood pressure calculation system to calculate arterial blood pressure values (e.g., systolic blood value pressure and/or diastolic blood pressure value). More specifically, the blood pressure calculation system (or the blood pressure measurement apparatus) may filter the multi-channel signals (e.g., to remove noise from the signals), select (or, "extract") subsets of "high quality" waves from the multi-channel signals, select (or, "extract") sets of features from each of the high quality waves, and generate sets of feature vectors based on the selected sets of features. In some embodiments, an empirical blood pressure model is used to calculate arterial blood pressure values based on the sets of feature vectors.

In various embodiments, a system comprises a wearable member and a blood pressure calculation system. The wearable member may include an energy transmitter configured to project energy at a first wavelength and energy at a second wavelength into tissue of a user, and an energy receiver configured to generate a first signal based on a first received portion of the energy at the first wavelength and a second signal based on a second received portion of the energy at the second wavelength, the first received portion of energy and the second received portion of energy each being received through the tissue of the user. The blood pressure calculation system may include a pre-processing module configured to filter noise (e.g., motion related noise) from the first signal and the second signal, and a wave selection module configured to identify a first subset of waves from a first set of waves of the first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time. The blood pressure calculation system may further include a feature extraction module configured to generate a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one of the measurement values. The blood pressure calculation system may additionally include a blood pressure processing module configured to calculate an arterial blood pressure value based on the first set of feature vectors, the second set of feature vectors, and an empirical blood pressure calculation model, the empirical blood pressure calculation model configured to receive the first set of feature vectors and the second set of feature vectors as input values. The blood pressure calculation system may further include a communication module configured to provide a message including or being based on the arterial blood pressure value.

In some embodiments, the pre-processing module is configured to filter noise from the first signal and second signal using an adaptive filter configured to remove motion noise from the first and second signals.

In some embodiments, the energy transmitter includes a first light source and a second light source, the first light source configured to project the energy at the first wavelength, the second light source configured to project the energy at the second wavelength.

In some embodiments, the first light source and the second light source are spaced at a predetermined distance from each other, and each of the first and second light sources are associated with a different corresponding photodiode energy receiver. In related embodiments, the measurement values comprise a transit time determined based on a time for blood to transit the predetermined distance between the first and second light sources.

In some embodiments, the measurement values include any of wave peak locations or amplitudes, or wave valley locations or amplitudes.

In some embodiments, the measurement values include any of an associated wave's first or higher order derivative peak locations or amplitudes, the associated wave's first or higher order derivative valley locations or amplitudes, or first or higher order moments of the associated wave.

In some embodiments, the metric functions include one or more particular metric functions that calculate a distance between two measurement values.

In some embodiments, the energy projected by the first light source and the energy projected by second light source each have the same wavelength. In related embodiments, the feature extraction module is further configured to determine a phase shift between the first signal and the second signal; calculate, based on the phase shift, any of a pulse wave velocity or a pulse transit time based on the predetermined distance; and the blood pressure calculation module is further configured to calculate the arterial blood pressure value based on first set of feature vectors, the second set of feature vectors, any of the pulse wave velocity or the pulse transit time, the empirical blood pressure calculation model, the empirical blood pressure calculation model further configured to receive the first set of feature vectors, the second set of feature vectors, and any of the pulse wave velocity or the pulse transit time as input.

In some embodiments, the first signal and the second signal each comprise a photoplethysmogram (PPG) signal In various embodiments, a method comprises projecting, at an energy transmitter, energy at a first wavelength and energy at a second wavelength into tissue of a user; generating, at the energy transmitter, a first signal based on a first received portion of the energy at the first wavelength and a second signal based on a second received portion of the energy at the second wavelength, the first received portion of energy and the second received portion of energy each being received through the tissue of the user; filtering, at a blood pressure calculation system, noise from the first signal and second signal; identifying, at the blood pressure calculation system, a first subset of waves from a first set of waves of the first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time; generating, at the blood pressure calculation system, a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one of the measurement values; calculating, at the blood pressure calculation system, an arterial blood pressure value based on the first set of feature vectors, the second set of feature vectors, and an empirical blood pressure calculation model, the empirical blood pressure calculation model configured to receive the first set of feature vectors and the second set of feature vectors as input values; and providing, from the blood pressure calculation system, a message including or being based on the arterial blood pressure value.

In some embodiments, the filtering noise from the first signal and second signal comprises filtering noise from the first signal and second signal using an adaptive filter configured to remove motion noise from the first signal and the second signal.

In some embodiments, the the energy transmitter includes a first light source and a second light source, the first light source configured to project the energy at the first wavelength, the second light source configured to project the energy at the second wavelength. In related embodiments, the first light source and the second light source are spaced at a predetermined distance from each other, and each of the first and second light sources are associated with a different corresponding photodiode energy receiver.

In some embodiments, the measurement values comprise a transit time determined based on a time for blood to transit the predetermined distance between the first and second light sources.

In some embodiments, the measurement values include any of wave peak locations or amplitudes, or wave valley locations or amplitudes.

In some embodiments, the measurement values include any of an associated wave's first or higher order derivative peak locations or amplitudes, the associated wave's first or higher order derivative valley locations or amplitudes, or first or higher order moments of the associated wave.

In some embodiments, the metric functions include one or more particular metric functions that calculate a distance between two measurement values.

In some embodiments, the energy projected by the first light source and the energy projected by second light source each have the same wavelength. In related embodiments, the feature extraction module is further configured to determine a phase shift between the first signal and the second signal; calculate, based on the phase shift, any of a pulse wave velocity or a pulse transit time based on the predetermined distance; and the blood pressure calculation module is further configured to calculate the arterial blood pressure value based on first set of feature vectors, the second set of feature vectors, any of the pulse wave velocity or the pulse transit time, the empirical blood pressure calculation model, the empirical blood pressure calculation model further configured to receive the first set of feature vectors, the second set of feature vectors, and any of the pulse wave velocity or the pulse transit time as input.

In various embodiments, a system comprises a communication interface configured to receive a first signal and a second signal, the first signal being based on a first received portion of energy having been previously projected at a first wavelength into tissue of a user, the second signal being based on a second received portion of energy having been previously projected at a second wavelength into the tissue of the user; a pre-processing module configured to remove noise from the first signal and the second signal; a wave selection module configured to identify a first subset of waves from the first set of waves of a first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time; a feature extraction module configured to generate a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one measurement value; a blood pressure processing module configured to calculate an arterial blood pressure value based on the first set of feature vectors, the second set of feature vectors, and an empirical blood pressure calculation model, the empirical blood pressure calculation model configured to receive the first set of feature vectors and the second set of feature vectors as input values; and a communication module configured to provide a message including or being based on the arterial blood pressure value.

In various embodiments, a system comprises a processor; and memory storing instructions that, when executed by the processor, cause the processor to: receive a first signal and a second signal, the first signal being based on a first received portion of energy having been previously projected at a first wavelength into tissue of a user, the second signal being based on a second received portion of energy having been previously projected at a second wavelength into the tissue of the user; filter noise (e.g., motion related noise) from the first signal and the second signal; identify a first subset of waves from a first set of waves of the first signal and a second subset of waves from a second set of waves of the second signal, each of the first subset of waves representing a separate approximation of an average of the first set of waves over a predetermined amount of time and each of the second subset of waves representing a separate approximation of an average of the second set of waves over the predetermined amount of time; generate a first set of feature vectors and a second set of feature vectors, the first set of feature vectors generated from the first subset of waves, the second set of feature vectors generated from the second subset of waves, wherein each of the feature vectors of the first set of feature vectors and the second set of feature vectors include measurement values and metric values, the measurement values corresponding to amplitude or location points of a particular wave, the metric values generated from metric functions that use at least one of the measurement values; calculate an arterial blood pressure value based on the first set of feature vectors, the second set of feature vectors, and an empirical blood pressure calculation model, the empirical blood pressure calculation model configured to receive the first set of feature vectors and the second set of feature vectors as input values; and provide a message including or being based on the arterial blood pressure value.

DETAILED DESCRIPTION

Biometrics including blood metrics may be measured by minimally invasive procedures to address medical conditions such as diabetes or in the diagnosis and discovery of diseases. Minimal-invasive procedure based devices may have the advantages of reducing costs and decreasing the need for invasive methods, thereby increasing the comfort and well-being of users and patients. Even though these devices have revolutionized patient care, they have only been described in, and approved for, medical purposes. Minimal-invasive procedure based devices are usually out of reach for the general public because they are designed for medical uses rather than non-medical purposes such as fitness, well-being, and quality of life.

Personal devices such as sphygmomanometers or pulse oximeters measure blood pressure or oxygen levels, respectively, on a per-request basis. They usually cannot measure blood metrics real time or periodically. Real-time blood metrics data (e.g., high resolution measurements, or measurements over long periods of time) may allow these devices to facilitate users monitoring and controlling their energy levels and/or metabolism. Nutritionists, people suffering from obesity, people desiring to eat healthier, fitness enthusiasts, semi-professional athletes, people likely to have hypoglycemia, or the vast majority of the general population can benefit from these devices.

In various embodiments, a multispectral blood metric measurement apparatus monitors blood metrics, fitness, and/or metabolism levels of various users in a non-invasive manner. The multispectral blood metric measurement apparatus may be, for example, wearable technology. The multispectral blood metric measurement apparatus may measure any number of blood metrics. Blood metrics may include, for example, various nutrient blood concentrations. Blood metrics may be, for example, monitored, stored, tracked, and/or analyzed.

Figure 1:
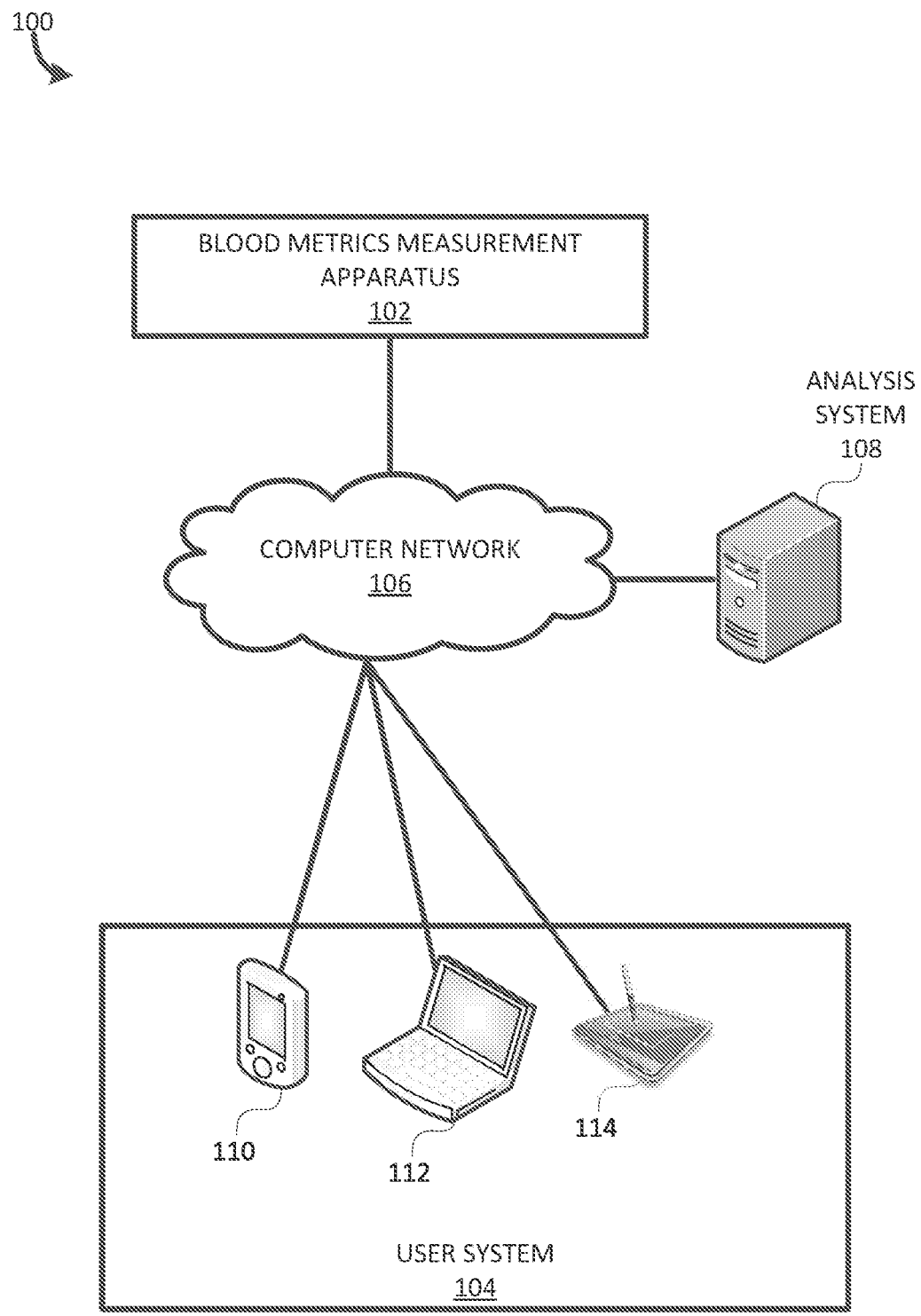
FIG. 1 is a block diagram illustrating an example environment utilizing a multispectral blood metrics measurement apparatus in accordance with various embodiments.

FIG. 1 is a block diagram illustrating an example environment 100 utilizing a multispectral blood metrics measurement apparatus 102 in accordance with various embodiments. As shown in FIG. 1, the example environment 100 may comprise a multispectral blood metrics measurement apparatus 102, one or more user systems 104, an optional analysis system 108, and a computer network 106 communicatively coupling together each of the multispectral blood metrics measurement apparatus 102, one or more user devices 110, 112, and 114 (depicted as user system 104), and/or the analysis system 108. As shown, a user system 104 may include a smartphone 110 (e.g., iPhone®), a computer 112 (e.g., a personal computer), and/or a tablet 114 (e.g., iPad®), through the computer network 106 (e.g., a Bluetooth® 4.0 personal area network), can either interact directly or indirectly with the blood metrics measurement apparatus 102.

The multispectral blood metrics measurement apparatus 102 may measure health or metabolism predictors non-invasively. The multispectral blood metrics measurement apparatus 102 may measure blood metrics such as concentrations of various nutrients over time, deliver energy into tissues of various body parts of a user, track a user's behavior pattern, detect motion, communicate various blood metric measurements, and/or receive a user's instructions. For instance, through the computer network 106, the multispectral blood metrics measurement apparatus 102 may transmit one or more blood metric measurements to, or receive instructions from, the user system 104 or the multispectral blood measurement system 108 such as which health or metabolism predictor to measure.

In some embodiments, the multispectral blood metric 102 measurement apparatus may project energy into tissue of a user and detect energy reflected from and/or transmitted through tissue of the user (e.g., the wearer of the multispectral blood metric measurement apparatus 102). The projected energy may be at multiple wavelengths that are associated with the blood metrics of interest to a user. The detected energy may be a fraction of the energy that is projected into the tissue. Energy at different wavelengths may be absorbed at a different rate that is related to a user's body state. The user's body state (e.g., heart rate, blood pressure, nutrient level, or the like) determines the amount of absorbed energy. Accordingly, energy at different wavelengths may be absorbed at different levels by a user's body. The fraction of energy received (e.g., that is reflected by the tissue or transmitted through the tissue) may be used to generate signals (e.g., composite signals) at different levels. These signals may provide information of the user's body state. This information may be obtained by analyzing waveforms of the signal in the time domain and/or the frequency domain.

In various embodiments, the multispectral blood metric measurement apparatus 102 may measure many metrics, including, but not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, and/or naturally-produced chemical compound level (e.g., lactic acid). Nutrients may be determined based on the blood metrics to be measured. Nutrients may be measured may include, but are not limited to, glucose, hemoglobin, triglycerides, cholesterol, bilirubin, protein, albumin (i.e., egg white), and/or electrolytes (e.g., sodium, potassium, chloride, bicarbonate, etc.)

It will be appreciated that the user's body state may change dynamically and energy at a wavelength may be absorbed differently by a user over the time. By monitoring and tracking detected energy from the user's body, a user's health or condition may be more tracked. Systems and methods described herein may monitor and store blood metrics including concentrations of various nutrients. A user's history health records may be generated by using blood metrics measured at different times. In some embodiments, blood metrics measured a given time point may be compared to the history health records to detect any abnormal health conditions. The multispectral blood metric measurement apparatus may comprise a user interface where a user may input blood metrics of interest, be presented with various health reports, and/or be alerted with abnormal health conditions.

A user may comfortably wear a multispectral blood metric measurement apparatus 102 over time. The multispectral blood metric measurement apparatus 102 may comprise lightweight components. The multispectral blood metric measurement apparatus 102 may be made of hypoallergenic materials. The multispectral blood metric measurement apparatus 102 may be flexibly built so that it could fit various body parts (e.g., wrist, earlobe, ankle, or chest) of a user.

In accordance with some embodiments, the computer network 106 may be implemented or facilitated using one or more local or wide-area communications networks, such as the Internet, WiFi networks, WiMax networks, private networks, public networks, personal area networks ("PAN"), and the like. In some embodiments, the computer network 106 may be a wired network, such as a twisted pair wire system, a coaxial cable system, a fiber optic cable system, an Ethernet cable system, a wired PAN constructed with USB and/or FireWire connections, or other similar communication network. Alternatively, the computer network 106 may be a wireless network, such as a wireless personal area network, a wireless local area network, a cellular network, or other similar communication network. Depending on the embodiment, some or all of the communication connections with the computer network 106 may utilize encryption (e.g., Secure Sockets Layer [SSL]) to secure information being transferred between the various entities shown in the example environment 100.

Although FIG. 1 depicts a computer network 106 supporting communication between different digital devices, it will be appreciated that the multispectral blood metrics measurement apparatus may be directly coupled (e.g., over a cable) with any or all of the user devices 110, 112, and 114.

The user devices 110-114 may include any digital device capable of executing an application related to measuring blood metrics, presenting an application user interface through a display and/or communicating with various entities in the example environment 100 through the computer network 106. For instance, through the computer network 106, the user device 110 may receive one or more blood metric measurements from the multispectral blood metrics measurement apparatus 102, track and store the blood metric measurements, analyze the blood metric measurements, and/or provide recommendations based on the blood metric measurements. An application user interface may facilitate interaction between a user of the user system 104 and an application running on the user system 104.

In various embodiments, any of user devices 110-114 may perform analysis of the measurements from the multispectral blood metrics measurement apparatus 102, display results, provide reports, display progress, display historic readings, track measurements, track analysis, provide alerts, and/or the like.

The analysis system 108 may be any form of digital device capable of executing an analysis application for analyzing and/or measuring blood metrics. In some embodiments, the analysis system 108 may generate reports or generate alerts based on analysis or measurement of blood metrics. For instance, through the computer network 106, the analysis system 108 may receive one or more blood metric measurements from the multispectral blood metrics measurement apparatus 102, track and store blood metric measurements, analyze blood metric measurements, and/or provide recommendations based on the analysis. An application programming interface may facilitate interaction between a user, the user devices 110-114, and/or the multispectral blood metrics measurement apparatus 110 with the analysis system 108.

Computing devices (e.g., digital devices) may include a mobile phone, a tablet computing device, a laptop, a desktop computer, personal digital assistant, a portable gaming unit, a wired gaming unit, a thin client, a set-top box, a portable multi-media player, or any other type of network accessible user device known to those of skill in the art. Further, the analysis system 108 may comprise of one or more servers, which may be operating on or implemented using one or more cloud-based services (e.g., System-as-a-Service [SaaS], Platform-as-a-Service [PaaS], or Infrastructure-as-a-Service [IaaS]).

It will be understood that for some embodiments, the components or the arrangement of components may differ from what is depicted in FIG. 1.

Each of the multispectral blood metrics measurement apparatus 102, one or more user devices 110, 112, and 114, and the analysis system 108 may be implemented using one or more digital devices. An exemplary digital device is described regarding FIG. 8.

Figure 2:
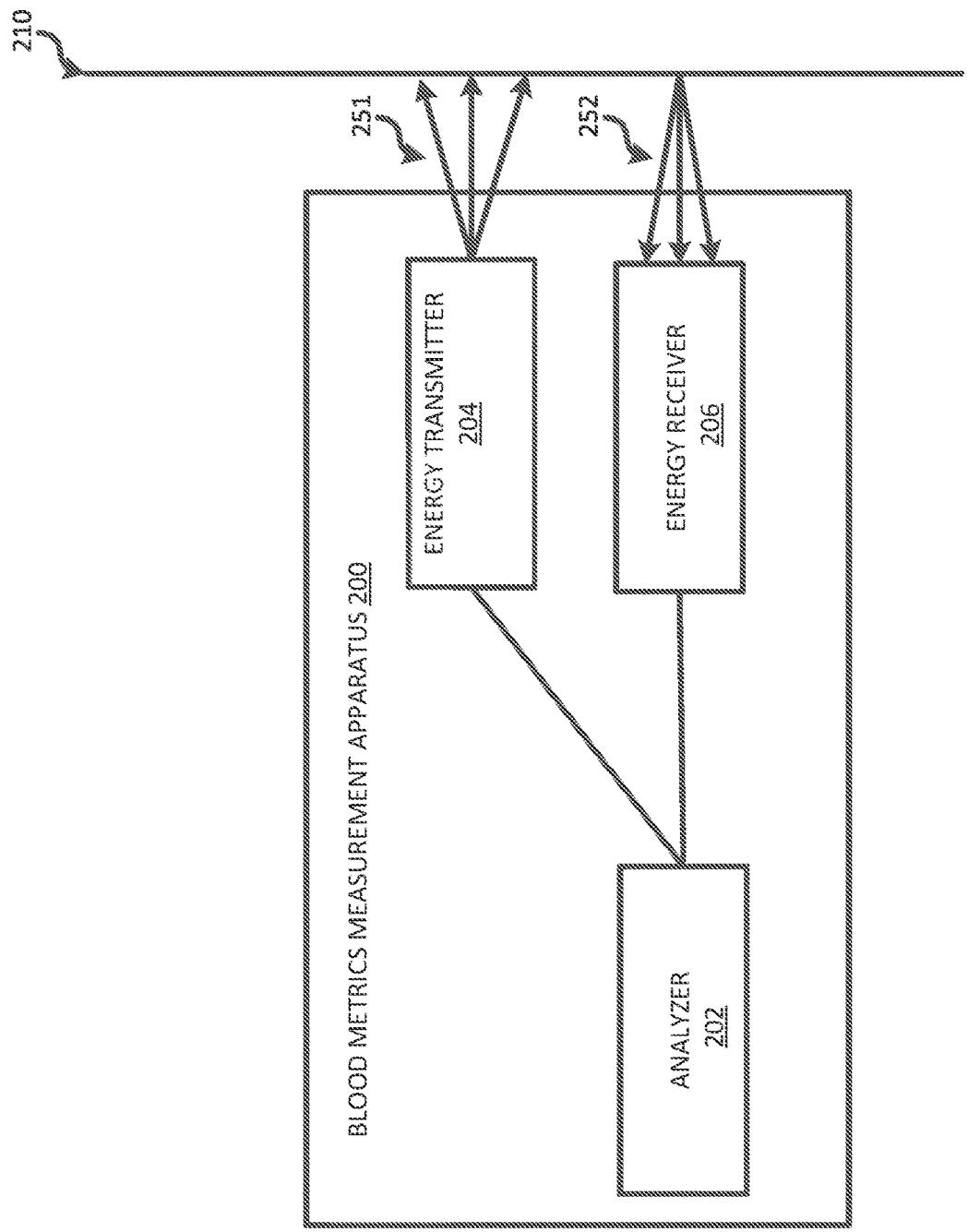
FIG. 2 is a block diagram illustrating an exemplary multispectral blood metrics measurement apparatus, such as the multispectral blood metrics measurement apparatus illustrated in FIG. 1.

FIG. 2 is a block diagram illustrating an exemplary multispectral blood metrics measurement apparatus 200, such as the multispectral blood metrics measurement apparatus 102 illustrated in FIG. 1. The multispectral blood metrics measurement apparatus 200 comprises an analyzer 202, an energy transmitter 204, and an energy receiver 206. Various embodiments may comprise a wearable member. The wearable member may include, for example, a bracelet, glasses, necklace, ring, anklet, belt, broach, jewelry, clothing, or any other member of combination of members that allow the multispectral blood metrics measurement apparatus 200 to be close to or touch a body of the wearer.

The energy transmitter 204 and the energy receiver 206 may be secured to the wearable member such that the energy transmitter and the energy receiver may make contact or be in proximity with tissues (e.g., skin) of a user. The analyzer 202 may be coupled to the energy transmitter 204 and the energy receiver 206. In further embodiments, the multispectral blood metrics measurement apparatus 200 may comprise a communication module (not shown). The communication module may be coupled to the analyzer 202. The blood metrics measurement apparatus 200 may further comprise a driver (not shown) and a power source (not shown). The driver may be coupled to the energy transmitter 204 and the analyzer 202. The analyzer 202 may be coupled to the energy transmitter 204 via the driver. The power source may be coupled to the energy transmitter 204 via the driver. The blood metrics measurement apparatus 200 may further comprise an Analog-to-Digital Converter ("ADC") (not shown). The ADC may be coupled to the energy receiver 206 and the analyzer 202. In some embodiments, the blood metrics measurement apparatus 200 may comprise a motion sensor (e.g., an accelerometer, gyroscope, global positioning system, or the like) (not shown). The motion sensor may be coupled to the analyzer 202.

In various embodiments, the energy transmitter 204 emits energy including, but not limited to, light, into the body of the user. The energy produced by the energy transmitter may be in the direction of entering tissues. For example, the energy produced by the energy transmitter 204 is in a direction 251 entering the tissue 210. In some embodiments, the energy transmitter 204 emits energy or light at different wavelengths. The energy transmitter 204 may comprise any number of light emission diodes ("LEDs"). In some embodiments, the energy transmitter 204 comprises at least two LEDs. Each LED may be configured to emit energy at one or more wavelengths. In another example, each LED may emit light with a peak wavelength centered around a wavelength. In one example, the energy transmitter 204 may emit light with a peak wavelength centered around 500 nm to 1800 nm.

Each wavelength may correspond to one or more blood metrics of interest and/or one or more nutrients. It will be appreciated that different components of the blood and/or different nutrients may absorb energy at different wavelengths. In various embodiments, a controller, driver, analyzer 202, or the like may receive a blood metric or nutrient of interest (e.g., from a user of the multispectral blood metrics measurement apparatus 200 and/or a user device not shown). The controller, driver, analyzer 202 or the like may associate the blood metric and/or nutrient of interest with one or more wavelengths and configure one or more of the LEDs to emit energy of at least one of the one or more wavelengths. For example, the analyzer 202 may command the driver to deliver electric power to one LED that is configured to emit light at the desired wavelength.

The energy receiver 206 may detect energy associated with the energy provided by the LEDs from tissues (e.g., skin) of the user. In this example, received and/or detected energy is in the direction 252 that leaves from the tissue 210. In various embodiments, the energy receiver 206 may detect energy from the body of the user that is a fraction of the energy produced by the energy transmitter 204.

The energy transmitter 204 and the energy receiver 206 may be configured such that the energy receiver 206 detects reflected energy from tissues of the user of the multispectral blood metrics measurement apparatus 200. For example, the energy transmitter 204 and the energy receiver 206 may be configured to be disposed on one surface or side of a user's tissue. The energy transmitter 204 and the energy receiver 206 may be configured such that the energy receiver 206 detects energy from the energy transmitter 204 that passes through or reflects from the user's tissues. In some embodiments, the energy transmitter 204 and the energy receiver 206 may be configured to be disposed on different (e.g., opposite) surfaces or sides of a users' tissue.

Energy detected from tissues of a user may be detected by the energy receiver 206. The energy receiver 206 may be configured to generate a signal in response to the detected energy. In some embodiments, the energy receiver 206 may be triggered by the energy received to generate an output which may be dependent or partially dependent upon the amount of energy received. The energy receiver 206 may be configured to generate a signal (e.g., an electric current, or an electric voltage) in response to the energy received from the tissues.

The signal generated by the energy receiver 206 may be associated with one or more blood metrics and/or nutrients of interest. Energy at different wavelengths may be absorbed at a different rate that is related to a user's body state. The user's body state (e.g., heart rate, blood pressure, nutrient level, or the like) may determine the amount of energy absorbed by the body. Accordingly, energy from the user's body at different wavelengths may be detected at different levels thereby causing different responses of the energy receiver 206. The energy receiver 206 may, for example, output signals based on the level of the energy received.

The energy receiver 206 may provide information associated with the user's body state. Blood metric information may be determined (e.g., by the analyzer 202) from the output signal of the energy receiver 206.

The energy receiver 206 may comprise a set of photodetectors (e.g., a photo diode, or a photo transistor) which are configured to output a signal dependent upon photons or the like from the energy transmitter 204 that passed through tissues of the user.

In various embodiments, the output signal of the energy receiver 206 is a composite of multiple signals. Each signal of the composite may be associated with energy at a wavelength which may be a portion (or fraction) of the total energy emitted by the energy transmitter 204.

The energy transmitter 204 may be configured to generate energy at a set of wavelengths. In some embodiments, the energy transmitter 204 is configured to generate energy such that energy at different wavelengths is generated sequentially and/or periodically. The energy transmitter 204 may be configured to generate energy at each particular wavelength until energy at all wavelengths of the set is generated. The period of time for the energy transmitter 204 to generate energy at all wavelengths is a generation period. Subsequent to completion of the generation period, the energy transmitter 204 may start a new generation period thereby allowing multiple measurements.

In some embodiments, the blood metrics measurement apparatus 200 may be or include the blood metrics measurement apparatus 102 described with regard to FIG. 1.

Figure 3:
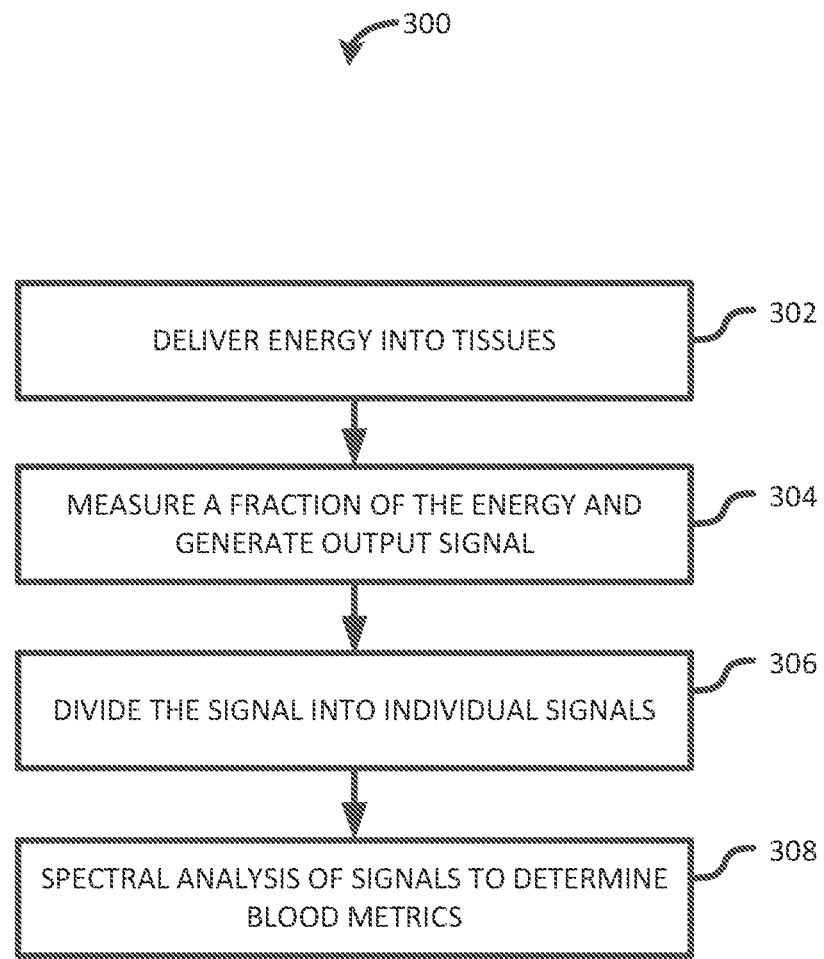
FIG. 3 illustrates an exemplary flow diagram of a method of measuring blood metrics in accordance with an embodiment of the present application.

FIG. 3 illustrates an exemplary flow diagram of a method 300 of measuring blood metrics in accordance with an embodiment of the present application. At step 302, energy transmitter 204 generates and delivers energy at different wavelengths into tissues (e.g., skin) of a user. Different wavelengths may be associated with any number of nutrients, which may be associated with the blood metrics to be measured.

In some embodiments, a user may define various blood metrics and/or nutrients to be measured. Referring back to FIG. 1, a list of blood metrics and/or nutrients may be selected from a user interface (e.g., displayed on an interface of the multispectral blood metrics measurement apparatus 102, on a user device 110-114, or through the analysis system 108). The user may select one or more blood metrics and/or nutrients to be measured.

In some embodiments, a user may define a set of blood metrics to be measured on the user system 104; the multispectral blood metrics measurement apparatus 102 may provide the blood metrics to be measured to the user system 104. For example, on any device of the user system 104, a user may define one or more blood metrics by selecting one or more blood metrics from a list of blood metrics provided, for example, via the user interface.

As discussed herein, the multispectral blood metrics measurement apparatus 200 may measure, but is not limited to, skin conductivity, pulse, oxygen blood levels, blood pressure, blood glucose level, glycemic index, insulin index, Vvo2max, fat body composition, protein body composition, blood nutrient level (e.g., iron), body temperature, blood sodium levels, or naturally-produced chemical compound level (e.g., lactic acid). Nutrients may be determined based on the blood metrics to be measured. The multispectral blood metrics measurement apparatus 200 may measure nutrients, but is not limited to, glucose, hemoglobin, triglycerides, cholesterol, bilirubin, protein, albumin (i.e., egg white), or electrolytes (e.g., sodium, potassium, chloride, bicarbonate, or the like). The multispectral blood metrics measurement apparatus 200 may also measure oxygen, cortisol, and Hematocrit, for example (e.g., blood components).

In various embodiments, one or more wavelengths may be associated with a nutrient or a combination of blood components or molecules. In some embodiments, a number of wavelengths generated by the energy transmitter 204 are the number of blood components or molecules to be measured plus one. For example, when a total number of five (5) blood components and/or molecules are to be measured, a total number of six (6) wavelengths may be determined based on the blood components and/or molecules to be measured. Similarly, it will be appreciated that one or more wavelengths may be associated with a nutrient or a combination of nutrients. In some embodiments, a number of wavelengths generated by the energy transmitter 204 are the number of nutrients to be measured plus one. For example, when a total number of three (3) nutrients are to be measured, a total number of four (4) wavelengths may be determined based on the nutrients to be measured.

In some embodiments, the multispectral blood metrics measurement apparatus 200, user devices 110-114, and/or analysis system 108 may comprise a reference table of blood components, molecules, and/or nutrients and wavelengths corresponding to the blood components, molecules, and/or nutrients. A wavelength may be unique to or more generally associated with a nutrient. A reference wavelength may be unique to or more generally associated with a combination of nutrients to be measured. As such, wavelength(s) may be determined by looking up each blood components, molecules, and/or nutrients that is to be measured. Energy at the determined wavelengths may be transmitted by the energy transmitter 204 into the body.

In various embodiments, in a predetermined time duration, energy at all desired wavelengths may be generated. For each wavelength, the corresponding energy may be generated for a time period equal to a predetermined time duration divided by the number of wavelengths. For example, four (4) wavelengths may be determined and the predetermined time duration is two (2) seconds. Accordingly, energy for each wavelength may be generated for a duration of half (0.5) second.

At step 304, the energy receiver 206 detects a fraction of the energy transmitted into the user's tissue by the energy transmitter 204. The energy receiver 206 may generate a signal based on the fraction of energy detected (e.g., based on the amount of the energy detected). In one example, energy detected at step 304 may be a fraction of the energy generated at step 302 reflected by the tissue. Energy detected at step 302 may be a fraction of the energy generated at step 302 that passes through the tissue (e.g., other undetected energy may be absorbed by tissue and/or otherwise blocked). The output signal of the energy receiver 206 may be an electric current or an electric voltage, of which the amplitude may be related to the amount of the energy detected. In various embodiments, steps 302 and 304 are performed simultaneously. That is, energy generation and detection may be performed approximately simultaneously.

In various embodiments, the output signal generated by the energy receiver 206 is a composite signal of multiple signals, each of which corresponds to one or more wavelengths. The output signal produced at step 306 may be divided into individual signals, each of which is may be associated with one or more wavelengths.

In various embodiments, analysis of the signals from the energy receiver 206 may identify abnormal measurements. For example, each of the measurement may be compared to a predetermined value. If the difference between the measurement and the predetermined value is above (or below) a threshold, then the measurement may be determined to be abnormal. An abnormal value may trigger additional analysis or an alert. In some embodiments, an abnormal value is ignored (e.g., as possibly effected by noise caused by movement of the energy transmitter 204 and/or the energy receiver 206). In various embodiments, the abnormal value may be discounted (e.g., the weight of the value reduced). The degree of discount may be based, for example, on information from an accelerometer (e.g., a large acceleration may indicate that the abnormal value should be significantly discounted) and/or based on historical values. It will be appreciated that the degree of discount may be based on any number of factors.

In some embodiments, measurements may be averaged over a period of time. A Kalman filer (e.g., a nonlinear, unscented Kalman filter) may be applied to any number of measurements or averaged measurements. A motion measurement (e.g., a measurement by an accelerometer) may be considered. Upon determining a measurement is abnormal, the motion measurement for that time point may be inspected. A large measurement may indicate large vibrations or accelerations that corroborate that the measurement may be abnormal. Measurements collected in such situations are likely to have significant electrical noises.

At step 308, the analyzer 202 may analyze signals from the energy receiver 206 analyzed in the frequency domain to determine blood metrics. Concentration of a nutrient in the blood may subsequently be determined. In some embodiments, signals may be provided to a bandpass filter that separates AC components from DC components. An AC component may represent signal variation at the cardiac frequency and a DC component may represent the average overall transmitted light intensity. In some embodiments, a heart rate and/or oxygen saturation, $SpO_2$ may be determined. The heart rate may be determined, for example, by averaging the maximum frequency to determine the rate of cardiac beats in a predetermined amount of time. The oxygen saturation $SpO_2$ may be determined according to Equation (1):

$$S_pO_2 = 110 - 25 \times R \quad (1),$$

where R is the ratio of a red and infrared normalized transmitted light intensity. R may be determined according to Equation (2):

$$R = \frac{AC_R/DC_R}{AC_{IR}/DC_{IR}}, \quad (2),$$

where the $AC_R$ is the AC component of the detected energy corresponding to a wavelength (e.g., red light), $DC_R$ is the DC component of the detected energy corresponding to the wavelength (e.g., red light), $AC_{IR}$ is the AC component of the detected energy corresponding to a different wavelength (e.g., infrared light), and $DC_{IR}$ is the DC component of the detected energy corresponding to the different wavelength (e.g., infrared light). In some embodiments, the AC component may be selected as the highest spectral line in the cardiac frequency band. Waveform analysis may be performed to determine the R-R interval defined by two successive AC components, an elapsed interval and the perturbation, if there is any.

It will be appreciated that analysis may be performed by the analyzer 202 and/or any other digital device (e.g., any of users devices 110-114 or analysis system 108).

At step 308, state space estimation and progression may be performed to determine blood metrics. A system may be modeled according to Equation (3):

$$x(n+1) = f[x(n)] + u(n)$$

$$y(n) = h[x(n)] + v(n) \quad (3),$$

where x(n) represents the state of the system, u(n) is process noise, y(n) is the vector of the observed signals, and v(n) is the measurement noise.

Table 1 lists one or more parameters for x(n) as well as their initial value in some embodiments:

TABLE 1

| Parameter | Symbol | Initial Value |
|---|---|---|
| Cardiac frequency | $f_{HR}$ | 1 Hz |
| Cardiac phase | $\theta_{HR}$ | 0 |
| Cardiac harmonic amplitude | $I_{Harmonic}^{HR}$ | 0 |
| Cardiac Pulse Pressure | $P_{HR}$ | 1 |
| Point Blood Pressure | $P_{Point}$ | 1 |
| Respiratory frequency | $f_{Resp}$ | 0.3 Hz |
| Respiratory phase | $\theta_{Resp}$ | 0 |
| Wavelength i = 1..N AC peak amplitude | $I_{\lambda,i}^{AC}$ | 0.5 max_value |
| Wavelength i = 1..N AC peak location | $pos_{\lambda,i}^{AC}$ | Corresponding FFT bin to 1 Hz |
| Wavelength i = 1..N DC | $I_{\lambda,i}^{DC}$ | 0.5 max_value |
| Wavelength i = 1..N p2p amplitude | $I_{\lambda,i}^{p2p}$ | 1 ADC read |
| Wavelength i = 1..N rise time | $\tau_{\lambda,i}^{rise}$ | 0.1 sec |
| Wavelength i = 1..N Significance coefficient | $c_{\lambda,i}$ | 1 |
| Wavelength i = 1..N HRV | $T_{\lambda,i}^{HRV}$ | 1 sec |
| Best Ratio pH | $BR_{pH}$ | 2 |
| Best Ratio pCO2 | $BR_{pCO2}$ | 3 |
| Best Ratio pHCO3– | $BR_{pHCO3-}$ | 4 |
| Acceleration magnitude | $I_{move}$ | 0 |
| GPS velocity | $|v|_{GPS}$ | 0 |
| GPS altitude | $|alt|_{GPS}$ | 0 |
| GPS acceleration | $|\alpha|_{GPS}$ | 0 |
| GPS incline | $|incline|_{GPS}$ | 0 |
| Restfulness | Rest | 0 |
| Hydration | Hyd | 0 |
| Systolic Blood Pressure | SBP | 120 mmHg |
| Diastolic Blood Pressure | DBP | 80 mmHg |
| End tidal CO2 | ETCO2 | 40 mmHg |
| Blood Carbon Monoxide | SpCO | 0% |

Table 2 lists one or more parameters for y(n) as well as their initial value in some embodiments:

TABLE 2

| Parameter | Symbol | Initial |
|---|---|---|
| Blood pH | pH | 7.35 |
| Blood PCO2 | $pCO_2$ | 24 mmol |
| Blood PO2 | $pO_2$ | 24 mmol |
| Blood PHCO3− | $p\overline{HCO_3}$ | 24 mmol |
| Blood Glucose | $pC_6H_{12}O_6$ | 3 mmol |
| Cardiac Frequency | $f_{HR}$ | 1 |
| Point Blood Pressure | $P_{Point}$ | 1 |
| Respiratory Frequency | $f_{Resp}$ | 0.3 Hz |
| GPS velocity | $|v|_{GPS}$ | 0 |
| GPS altitude | $|alt|_{GPS}$ | 0 |
| GPS acceleration | $|a|_{GPS}$ | 0 |
| GPS incline | $|incline|_{GPS}$ | 0 |

Table 3 lists the state space model F(X(n)) between the parameters listed in Table 1 and Table 2 in some embodiments, where the energy wavelengths comprise 880 nm, 631 nm, 1450 nm, and 1550 nm:

TABLE 3

| Name | Symbol | Equation |
|---|---|---|
| Cardiac frequency | $f_{HR}$ | $\text{bin\_to\_freq}\left(\dfrac{\Sigma c_{\lambda_i} pos_{\lambda_i}^{AC}}{\Sigma c_{\lambda_i}}\right)$ |
| Cardiac phase | $\theta_{HR}$ | $\theta_{HR}(n-1) + f_s^{-1} * \omega^*$, where $\omega^* \in [\omega\_min, \omega\_max]$ |
| Cardiac harmonic amplitude | $I_{HR}^{Harmonic}$ | $\dfrac{\Sigma c_{\lambda_i} I_{\lambda_i}^{p2p}}{\Sigma c_{\lambda_i}}$ |
| Cardiac Pulse Pressure | $P_{HR}$ | $\left(\dfrac{\Sigma c_{\lambda_i} \tau_{\lambda_i}^{rise}}{\Sigma c_{\lambda_i}}\right)^{\wedge} - 1$ |
| Point Blood Pressure | $P_{point}$ | $\tau_{\lambda_1}^{rise^{-1}}$ |
| Respiratory frequency | $f_{Resp}$ | 3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges<br><br>$\omega_r(n + 1) = \overline{\omega}_r + \alpha_r\{s_r[\omega_r(n)] - \overline{\omega}_r\} + u_{\omega_s}(n)$ (15)<br>$\omega_{ca}(n + 1) = \overline{\omega}_c + \alpha_c\{s_c[\omega_{ca}(n)] - \overline{\omega}_c\} + u_{\omega_{ca}}(n)$ (16)<br><br>where $\overline{\omega}_r$ and $\overline{\omega}_c$ are the a priori estimates of the expected respiratory and cardiac frequencies, respectively; $\alpha_r$, and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively. The instantaneous respiratory and heart rates in units of Hz are then<br><br>$f_r(n) = \dfrac{1}{2\pi T_s} s_r[\omega_r(n)]$ (17)<br><br>$f_c(n) = \dfrac{1}{2\pi T_s} s_c[\omega_c(n)].$ (18) |
| Respiratory phase | $\theta_{Resp}$ | $\theta_{Resp}(n-1) + f_s^{-1} * \omega^*$, where $\omega^* \in [\omega\_min, \omega\_max]$ |
| $\lambda = 880$ nm AC peak | $I_{\lambda_i}^{AC}$ | From FFT |
| $\lambda = 880$ nm DC | $pos_{\lambda_i}^{AC}$ | From FFT |
| $\lambda = 880$ nm p2p amplitude | $I_{\lambda_i}^{DC}$ | From Waveform analysis |
| $\lambda = 880$ nm rise time | $I_{\lambda_i}^{p2p}$ | From Waveform analysis |
| $\lambda = 880$ nm signal trend | $\tau_{\lambda_i}^{rise}$ | From Waveform analysis |
| $\lambda = 880$ nm Significance coefficient | $c_{\lambda_i}$ | From Waveform analysis |
| $\lambda = 880$ nm HRV | $T_{\lambda_i}^{HRV}$ | From Waveform analysis |
| $\lambda = 631$ nm AC peak | $I_{\lambda_i}^{AC}$ | From Fast Fourier Transformation ("FFT") |
| $\lambda = 631$ nm | $pos_{\lambda_i}^{AC}$ | From FFT |

TABLE 3-continued

| Name | Symbol | Equation |
|---|---|---|
| DC $\lambda = 631$ nm | $I_{\lambda_i}^{DC}$ | From Waveform analysis |
| p2p amplitude $\lambda = 631$ nm | $I_{\lambda_i}^{p2p}$ | From Waveform analysis |
| rise time $\lambda = 631$ nm | $\tau_{\lambda_i}^{rise}$ | From Waveform analysis |
| signal trend $\lambda = 631$ nm Significance coefficient | $c_{\lambda_i}$ | From Waveform analysis |
| $\lambda = 631$ nm HRV | $T_{\lambda_i}^{HRV}$ | From Waveform analysis |
| $\lambda = 1450$ nm AC peak | $I_{\lambda_i}^{AC}$ | From FFT |
| $\lambda = 1450$ nm AC | $pos_{\lambda_i}^{AC}$ | From FFT |
| DC $\lambda = 1450$ nm | $I_{\lambda_i}^{DC}$ | From Waveform analysis |
| p2p amplitude $\lambda = 1450$ nm | $I_{\lambda_i}^{p2p}$ | From Waveform analysis |
| rise time $\lambda = 1450$ nm | $\tau_{\lambda_i}^{rise}$ | From Waveform analysis |
| signal trend $\lambda = 1450$ nm Significance coefficient | $c_{\lambda_i}$ | From Waveform analysis |
| $\lambda = 1450$ nm HRV | $T_{\lambda_i}^{HRV}$ | From Waveform analysis |
| $\lambda = 1550$ nm AC peak | $I_{\lambda_i}^{AC}$ | From FFT |
| $\lambda = 1550$ nm AC | $pos_{\lambda_i}^{AC}$ | From FFT |
| DC $\lambda = 1550$ nm | $I_{\lambda_i}^{DC}$ | From Waveform analysis |
| p2p amplitude $\lambda = 1550$ nm | $I_{\lambda_i}^{p2p}$ | From Waveform analysis |
| rise time $\lambda = 1550$ nm | $\tau_{\lambda_i}^{rise}$ | From Waveform analysis |
| signal trend $\lambda = 1550$ nm Significance coefficient | $c_{\lambda_i}$ | From Waveform analysis |
| $\lambda = 1550$ nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3- | $BR_{pHCO3^-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

Table 4 lists $Y(n) = H(x(n))$:

TABLE 4

| Name | Symbol | Equation |
|---|---|---|
| Blood pH | pH | $6.1 + \log\left(\dfrac{pHCO_3^-}{0.03 pCO_2}\right)$ |
| Blood PCO2 | $pCO_2$ | $\dfrac{\epsilon_{Hb}^{CO_2} - \epsilon_{Hb}^{Hb} * I_{\lambda_{CO_2}}^{AC} * I_{\lambda_1}^{DC} / \left(I_{\lambda_1}^{AC} * I_{\lambda_{CO_2}}^{DC}\right)}{\epsilon_{Hb}^{CO_2} - \epsilon_{CO_2}^{CO_2} + \left(\epsilon_{CO_2}^{Hb} - \epsilon_{Hb}^{Hb}\right) * I_{\lambda_{CO_2}}^{AC} * I_{\lambda_1}^{DC} / \left(I_{\lambda_1}^{AC} * I_{\lambda_{CO_2}}^{DC}\right)}$ |

TABLE 4-continued

| Name | Symbol | Equation |
|---|---|---|
| Blood PO2 | pO$_2$ | $\dfrac{\epsilon_{Hb}^{O_2} - \epsilon_{Hb}^{Hb} * I_{\lambda_{O_2}}^{AC} * I_{\lambda_1}^{DC} / \left(I_{\lambda_1}^{AC} * I_{\lambda_{O_2}}^{DC}\right)}{\epsilon_{Hb}^{O_2} - \epsilon_{O_2}^{O_2} + \left(\epsilon_{O_2}^{Hb} - \epsilon_{Hb}^{Hb}\right) * I_{\lambda_{O_2}}^{AC} * I_{\lambda_1}^{DC} / \left(I_{\lambda_1}^{AC} * I_{\lambda_{O_2}}^{DC}\right)}$ |
| Blood PHCO3- | pHCO$_3^-$ | $\dfrac{\epsilon_{Hb}^{HCO_3^-} - \epsilon_{Hb}^{Hb} * I_{\lambda_{HCO_3^-}}^{AC} * I_{\lambda_1}^{DC} / \left(I_{\lambda_1}^{AC} * I_{\lambda_{HCO_3^-}}^{DC}\right)}{\epsilon_{Hb}^{HCO_3^-} - \epsilon_{HCO_3^-}^{HCO_3^-} + \left(\epsilon_{HCO_3^-}^{Hb} - \epsilon_{Hb}^{Hb}\right) * I_{\lambda_{HCO_3^-}}^{AC} * I_{\lambda_1}^{DC} / \left(I_{\lambda_1}^{AC} * I_{\lambda_{HCO_3^-}}^{DC}\right)}$ |
| Blood Glucose | pC$_6$H$_{12}$O$_6$ | As above |
| Cardiac Frequency | f$_{HR}$ | As in f(x(n)) |
| Point Blood Pressure | P$_{Point}$ | As in f(x(n)) |
| Respiratory Frequency | f$_{Resp}$ | As in f(x(n)) |
| GPS velocity | lvl$_{GPS}$ | As in f(x(n)) |
| GPS altitude | laltl$_{GPS}$ | As in f(x(n)) |
| GPS acceleration | lal$_{GPS}$ | As in f(x(n)) |
| GPS incline | linclinel$_{GPS}$ | As in f(x(n)) |

As illustrated in Tables 3 and 4, by generating energy at different wavelengths, one or more blood metrics may be determined from the detected energy. For example, cardiac frequency, cardiac phase, cardiac harmonic amplitude, cardiac pulse pressure, point blood pressure, respiratory frequency, respiratory phase, blood pH, blood pCO$_2$, blood pHCO$_{3-}$, or blood glucose, may be determined.

Figure 4:
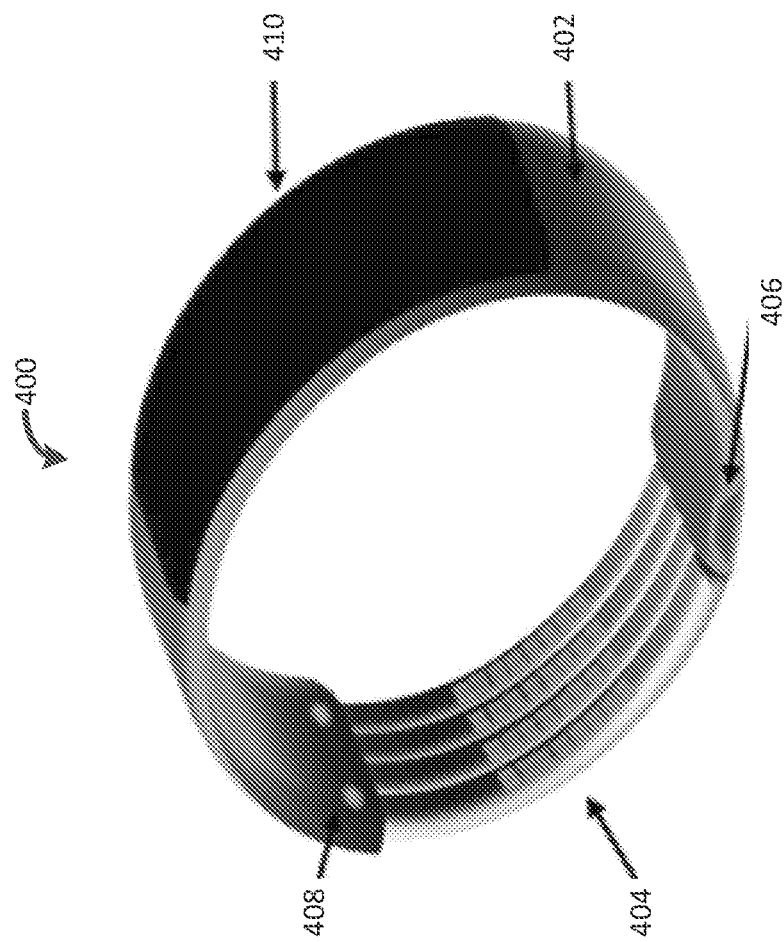
FIG. 4 illustrates an exemplary apparatus for measuring various blood metrics in accordance with an embodiment of the present application.

FIG. 4 illustrates an exemplary apparatus 400 for measuring various blood metrics in accordance with an embodiment of the present application. The apparatus 400 comprises a central unit 402, a sensor array 404, and a coupling means 408. The central unit 402 may be a wearable member made of elastic and/or flexible hypoallergenic wearable material.

In the illustrated example, the sensor array 404 is coupled to the central unit 402. The sensor array 404 may comprise any number of energy transmitters and/or energy receivers. The sensor array 404 may be detached from the central unit 402. In some embodiments, the sensor array 404 may be mechanically and electrically coupled to the central unit 402. The sensor array 404 comprises various illumination (e.g., near infra-red, infra-red, or short infra-red) and sensing array. The sensor array 404 may further comprise conductivity and/or capacity sensors. Different sensor array 404 may be provided to measure different blood metrics.

The central unit 402 may comprise an analyzer. In some embodiments, the central unit comprises an analyzer, one or more energy transmitter(s), and one or more energy receiver (s). The central unit 402 may further comprise a communication module and/or a battery compartment. The coupling means 408 are mounting screw holes in FIG. 4, however, it will be appreciated that coupling means may be optional. Further, coupling means 408 may include any kind of means including a clip, hook, switch, expanding fabric, adhesive, or the like. One of ordinary skill in the art would understand that other mounting means may be used.

The apparatus 400 further comprises a micro-USB port 406 to allow for communication with a digital device and a screen 410. Various user interfaces (e.g., lights, a display, touchscreen, or the like) may be displayed on the screen 410.

In some embodiments, the apparatus 400 may be or include the blood metrics measurement apparatus 200 described with regard to FIG. 2, or the blood metrics measurement apparatus 102 described with regard to FIG. 1.

Figure 5:
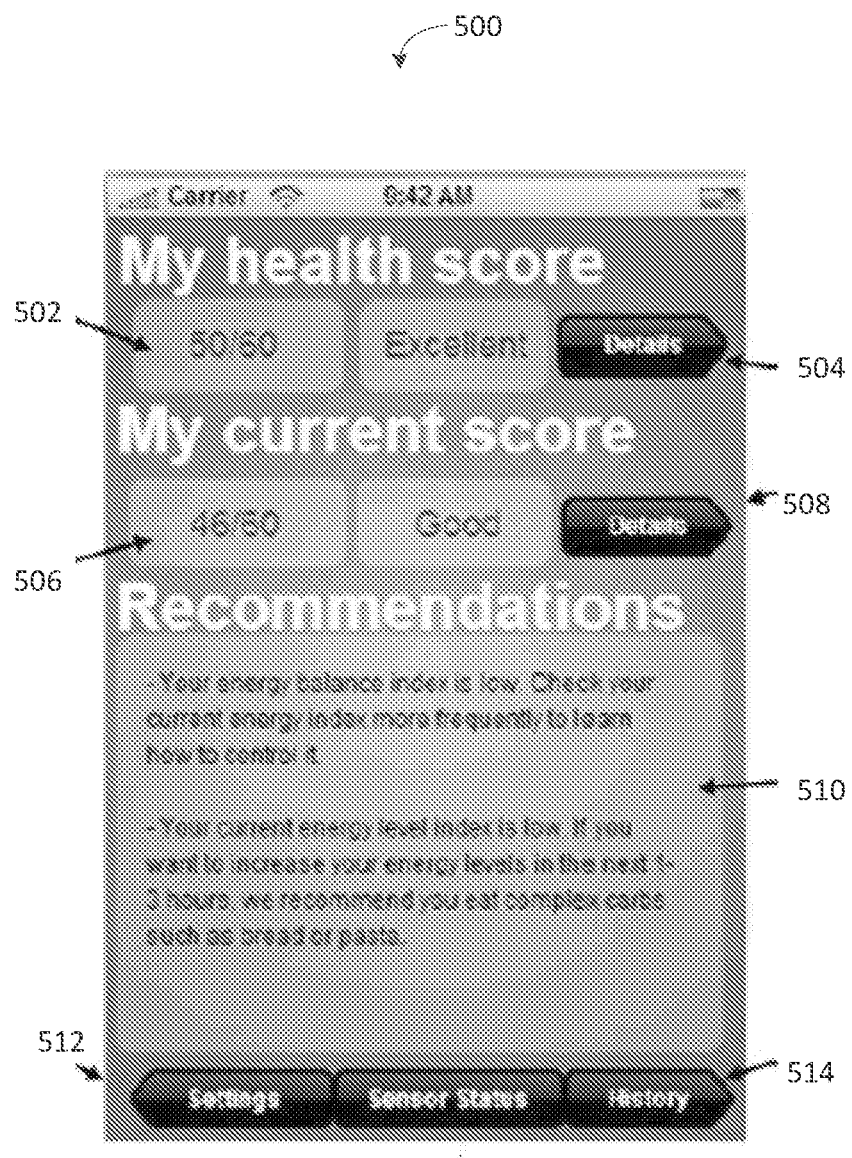
FIG. 5 illustrates a display of an assessment of a current health index derived from data collected from or with a multispectral blood metrics measurement apparatus in various embodiments.
Figure 6:
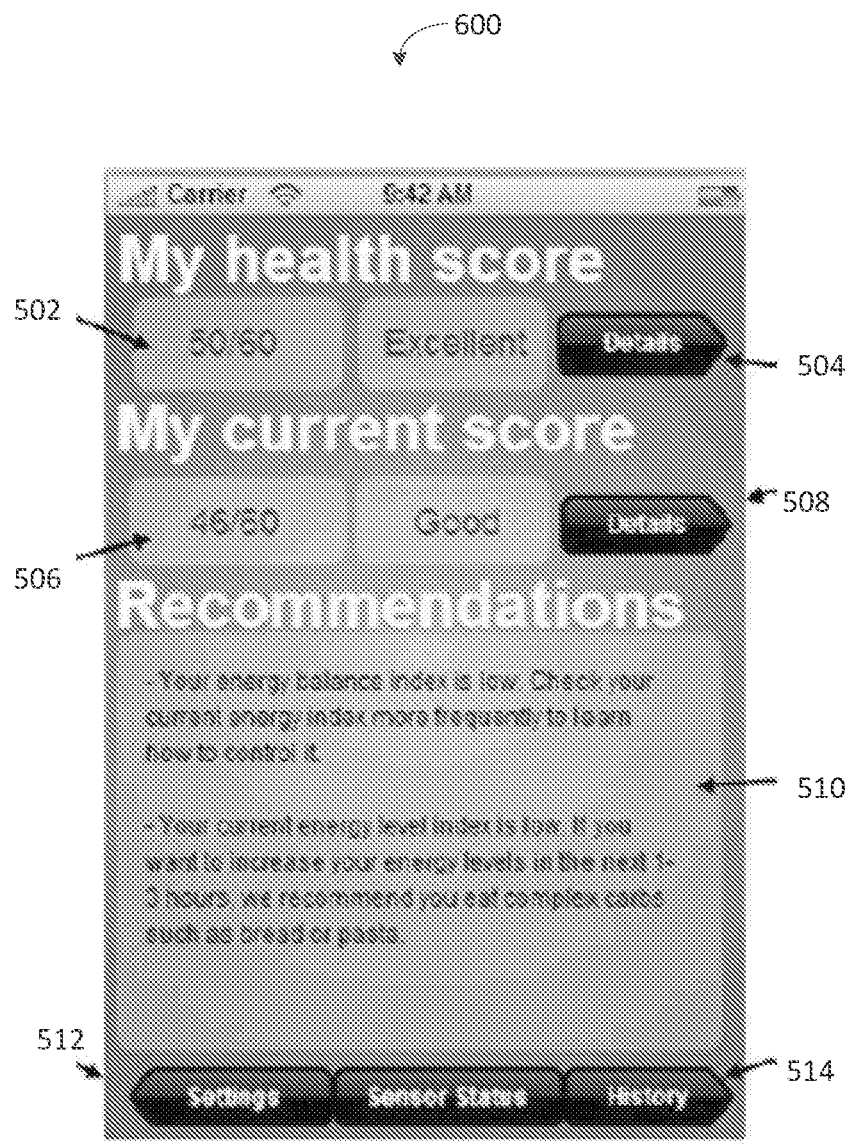
FIG. 6 illustrates a display of an assessment of an overall health index, derived from data collected from or with a multispectral blood metrics measurement apparatus in various embodiments.
Figure 7:
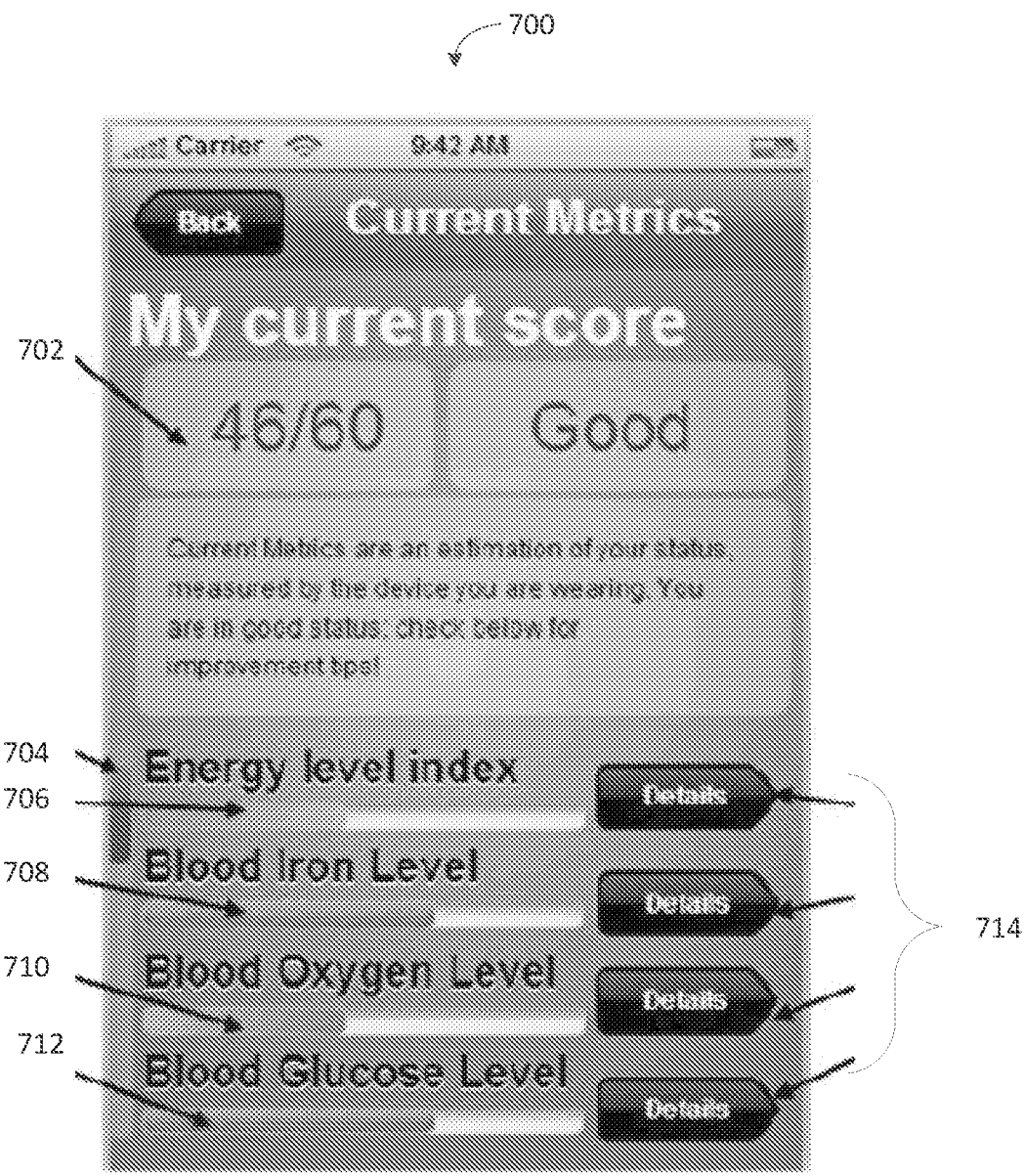
FIG. 7 illustrates a display of an assessment of an overall health index, derived from data collected from or with a multispectral blood metrics measurement apparatus in various embodiments.

FIGS. 5-7 are screenshots illustrating an example of presenting health analysis over a user interface in accordance with various embodiments. Various embodiments may store blood metrics and/or nutrient measurements. FIG. 5 illustrates a display 500 of an assessment of a current health index derived from data collected from or with a multispectral blood metrics measurement apparatus in various embodiments. The display may appear on the user's smartphone, for example. In various embodiments, the analyzer 202 or any digital device may analyze measurements collected over time to generate a health score that can be compared to a health threshold to provide qualitative and/or quantitative scoring. Similarly, the analyzer 202 or any digital device may analyze measurements recently collected to generate a current score that can be compared to a current health threshold to provide qualitative and/or quantitative scoring.

In some embodiments, a user interface may display a health score 502, an option for details regarding the health score 504, a current score 506, an option for details regarding the current score 508, a recommendation 510, a settings option 512, and a history of measurements 514. Options for details 504 and 506 may describe the metrics as well as the values of the metrics that went into the health score 504 and the current score 506, respectively.

In some embodiments, there is a recommendation engine configured to retrieve recommendations 510 based on the health score 504 and/or the current score 506. The settings option 512 may allow the user to configure metrics to be tracked and set alerts. In some embodiments, the user may utilize the settings options 512 to secure the information (e.g., encrypt the information and/or set passwords). The history of measurements option 514 may provide logged metrics and analysis information over time (e.g., as a chart).

It will be appreciated that the multispectral blood metrics measurement apparatus 200 and/or any digital device may generate reports based on the analysis, the metrics (e.g., blood metrics or metrics based on nutrients), historic measurements, historic analysis, or any other information. Further, alerts may be set by the multispectral blood metrics measurement apparatus 200 and/or any digital device.

It will also be appreciated that the multispectral blood metrics measurement apparatus 200 may be taking many measurements over time (e.g., many measurements every minute) and may track health and changes in metrics over time and/or in the short term. In some embodiments, if a condition is of sufficient seriousness (e.g., heart rate shows erratic beats), the multispectral blood metrics measurement apparatus 200 or any digital device may provide an alert and request assistance (e.g., from emergency personnel via the communication network).

Various health and wellness predictors such as, but not limited to, energy level, blood iron level, blood oxygen level, and blood glucose level are displayed. FIG. 6 illustrates a display 600 of an assessment of an overall health index, derived from data collected from or with a multispectral blood metrics measurement apparatus in various embodiments.

In some embodiments, a user interface may display a current score 602, energy balance information 606, sleep quality information 608, blood metrics information 610, and body composition information 612 as well as other information accessible by slider 604. Additional details may be available through buttons 614. It will be appreciated that any amount of information may be provided. In some embodiments, the display 600 summarizes information while more detailed information recommendations, measurement data, analysis information, and the like may be available through the details buttons 614 or in other screens.

Recommendations to the user based on the current and previous measurements are provided. FIG. 7 illustrates a display 700 of an assessment of an overall health index, derived from data collected from or with a multispectral blood metrics measurement apparatus in various embodiments. In some embodiments, a user interface may display a current score 702, energy level information 706, blood iron level information 708, blood oxygen level information 710, and blood glucose level 712 as well as other information accessible by slider 704. Additional details may be available through buttons 714. It will be appreciated that any amount of information may be provided. In some embodiments, the display 700 summarizes information while more detailed information recommendations, measurement data, analysis information, and the like may be available through the details buttons 714 or in other screens.

Various embodiments track and analyze blood metrics. Health recommendations may be based on instantaneous blood metrics measurements and history blood metrics measurement. In addition, blood metrics and health condition of a user may be compared to health data of the general public. For example, a user's health condition may be compared to health condition of other similar users such as users of the same gender and age group, users of the same profession, friends of a user, etc.

Figure 8:
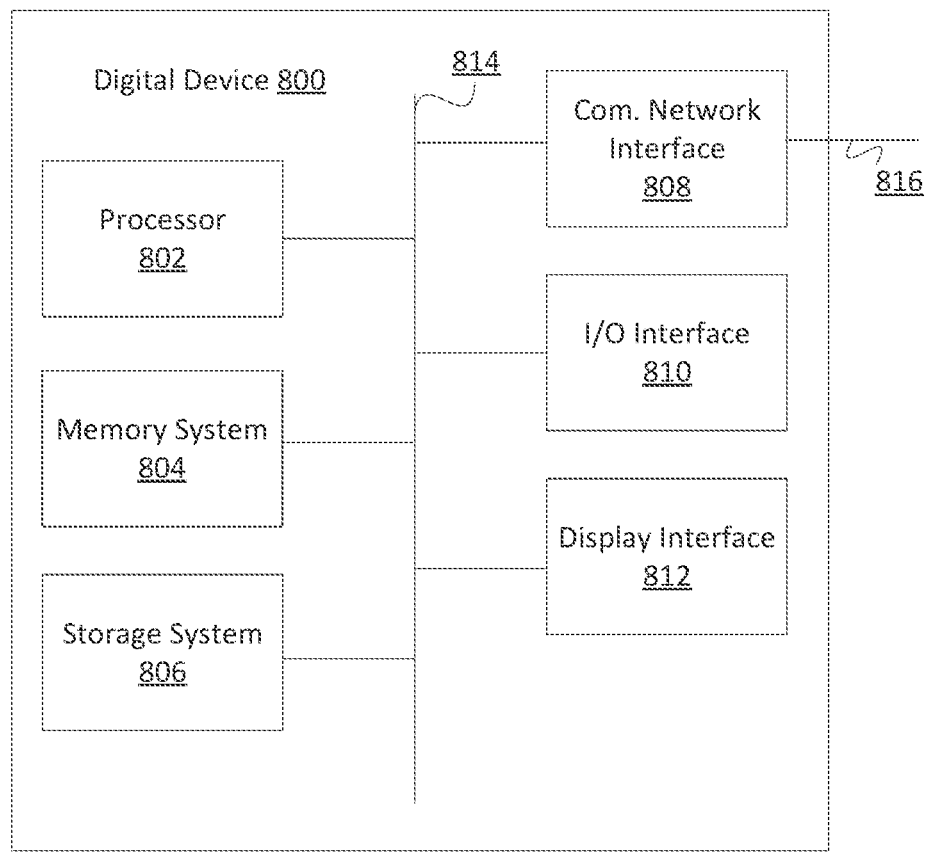
FIG. 8 is a block diagram illustrating an exemplary digital device that can be utilized in the implementation of various embodiments.

FIG. 8 is a block diagram of an exemplary digital device 800. The digital device 800 comprises a processor 802, a memory system 804, a storage system 806, a communication network interface 808, an I/O interface 810, and a display interface 812 communicatively coupled to a bus 814. The processor 802 is configured to execute executable instructions (e.g., programs). In some embodiments, the processor 802 comprises circuitry or any processor capable of processing the executable instructions.

The memory system 804 is any memory configured to store data. Some examples of the memory system 804 are storage devices, such as RAM or ROM. The memory system 804 can comprise the RAM cache. In various embodiments, data is stored within the memory system 804. The data within the memory system 804 may be cleared or ultimately transferred to the storage system 806.

The storage system 806 is any storage configured to retrieve and store data. Some examples of the storage system 806 are flash drives, hard drives, optical drives, and/or magnetic tape. In some embodiments, the digital device 800 includes a memory system 804 in the form of RAM and a storage system 806 in the form of flash data. Both the memory system 804 and the storage system 806 comprise computer readable media which may store instructions or programs that are executable by a computer processor including the processor 802.

The communications network interface (com. network interface) 808 can be coupled to a network (e.g., the computer network 104) via the link 816. The communication network interface 808 may support communication over an Ethernet connection, a serial connection, a parallel connection, or an ATA connection, for example. The communication network interface 808 may also support wireless communication (e.g., 802.11 a/b/g/n, WiMax). It will be appreciated that the communication network interface 808 can support many wired and wireless standards.

The optional input/output (I/O) interface 810 is any device that receives input from the user and output data. The optional display interface 812 is any device that is configured to output graphics and data to a display. In one example, the display interface 812 is a graphics adapter.

It will be appreciated that the hardware elements of the digital device 800 are not limited to those depicted in FIG. 8. A digital device 800 may comprise more or less hardware elements than those depicted. Further, hardware elements may share functionality and still be within various embodiments described herein. In one example, encoding and/or decoding may be performed by the processor 802 and/or a co-processor located on a GPU (i.e., Nvidia®).

Some embodiments described herein include systems and methods for non-invasive continuous blood pressure measurement. For example, a blood metrics measurement apparatus may generate multi-channel signals (e.g., PPG signals or pressure signals) which may be provided to a blood pressure calculation system to calculate arterial blood pressure values (e.g., systolic blood pressure values and/or diastolic blood pressure values). In some embodiments, the blood metrics measurement apparatus includes a pressure sensor for measuring pressure signals. In some embodiments, the blood pressure calculation system may preprocess (or, "filter") the multi-channel signals (e.g., to remove noise from the signals), select (or, "extract") subsets of "high quality" waves from the multi-channel signals, select (or, "extract") sets of features from the high quality waves, and generate sets of feature vectors based on the selected sets of features. In some embodiments, an empirical blood pressure model is used to calculate arterial blood pressure values based on the sets of feature vectors.

Figure 9:
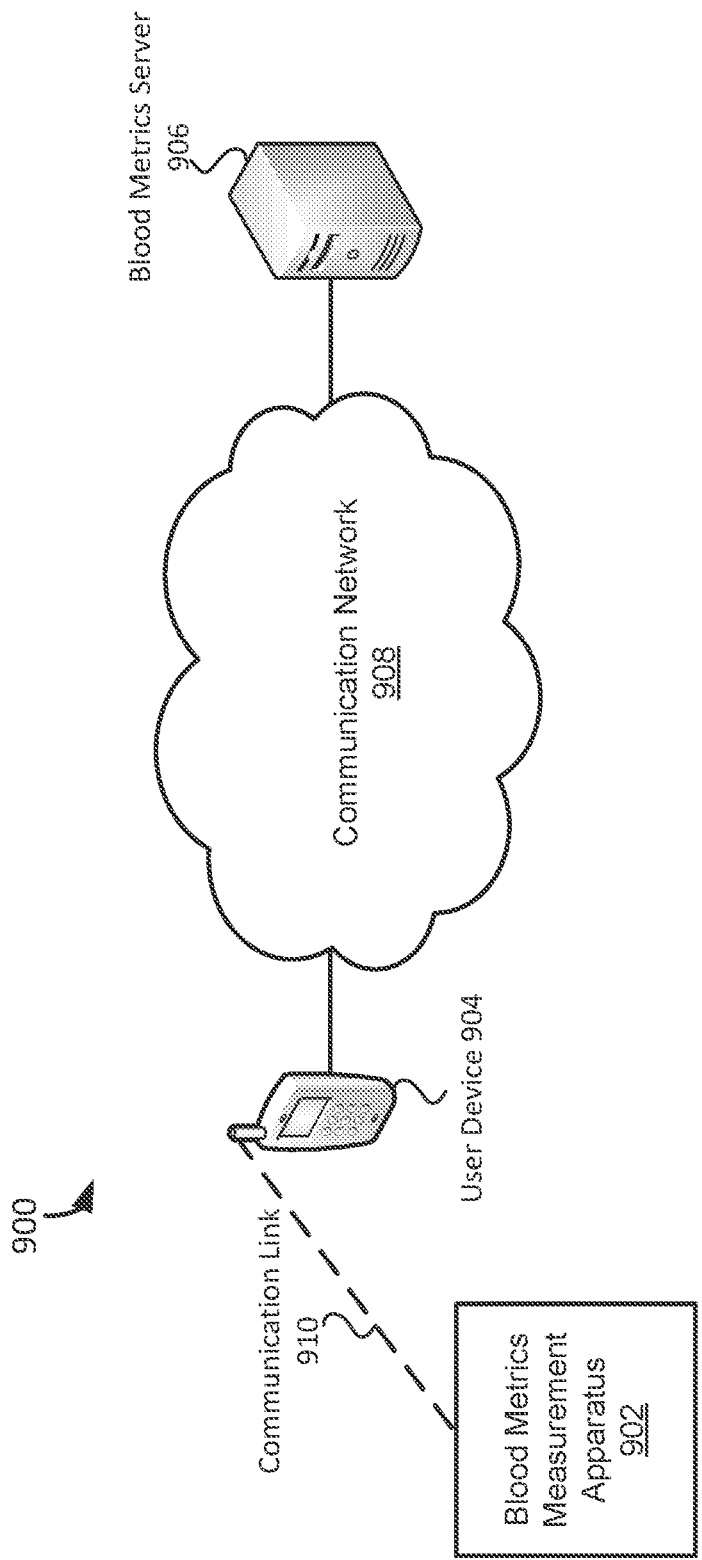
FIG. 9 depicts a block diagram of a system and environment for non-invasive blood pressure measurement according to some embodiments.

FIG. 9 depicts a block diagram of a system and environment 900 for non-invasive blood pressure measurement according to some embodiments. In some embodiments, the system and environment 900 includes a blood metrics measurement apparatus 902, a user device 904, a blood metrics server 906, a communication network 908, and a communication link 910.

The blood metrics measurement apparatus 902 may be configured to facilitate non-invasive measurement of a user's blood pressure. In some embodiments, more particularly, the blood metrics measurement apparatus 902 facilitates non-invasive continuous measurement of a user's blood pressure. It will be appreciated that non-invasive continuous measurement may include measuring arterial blood pressure in real-time without interruption (e.g., without having to inflate and deflate a cuff) and without inserting a device (e.g., a tube or catheter) into to the user's tissue or body.

In some embodiments, the blood metrics measurement apparatus 902 may project energy into tissue of a user (e.g., the wearer of the apparatus 902) and detect (or, "receive") energy reflected from and/or transmitted through tissue of the user. In some embodiments, the blood metrics measurement apparatus 902 may project energy at one or more wavelengths (e.g., 523 nm, 590 nm, 623 nm, 660 nm, 740 nm, 850 nm, 940 nm, etc.) from multiple light sources (e.g., light-emitting diodes). The detected energy may be a fraction (or, "portion") of the energy that is projected into the tissue. Energy at different wavelengths may be absorbed at a different rate that is related to a user's body state. The user's body state (e.g., heart rate, blood pressure, or the like) may determine the amount of absorbed energy. Accordingly, energy at different wavelengths may be absorbed at different levels by a user's body. The fraction of energy received (e.g., that is reflected by the tissue or transmitted through the tissue) may be used to generate signals, such as photoplethysmogram (or, "PPG") signals, at different levels. These signals may provide information of the user's body state. This information may be obtained by analyzing waveforms of the signal in a time domain and/or a frequency domain.

In some embodiments, the blood metrics measurement apparatus 902 may measure non-optical signals. For example, the blood metrics measurement apparatus 902 may be configured to non-invasively detect arterial pressure of one or more arteries of the user (e.g., radial artery or ulnar artery) based on pressure signals. Similar to optical signals, the pressure signals may be measured to provide information of the user's body state, and this information may be obtained by analyzing waveforms of the signal in a time domain and/or a frequency domain.

Functionality of the systems and modules described herein may be performed similarly with respect to both optical signals (e.g., PPG signals) and non-optical signals (e.g., pressure signals). Accordingly, it will be appreciated that signals, as used herein, may include optical signals, non-optical signals, or both.

In some embodiments, a user may comfortably wear the blood metrics measurement apparatus 902 over time. For example, the blood metrics measurement apparatus 902 may be worn without interrupting typical user activity (e.g., moving, walking, running, sleeping, etc.). The blood metrics measurement apparatus 902 may comprise lightweight components. The blood metrics measurement apparatus 902 may be made of hypoallergenic materials. The blood metrics measurement apparatus 902 may be flexibly built so that it may fit various body parts (e.g., wrist, earlobe, ankle, or chest) of a user. In some embodiments, the blood metrics measurement apparatus 902 may include some or all of the functionality of the user device 904.

In some embodiments, the blood metrics measurement apparatus 902 may be or include the apparatus 400 described with regard to FIG. 4, the blood metrics measurement apparatus 200 depicted with regard to FIG. 2, or the blood metrics measurement apparatus 102 described with regard to FIG. 1.

The user device 904 may include any digital device (e.g., mobile device) capable of executing an application related to measuring blood metrics, such as blood pressure calculation, presenting a user interface through a display and/or communicating with various entities in the example system and environment 900 through the communication network 908 and/or a communication link 910 (discussed further below). For example, through the communication link 910, the user device 902 may receive one or more blood metric measurements (e.g., one or more signals) from the blood metrics measurement apparatus 902, track and store the blood metric measurements, analyze the blood metric measurements, and/or provide recommendations and/or messages based on the blood metric measurements. An application user interface may facilitate interaction between a user of the user device 904 and an application running on the user device 904. The user device 904 may be, include, or be a part of the user system 104 described with regard to FIG. 1.

In various embodiments, the user device 904 may perform analysis of the measurements received from the blood metrics measurement apparatus 902 (e.g., calculate blood pressure values), display results, provide reports, display progress, display historic readings, track measurements, track analysis, provide alerts (or, messages), and/or the like.

The blood metrics server 906 may be configured to generate and/or store empirical blood pressure models. For example, the blood metrics server 906 may comprise one or more server computers, desktop computers, mobile devices, and/or other digital device(s). In some embodiments, the blood metrics server 906 receives and process user registration requests (e.g., user account registration requests, blood metrics measurement apparatus registration requests, etc.), provides empirical blood pressure model(s) to the user device 902 via the communication network 908, and/or the like.

As used in this paper, computing devices (e.g., digital devices) may include a mobile phone, a tablet computing device, a laptop, a desktop computer, personal digital assistant, a portable gaming unit, a wired gaming unit, a thin client, a set-top box, a portable multi-media player, or any other type of network accessible user device known to those of skill in the art. Further, the blood metrics server 908 may comprise of one or more servers, which may be operating on or implemented using one or more cloud-based services (e.g., System-as-a-Service [SaaS], Platform-as-a-Service [PaaS], or Infrastructure-as-a-Service [IaaS]).

Each of the blood metrics measurement apparatus 902, the user device 904, and the blood metrics server 906 may be implemented using one or more digital devices. An example digital device is described in FIG. 8.

In some embodiments, the communication network 908 represents one or more communication network(s). The communication network 908 may provide communication between the blood metrics measurement apparatus 902, the user device 904, and/or the blood metrics server 906. In some examples, the communication network 908 comprises digital devices, routers, cables, and/or other network topology. In other examples, the communication network 908 may be wireless and/or wireless. In some embodiments, the communication network 908 may be another type of network, such as the Internet, that may be public, private, IP-based, non-IP based, and so forth.

In some embodiments, the communication link 910 represents one or more communication network connections. The communication link 910 may provide communication between the blood metrics measurement apparatus 902 and the user device 904. In some examples, the communication link 910 comprises a network connection of the communication network 908, and/or a separate communication network. In some embodiments, the communication link 910 comprises a wireless communication link, such as a Bluetooth communication link, Wi-Fi communication link, and/or the like.

Figure 10A:
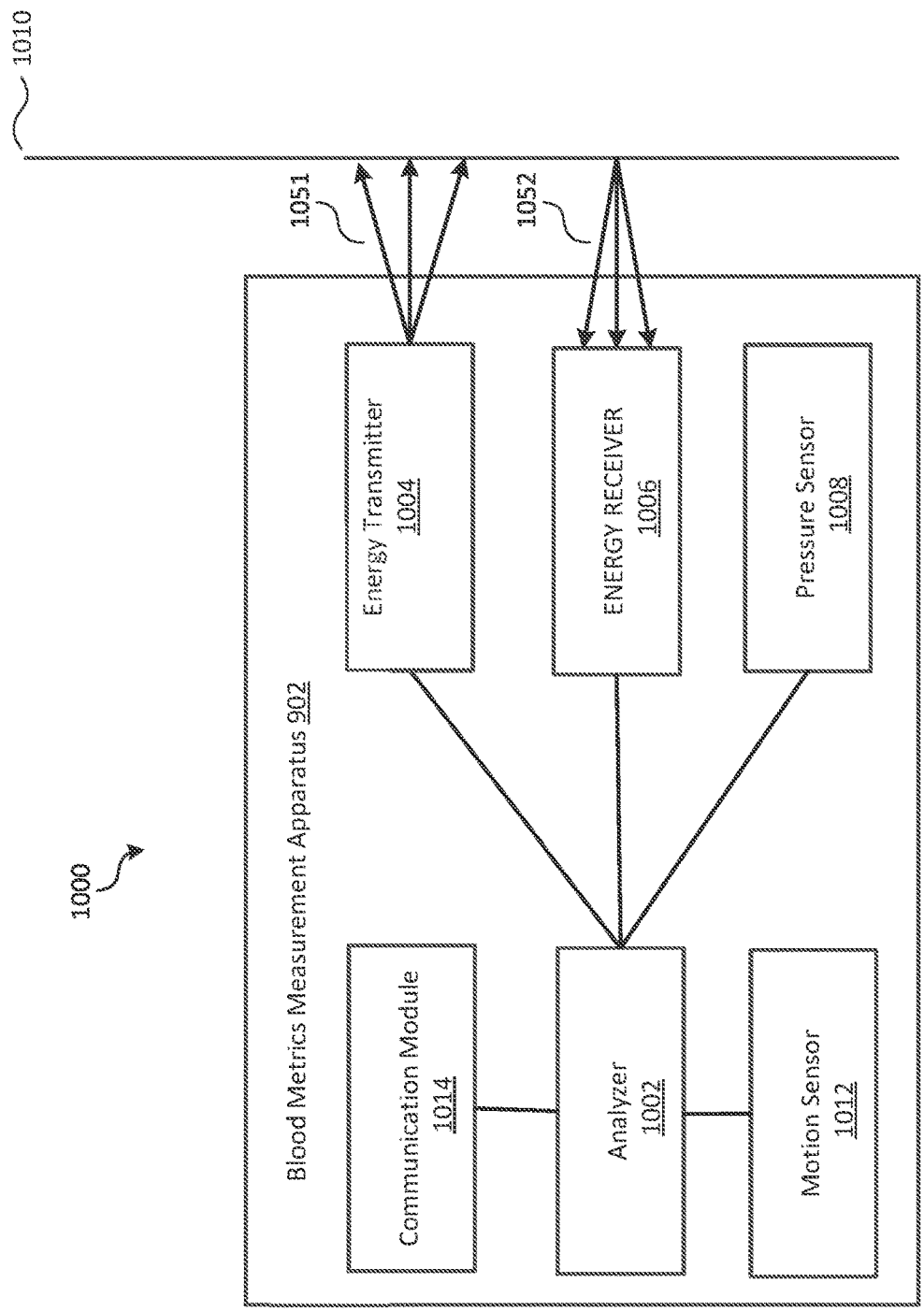
FIG. 10A depicts a block diagram of a blood metrics measurement apparatus according to some embodiments.

FIG. 10A depicts a block diagram 1000 of a blood metrics measurement apparatus 902 according to some embodiments. The blood metrics measurement apparatus 902 comprises an analyzer 1002, an energy transmitter 1004, an energy receiver 1006, a pressure sensor 1008, a motion sensor 1012, and a communication module 1014. Various embodiments may comprise a wearable member. The wearable member may include, for example, a bracelet, glasses, necklace, ring, anklet, belt, broach, jewelry, clothing, or any other member of combination of members that allow the blood metrics measurement apparatus 902 to be close to or touch a body of the wearer. In some embodiments, the blood metrics measurement apparatus 902 may further comprise a driver (not shown) and a power source (not shown). The power source may be coupled to the energy transmitter 1004 via the driver. The blood metrics measurement apparatus 902 may further comprise an Analog-to-Digital Converter ("ADC") (not shown). The ADC may be coupled to the energy receiver 1006 and the analyzer 202.

The analyzer 1002 may be coupled to the energy transmitter 1004, the energy receiver 1006, the pressure sensor 1008, the motion sensor 1012, and the communication module 1014. The energy transmitter 1004 and the energy receiver 1006 may be secured to the wearable member such that the energy transmitter 1004 and the energy receiver 1006 may make contact or be in proximity with tissues (e.g., skin) of a user. In various embodiments, the energy transmitter 1004 emits energy including, but not limited to, light, into the body of the user. The energy produced by the energy transmitter may be in the direction of entering tissues. For example, the energy produced by the energy transmitter 1004 is in a direction 1051 entering the tissue 1010. In some embodiments, the energy transmitter 1004 emits energy or light at different wavelengths. The energy transmitter 1004 may comprise any number of light emission diodes ("LEDs"). In some embodiments, the energy transmitter 1004 comprises at least two LEDs. Each LED may be configured to emit energy at one or more wavelengths. In another example, each LED may emit light with a peak wavelength centered around a wavelength. In one example, the energy transmitter 1004 may emit light with a peak wavelength centered around 500 nm to 1800 nm, although the wavelength may include a variety of spectrums (e.g., IR, near-IR, and the like).

Each wavelength may correspond to one or more blood metrics of interest and/or one or more nutrients. It will be appreciated that different components of the blood and/or different nutrients may absorb energy at different wavelengths. In various embodiments, a controller, driver, analyzer 1002, or the like may receive a blood metric or nutrient of interest (e.g., from a user of the blood metrics measurement apparatus 902 and/or a user device not shown). The controller, driver, analyzer 1002 or the like may associate the blood metric and/or nutrient of interest with one or more wavelengths and configure one or more of the LEDs to emit energy of at least one of the one or more wavelengths. For example, the analyzer 1002 may command the driver to deliver electric power to one LED that is configured to emit light at the desired wavelength.

The energy receiver 1006 may detect energy associated with the energy provided by the LEDs from tissues (e.g., skin) of the user. In this example, received and/or detected energy is in the direction 1052 that leaves from the tissue 1010. In various embodiments, the energy receiver 1006 may detect energy from the body of the user that is a fraction of the energy produced by the energy transmitter 1004.

The energy transmitter 1004 and the energy receiver 1006 may be configured such that the energy receiver 1006 detects reflected energy from tissues of the user of the multispectral blood metrics measurement apparatus 902. For example, the energy transmitter 1004 and the energy receiver 1006 may be configured to be disposed on one surface or side of a user's tissue. The energy transmitter 1004 and the energy receiver 1006 may be configured such that the energy receiver 1006 detects energy from the energy transmitter 1004 that passes through or reflects from the user's tissues. In some embodiments, the energy transmitter 1004 and the energy receiver 1006 may be configured to be disposed on different (e.g., opposite) surfaces or sides of a users' tissue.

The energy transmitter 1004 may be configured to generate energy at a set of wavelengths. In some embodiments, the energy transmitter 1004 is configured to generate energy such that energy at different wavelengths is generated sequentially and/or periodically. The energy transmitter 1004 may be configured to generate energy at each particular wavelength until energy at all wavelengths of a set is generated. The period of time for the energy transmitter 1004 to generate energy at all wavelengths is a generation period. Subsequent to completion of the generation period, the energy transmitter 1004 may start a new generation period thereby allowing multiple measurements.

Energy detected from tissues of a user may be detected by the energy receiver 1006. The energy receiver 1006 may be configured to generate a signal in response to the detected energy. In some embodiments, the energy receiver 1006 may be triggered by the energy received to generate an output which may be dependent or partially dependent upon the amount of energy received. The energy receiver 1006 may be configured to generate a signal (e.g., an electric current, or an electric voltage) in response to the energy received from the tissues.

The signal generated by the energy receiver 1006 may be associated with one or more blood metrics and/or nutrients of interest. Energy at different wavelengths may be absorbed at a different rate that is related to a user's body state. The user's body state (e.g., heart rate, blood pressure, nutrient level, or the like) may determine the amount of energy absorbed by the body. Accordingly, energy from the user's body at different wavelengths may be detected at different levels thereby causing different responses of the energy receiver 1006. The energy receiver 1006 may, for example, output signals based on the level of the energy received.

The energy receiver 1006 may provide information associated with the user's body state. Blood metric information may be determined (e.g., by the analyzer 1002) from the output signal of the energy receiver 1006. In some embodiments, the energy receiver 1006 may comprise a set of photodetectors (e.g., a photo diode, or a photo transistor) which are configured to output a signal dependent upon photons or the like from the energy transmitter 1004 that passed through tissues of the user.

In various embodiments, the output signal of the energy receiver 1006 is a composite of multiple signals. Each signal of the composite may be associated with energy at a wavelength which may be a portion (or fraction) of the total energy emitted by the energy transmitter 1004.

The pressure sensor 1008 may be configured to generate, detect, and/or measure non-optical signals. For example, the pressure sensor 1008 may non-invasively and continuously generate, detect and/or measure pressure pulse signals. In some embodiments, the pressure sensor 1008 measures pressure pulse waveforms associated with arterial pressure of one or more arteries of a user. In various embodiments, the blood metrics measurement apparatus 902 may include the energy transmitter 1004 to generate optical signals and the energy receiver 1006 to receive optical signals but not the pressure sensor 1008. Alternately, the blood metrics measurement apparatus 902 may include the pressure sensor 1008 that may produce pressure on the user's body and/or receive measurements based on that pressure but not the energy transmitter 1004 or the energy receiver 1006 to receive optical signals.

In some embodiments, the motion sensor 1012 may be configured to detect position and orientation of the blood metrics measurement apparatus 902, and detect motion of the blood metrics measurement apparatus 902. For example, the blood metrics measurement apparatus 902 may detect position, orientation, and motion along an x, y, or z-axis, and measured values may include velocity, acceleration, distance, and the like. In some embodiments, the motion sensor 1012 may include one or more accelerometers, gyroscope, global positioning systems, or the like. The motion sensor may be coupled to the analyzer 1002.

The communication module 1014 may be configured to send requests to and receive data from one or a plurality of systems. The communication module 1014 may send requests to and receive data from a systems through a network or a portion of a network. Depending upon implementation-specific or other considerations, the communication module 1014 may send requests and receive data through a connection (e.g., the communication link 910), all or a portion of which may be a wireless connection. The communication module 1014 may request and receive messages, and/or other communications from associated systems.

Figure 10B:
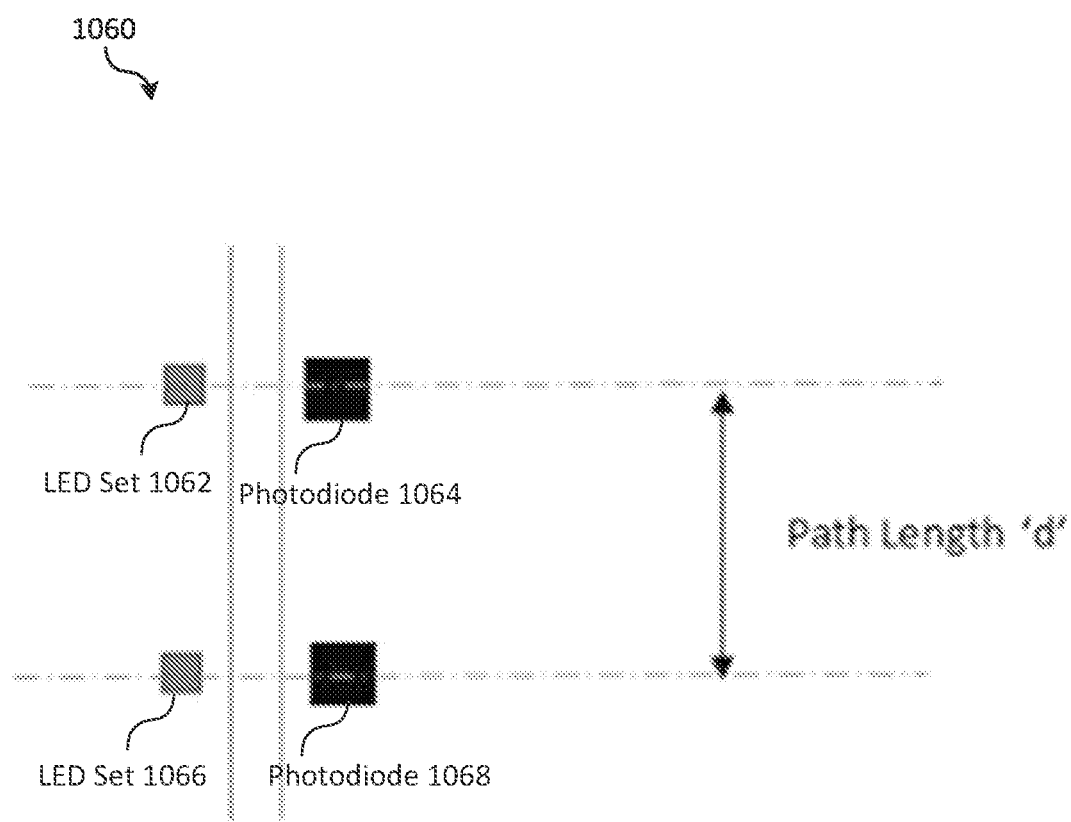
FIG. 10B depicts a block diagram of a sensor system according to some embodiments.

FIG. 10B depicts a block diagram of a sensor system 1060 according to some embodiments. In some embodiments, the sensor system 1060 may be disposed in the blood metrics measurement apparatus 902. For example, the energy transmitter 1004 and the energy receiver 1006 may comprise the sensor system 1060. As shown, the sensor system 1060 comprises two sets of multi-LED energy transmitters (i.e., LED set 1062 and 1066 each referred to as energy transmitters herein), and two sets of corresponding photodiode energy receivers 1064 and 1068. It will be appreciated that each pair of corresponding energy transmitters and energy receivers (e.g., energy transmitter 1062 and energy receiver 1064 as well as energy transmitter 1066 and energy receiver 1068) may be referred to as an LED-PD system, and the sensor system 1060 may include any number of such LED-PD systems, although only two are shown here.

In some embodiments, the energy transmitters 1062 and 1066 each comprise a set of LEDs (e.g., between 2-4 LEDs) configured to transmit a variety of wavelengths into tissue of a user. The corresponding energy receivers 1064 and 1068 may each comprise one or more photodiodes which receive returning light from the corresponding energy transmitters 1062 and 1066 after passage through tissue. In some embodiments, the energy transmitter 1062 and the energy receiver 1064 may be spaced at a predetermined distance (e.g., 15 mm) from the energy transmitter 1066 and the energy receiver 1068. Similarly, each energy transmitter 1062 and 1066 may be spaced at a predetermined distance (e.g., 10 mm) from a corresponding energy receiver 1064 and 1068.

In some embodiments, the sensor system 1060 may be mounted on a user's wrist along the radial artery, or other area of the user's body along arterial pathways (e.g., ulnar artery). The sensor system 1060 may include an accelerometer and gyroscope for detecting position and orientation information.

In some embodiments, the sensor system 1060 may include a pressure sensor. For example, at least one LED within each LED-PD system may be configured to sample data from tissue at a very high frequency (upwards of 1 KHz), and the other LEDs may sample at a lower rate (around 50-100 Hz). The channels sampling data at high frequency may be referred to as the fast LED channels, and the channels sampling data at lower frequency may be referred to as slow LED channels.

In some embodiments, the sensor system 1060 may be included as a part of the blood metrics measurement apparatus 902 described with regard to FIGS. 9 and 10A, the apparatus 400 described with regard to FIG. 4, the blood metrics measurement apparatus 200 described with regard to FIG. 2, or the blood metrics measurement apparatus 102 described with regard to FIG. 1. Similarly, the analyzer 202 may be or include a part of analyzer 1002 described with regard to FIG. 2 or the central unit 402 described with regard to FIG. 4. The energy transmitter 1004 may be or include a part of energy transmitter 204 described with regard to FIG. 2 or the central unit 402 described with regard to FIG. 4. The energy receiver 1006 may be or include energy receiver 206 described with regard to FIG. 2 or the central unit 402 described with regard to FIG. 4.

Figure 11:
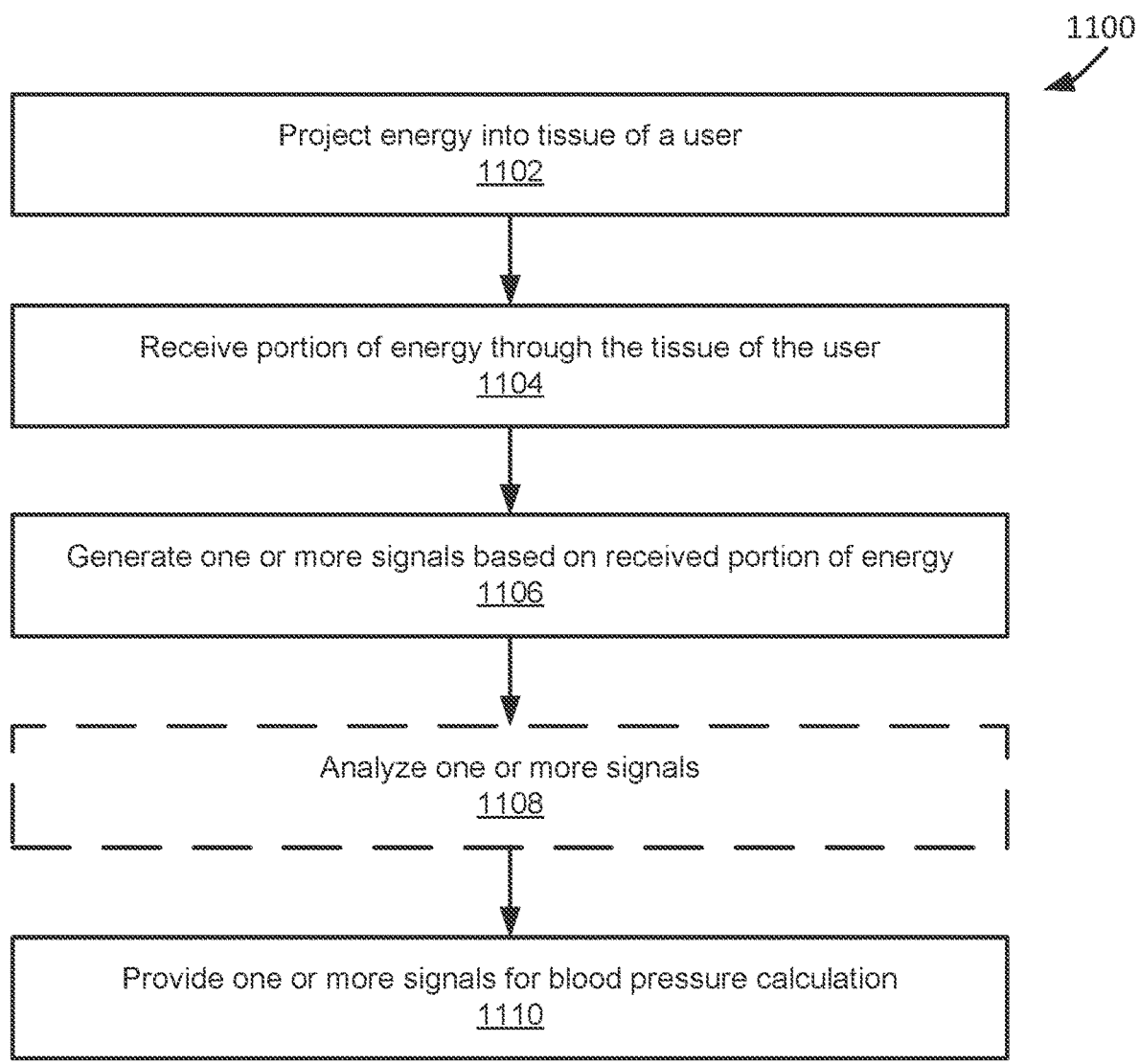
FIG. 11 depicts a flowchart of an example method of operation of a blood metrics measurement apparatus according to some embodiments.

FIG. 11 depicts a flowchart 1100 of an example method of operation of a blood metrics measurement apparatus (e.g., blood metrics measurement apparatus 902) according to some embodiments. In this and other flowcharts described herein, the flowchart illustrates by way of example a sequence of steps. It should be understood the steps may be reorganized for parallel execution, or reordered, as applicable. Moreover, some steps that could have been included may have been removed to avoid providing too much information for the sake of clarity and some steps that were included could be removed, but may have been included for the sake of illustrative clarity.

In step 1102, a blood metrics measurement apparatus projects energy into tissue of a user (e.g., the user wearing blood metrics measurement apparatus). The energy may be projected from a transmitter (e.g., energy transmitter 1004) comprising a plurality of light sources (e.g., LEDs). In some embodiments, a first light source (e.g., one or more LEDs) may project light energy at a plurality of different wavelengths, such as 523 nm, 590 nm, 623 nm, 660 nm, 740 nm, 850 nm, and 940 nm, and a second light source (e.g., one or more LEDs) may project energy at the same, or substantially similar, wavelength as one of the wavelengths projected by the first light source (e.g., 523 nm, 590 nm, 623 nm, 660 nm, 740 nm, 850 nm, or 940 nm). It will be appreciated that other configuration may be used (e.g., a greater number of light sources) a greater or lesser number of wavelengths projected from the lights sources, and so forth.

In step 1104, the blood metrics measurement apparatus receives (or, "detects) portions of energy through the tissue of the user. In some embodiments, an energy receiver (e.g., energy transmitter 1006) detects a portion of the energy transmitted into the user's tissue by the energy transmitter. The energy receiver may generate a signal based on the portion of energy detected (e.g., based on the amount of the energy detected). For example, energy detected may be a portion of the energy projected at step 1102 reflected by the tissue. By way of further example, energy detected may be a portion of the energy projected at step 1102 that passes through the tissue (e.g., other undetected energy may be absorbed by tissue and/or otherwise blocked). In various embodiments, steps 1102 and 1104 are performed simultaneously or substantially simultaneously. That is, energy projection and detection may be performed approximately simultaneously.

In step 1106, the blood metrics measurement apparatus generates one or more signals based on the received portions of energy. In some embodiments, the energy receiver may generate a multi-channel PPG signal (e.g., as mentioned above). The output (or, "generated") signal of the energy receiver may be an electric current or an electric voltage, of which the amplitude may be related to the amount of the energy detected.

In various embodiments, analysis of the signals from the energy receiver may identify abnormal measurements. For example, each of the measurements may be compared to a predetermined value. If the difference between the measurement and the predetermined value is above (or below) a threshold, then the measurement may be determined to be abnormal. An abnormal value may trigger additional analysis or an alert. In some embodiments, an abnormal value is ignored (e.g., as possibly effected by noise caused by movement of the energy transmitter and/or the energy receiver). In various embodiments, the abnormal value may be discounted (e.g., the weight of the value reduced). The degree of discount may be based, for example, on information from an accelerometer (e.g., a large acceleration may indicate that the abnormal value should be significantly discounted) and/or based on historical values. It will be appreciated that the degree of discount may be based on any number of factors.

In some embodiments, measurements may be averaged over a period of time. A Kalman filer (e.g., a nonlinear, unscented Kalman filter) may be applied to any number of measurements or averaged measurements. A motion measurement (e.g., a measurement by an accelerometer) may be considered. Upon determining a measurement is abnormal, the motion measurement for that time point may be inspected. A large measurement may indicate large vibrations or accelerations that corroborate that the measurement may be abnormal. Measurements collected in such situations are likely to have significant electrical noises.

At step 1108, the blood metrics measurement apparatus analyzes signals from the energy receiver analyzed in the frequency domain to determine blood metrics. Concentration of a nutrient in the blood may subsequently be determined. In some embodiments, signals may be provided to a bandpass filter that separates AC components from DC components. An AC component may represent signal variation at the cardiac frequency and a DC component may represent the average overall transmitted light intensity. In some embodiments, a heart rate and/or oxygen saturation, $SpO_2$ may be determined. The heart rate may be determined, for example, by averaging the maximum frequency to determine the rate of cardiac beats in a predetermined amount of time. The oxygen saturation $SpO_2$ may be determined according to Equation (1):

$$S_pO_2 = 110 - 25 \times R \quad (1),$$

where R is the ration of a red and infrared normalized transmitted light intensity. R may be determined according to Equation (2):

$$R = \frac{AC_R/DC_R}{AC_{IR}/DC_{IR}}, \quad (2)$$

where the $AC_R$ is the AC component of the detected energy corresponding to a wavelength (e.g., red light), $DC_R$ is the DC component of the detected energy corresponding to the wavelength (e.g., red light), $AC_{IR}$ is the AC component of the detected energy corresponding to a different wavelength (e.g., infrared light), and $DC_{IR}$ is the DC component of the detected energy corresponding to the different wavelength (e.g., infrared light). In some embodiments, the AC component may be selected as the highest spectral line in the cardiac frequency band. Waveform analysis may be performed to determine the R-R interval defined by two successive AC components, an elapsed interval and the probation, if there is any.

It will be appreciated that analysis may be performed by the analyzer and/or any other digital device (e.g., user device or a blood metrics server such as blood metrics server 906).

State space estimation and progression may be performed to determine blood metrics. A system may be modeled according to Equation (3):

$$x(n+1) = f[x(n)] + u(n)$$

$$y(n) = h[x(n)] + v(n) \quad (3),$$

where x(n) represents the state of the system, u(n) is process noise, y(n) is the vector of the observed signals, and v(n) is the measurement noise.

Table 1 lists one or more parameters for x(n) as well as their initial value in some embodiments:

TABLE 1

| Parameter | Symbol | Initial Value |
|---|---|---|
| Cardiac frequency | $f_{HR}$ | 1 Hz |
| Cardiac phase | $\theta_{HR}$ | 0 |
| Cardiac harmonic amplitude | $I_{Harmonic}^{HR}$ | 0 |
| Cardiac Pulse Pressure | $P_{HR}$ | 1 |
| Point Blood Pressure | $P_{Point}$ | 1 |
| Respiratory frequency | $f_{Resp}$ | 0.3 Hz |
| Respiratory phase | $\theta_{Resp}$ | 0 |
| Wavelength i = 1..N AC peak amplitude | $I_{\lambda,i}^{AC}$ | 0.5 max_value |
| Wavelength i = 1..N AC peak location | $pos_{\lambda,i}^{AC}$ | Corresponding FFT bin to 1 Hz |
| Wavelength i = 1..N DC | $I_{\lambda,i}^{DC}$ | 0.5 max_value |
| Wavelength i = 1..N p2p amplitude | $I_{\lambda,i}^{p2p}$ | 1 ADC read |
| Wavelength i = 1..N rise time | $\tau_{\lambda,i}^{rise}$ | 0.1 sec |
| Wavelength i = 1..N Significance coefficient | $c_{\lambda,i}$ | 1 |
| Wavelength i = 1..N HRV | $T_{\lambda,i}^{HRV}$ | 1 sec |
| Best Ratio pH | $BR_{pH}$ | 2 |
| Best Ratio pCO2 | $BR_{pCO2}$ | 3 |
| Best Ratio pHCO3− | $BR_{pHCO3-}$ | 4 |
| Acceleration magnitude | $I_{move}$ | 0 |
| GPS velocity | $|v|_{GPS}$ | 0 |
| GPS altitude | $|alt|_{GPS}$ | 0 |
| GPS acceleration | $|\alpha|_{GPS}$ | 0 |
| GPS incline | $|incline|_{GPS}$ | 0 |
| Restfulness | Rest | 0 |
| Hydration | Hyd | 0 |
| Systolic Blood Pressure | SBP | 120 mmHg |
| Diastolic Blood Pressure | DBP | 80 mmHg |
| End tidal CO2 | ETCO2 | 40 mmHg |
| Blood Carbon | SpCO | 0% |

TABLE 1-continued

| Parameter | Symbol | Initial Value |
|---|---|---|
| Monoxide | | |

Table 2 lists one or more parameters for y(n) as well as their initial value in some embodiments:

TABLE 2

| Parameter | Symbol | Initial |
|---|---|---|
| Blood pH | pH | 7.35 |
| Blood PCO2 | $pCO_2$ | 24 mmol |
| Blood PO2 | $pO_2$ | 24 mmol |
| Blood PHCO3− | $pHCO_3^-$ | 24 mmol |
| Blood Glucose | $pC_6H_{12}O_6$ | 3 mmol |

TABLE 2-continued

| Parameter | Symbol | Initial |
|---|---|---|
| Cardiac Frequency | $f_{HR}$ | 1 |
| Point Blood Pressure | $P_{Point}$ | 1 |
| Respiratory Frequency | $f_{Resp}$ | 0.3 |
| Parameter | | |
| GPS velocity | $|v|_{GPS}$ | |
| GPS altitude | $|alt|_{GPS}$ | 0 |
| GPS acceleration | $|a|_{GPS}$ | 0 |
| GPS incline | $|incline|_{GPS}$ | 0 |
| | pH | 0 |

Table 3 lists the state space model F(X(n)) between the parameters listed in Table 1 and Table 2 in some embodiments, where the energy wavelengths comprise 880 nm, 631 nm, 1450 nm, and 1550 nm:

TABLE 3

| Name | Symbol | Equation |
|---|---|---|
| Cardiac frequency | $f_{HR}$ | $\text{bin\_to\_freq}\left(\frac{\Sigma c_{\lambda_i} pos_{\lambda_i}^{AC}}{\Sigma c_{\lambda_i}}\right)$ |
| Cardiac phase | $\theta_{HR}$ | $\theta_{HR}(n-1) + f_s^{-1} * \omega^*$, where $\omega^* \in [\omega\_min, \omega\_max]$ |
| Cardiac harmonic amplitude | $I_{HR}$ | $\frac{\Sigma c_{\lambda_i} I_{\lambda_i}^{p2p}}{\Sigma c_{\lambda_i}}$ |
| Cardiac Pulse Pressure | $P_{HR}$ | $\left(\frac{\Sigma c_{\lambda_i} \tau_{\lambda_i}^{rise}}{\Sigma c_{\lambda_i}}\right)^\Lambda - 1$ |
| Point Blood Pressure | $P_{point}$ | $\tau_{\lambda_1}^{rise^{-1}}$ |
| Respiratory frequency | $f_{Resp}$ | 3) Respiratory and Heart Rate State Models: The fluctuations in the respiratory rate $\omega_r(n)$ and fluctuations in the heart rate $\omega_{ca}(n)$ that are not due to RSA are both modeled as a first-order autoregressive process with a mean and mild nonlinearity that limit the frequencies to know physiologic ranges<br>$\omega_r(n+1) = \overline{\omega}_r + \alpha_r\{s_r[\omega_r(n)] - \overline{\omega}_r\} + u_{\omega_s}(n)$    (15)<br>$\omega_{ca}(n+1) = \overline{\omega}_c + \alpha_c\{s_c[\omega_{ca}(n)] - \overline{\omega}_c\} + u_{\omega_{ca}}(n)$    (16)<br>where $\overline{\omega}_r$ and $\overline{\omega}_c$ are the a priori estimates of the expected respiratory and cardiac frequencies, respectively; $\alpha_r$ and $\alpha_c$ control the bandwidth of the frequency fluctuations; and $u_{\omega_r}(n)$ and $u_{\omega_{ca}}(n)$ are white noise processes that model the random variation in the respiratory and cardiac frequencies, respectively. The instantaneous respiratory and heart rates in units of Hz are then<br>$f_r(n) = \frac{1}{2\pi T_s} s_r[\omega_r(n)]$    (17)<br>$f_c(n) = \frac{1}{2\pi T_s} s_c[\omega_c(n)]$    (18) |
| Respiratory phase | $\theta_{Resp}$ | $\theta_{Resp}(n-1) + f_s^{-1} * \omega^*$, where $\omega^* \in [\omega\_min, \omega\_max]$ |
| $\lambda = 880$ nm AC peak | $I_{\lambda_i}^{AC}$ | From FFT |
| $\lambda = 880$ nm DC | $pos_{\lambda_i}^{AC}$ | From FFT |
| $\lambda = 880$ nm p2p amplitude | $I_{\lambda_i}^{DC}$ | From Waveform analysis |
| $\lambda = 880$ nm rise time | $I_{\lambda_i}^{p2p}$ | From Waveform analysis |
| $\lambda = 880$ nm signal trend | $\tau_{\lambda_i}^{rise}$ | From Waveform analysis |
| $\lambda = 880$ nm Significance | $c_{\lambda_i}$ | From Waveform analysis |

TABLE 3-continued

| Name | Symbol | Equation |
|---|---|---|
| coefficient | | |
| $\lambda = 880$ nm HRV | $T_{\lambda_i}^{HRV}$ | From Waveform analysis |
| $\lambda = 631$ nm AC peak | $I_{\lambda_i}^{AC}$ | From Fast Fourier Transformation ("FFT") |
| $\lambda = 631$ nm DC | $pos_{\lambda_i}^{AC}$ | From FFT |
| $\lambda = 631$ nm p2p amplitude | $I_{\lambda_i}^{DC}$ | From Waveform analysis |
| $\lambda = 631$ nm rise time | $I_{\lambda_i}^{p2p}$ | From Waveform analysis |
| $\lambda = 631$ nm signal trend | $\tau_{\lambda_i}^{rise}$ | From Waveform analysis |
| $\lambda = 631$ nm Significance coefficient | $c_{\lambda_i}$ | From Waveform analysis |
| $\lambda = 631$ nm HRV | $T_{\lambda_i}^{HRV}$ | From Waveform analysis |
| $\lambda = 1450$ nm AC peak | $I_{\lambda_i}^{AC}$ | From FFT |
| $\lambda = 1450$ nm DC | $pos_{\lambda_i}^{AC}$ | From FFT |
| $\lambda = 1450$ nm p2p amplitude | $I_{\lambda_i}^{DC}$ | From Waveform analysis |
| $\lambda = 1450$ nm rise time | $I_{\lambda_i}^{p2p}$ | From Waveform analysis |
| $\lambda = 1450$ nm signal trend | $\tau_{\lambda_i}^{rise}$ | From Waveform analysis |
| $\lambda = 1450$ nm Significance coefficient | $c_{\lambda_i}$ | From Waveform analysis |
| $\lambda = 1450$ nm HRV | $T_{\lambda_i}^{HRV}$ | From Waveform analysis |
| $\lambda = 1550$ nm AC peak | $I_{\lambda_i}^{AC}$ | From FFT |
| $\lambda = 1550$ nm DC | $pos_{\lambda_i}^{AC}$ | From FFT |
| $\lambda = 1550$ nm p2p amplitude | $I_{\lambda_i}^{DC}$ | From Waveform analysis |
| $\lambda = 1550$ nm rise time | $I_{\lambda_i}^{p2p}$ | From Waveform analysis |
| $\lambda = 1550$ nm signal trend | $\tau_{\lambda_i}^{rise}$ | From Waveform analysis |
| $\lambda = 1550$ nm Significance coefficient | $c_{\lambda_i}$ | From Waveform analysis |
| $\lambda = 1550$ nm HRV | $T_{\lambda_i}^{HRV}$ | From Waveform analysis |
| Best Ratio pH | $BR_{pH}$ | Device Calibration |
| Best Ratio pCO2 | $BR_{pCO2}$ | Device Calibration |
| Best Ratio pHCO3- | $BR_{pHCO3^-}$ | Device Calibration |
| Acceleration magnitude | $I_{move}$ | From Accelerometer |
| GPS velocity | $|v|_{GPS}$ | From GPS |
| GPS altitude | $|alt|_{GPS}$ | From GPS |
| GPS acceleration | $|a|_{GPS}$ | From GPS |
| GPS incline | $|incline|_{GPS}$ | From GPS |

Table 4 lists Y(n)=H(x(n)):

TABLE 4

| Name | Symbol | Equation |
|---|---|---|
| Blood pH | pH | $6.1 + \log\left(\dfrac{pHCO_3^-}{0.03 pCO_2}\right)$ |

TABLE 4-continued

| Name | Symbol | Equation |
|---|---|---|
| Blood PCO2 | pCO$_2$ | $\dfrac{\epsilon_{Hb}^{CO_2} - \epsilon_{Hb}^{Hb} * I_{\lambda_{CO_2}}^{AC} * I_{\lambda_1}^{DC} / \left(I_{\lambda_1}^{AC} * I_{\lambda_{CO_2}}^{DC}\right)}{\epsilon_{Hb}^{CO_2} - \epsilon_{CO_2}^{CO_2} + \left(\epsilon_{CO_2}^{Hb} - \epsilon_{Hb}^{Hb}\right) * I_{\lambda_{CO_2}}^{AC} * I_{\lambda_1}^{DC} / \left(I_{\lambda_1}^{AC} * I_{\lambda_{CO_2}}^{DC}\right)}$ |
| Blood PO2 | pO$_2$ | $\dfrac{\epsilon_{Hb}^{CO_2} - \epsilon_{Hb}^{Hb} * I_{\lambda_{CO_2}}^{AC} * I_{\lambda_1}^{DC} / \left(I_{\lambda_1}^{AC} * I_{\lambda_{CO_2}}^{DC}\right)}{\epsilon_{Hb}^{CO_2} - \epsilon_{CO_2}^{CO_2} + \left(\epsilon_{CO_2}^{Hb} - \epsilon_{Hb}^{Hb}\right) * I_{\lambda_{CO_2}}^{AC} * I_{\lambda_1}^{DC} / \left(I_{\lambda_1}^{AC} * I_{\lambda_{CO_2}}^{DC}\right)}$ |
| Blood PHCO3- | pHCO$_3^-$ | $\dfrac{\epsilon_{Hb}^{HCO_3^-} - \epsilon_{Hb}^{Hb} * I_{\lambda_{HCO_3^-}}^{AC} * I_{\lambda_1}^{DC} / \left(I_{\lambda_1}^{AC} * I_{\lambda_{HCO_3^-}}^{DC}\right)}{\epsilon_{Hb}^{HCO_3^-} - \epsilon_{HCO_3^-}^{HCO_3^-} + \left(\epsilon_{HCO_3^-}^{Hb} - \epsilon_{Hb}^{Hb}\right) * I_{\lambda_{HCO_3^-}}^{AC} * I_{\lambda_1}^{DC} / \left(I_{\lambda_1}^{AC} * I_{\lambda_{HCO_3^-}}^{DC}\right)}$ |
| Blood Glucose | pC$_6$H$_{12}$O$_6$ | As above |
| Cardiac Frequency | f$_{HR}$ | As in f(x(n)) |
| Point Blood Pressure | P$_{Point}$ | As in f(x(n)) |
| Respiratory Frequency | f$_{Resp}$ | As in f(x(n)) |
| GPS velocity | \|v\|$_{GPS}$ | As in f(x(n)) |
| GPS altitude | \|alt\|$_{GPS}$ | As in f(x(n)) |
| GPS acceleration | \|a\|$_{GPS}$ | As in f(x(n)) |
| GPS incline | \|incline\|$_{GPS}$ | As in f(x(n)) |

As illustrated in Tables 3 and 4, by generating energy at different wavelengths, one or more blood metrics may be determined from the detected energy. For example, cardiac frequency, cardiac phase, cardiac harmonic amplitude, cardiac pulse pressure, point blood pressure, respiratory frequency, respiratory phase, blood pH, blood pCO$_2$, blood pHCO$_{3-}$, or blood glucose, may be determined.

In step 1110, the blood metrics measurement apparatus provides the generated one or more signals for blood pressure calculation. In some embodiments, a communication module (e.g., communication module 1008) provides the one or more signals (e.g., to a blood pressure calculation system and/or user device).

Figure 12:
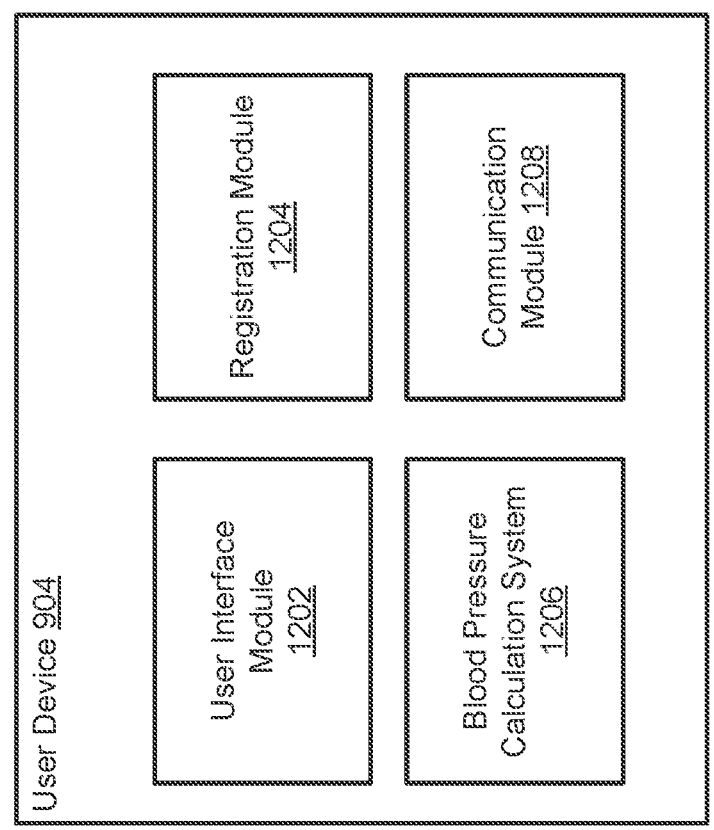
FIG. 12 depicts a block diagram of a user device according to some embodiments.

FIG. 12 depicts a block diagram 1200 of a user device 904 according to some embodiments. Generally, the user device 904 may be configured to display, or otherwise present blood pressure values, messages, alerts, and/or the like. The user device 904 may also provide registration features allowing a user to register a blood metrics measurement device 902, create and/or update a user account, and communicate with other systems of the system and environment 900. In some embodiments, the user device 904 includes a user interface module 1202, a registration module 1204, a blood pressure calculation system 1206, and a communication module 1208. In some embodiments, the blood metrics measurement device 902 may include all or part of the blood pressure calculation system 1206.

The user interface module 1202 may be configured to present images and/or audio corresponding to health data, such as blood pressure values, messages, alerts, and the like. For example, the user interface module 1202 may display one or more graphical user interfaces (GUIs) to present a calculated blood pressure to a user. Example user interfaces are described further with reference to FIG. 5-7, discussed above.

The registration module 1204 may be configured to generate registration requests to create, read, update, delete, or otherwise access, registration records associated with user accounts (e.g., a user account associated with a user of the user device 904 and/or the blood metrics measurement apparatus 902) and registration records associated with the blood metrics measurement apparatus 902. In some embodiments, a user inputs user account registration information and blood metrics measurement apparatus registration information via the user interface module 1202. For example, user account registration information may include geographic attributes, demographic attributes, psychographic attributes, and/or behavioristic attributes. Accordingly, user account registration information may include some or all of the following attributes:

User Account Identifier: Identifier that identifies a user account.

Password: Password, or other personal identifier, used to authenticate the user account. For example, it may an alphanumerical password, biometric data (e.g., fingerprint, etc.). In some embodiments, readings or measurements from the blood metrics measurement apparatus 902 may be used to authenticate the user account.

Device Identifier(s): Identifier(s) that identify one or more blood metric measurement apparatus' associated with the user account.

Name: A name of the user.

DOB: A date of birth of the user.

Age: An age of the user.

Gender: Gender of the user (e.g., female, male, transgender, or the like).

Weight: A weight of the user.

Height: A height of the user.

Skin color: A skin color of the user.

Activity Level: An activity level of the user (e.g., sedentary, lightly active, active, very active, and so forth).

Geographic location: A location of the user (e.g., as determined by a location service and/or specified by the user).

Blood Pressure Profile: Hypertensive, Hypotensive, Normal or unknown.

Blood Glucose Profile (e.g., Diabetes information)

Wrist circumference: Circumference of the user's wrist.

In some embodiments, the blood metrics measurement apparatus registration information includes some or all of the following attributes:

Apparatus Identifier: Identifier that identifies a blood metrics measurement apparatus.

User Account Identifier: Identifier that identifies a user account associated with the blood metrics measurement apparatus.

Geographic location: A current location of the blood metrics measurement apparatus (e.g., as determined by a location service and/or specified by the user).

Settings: One or more settings of the blood measurement metrics apparatus. For example, some or all of the settings may be automatically determined based on one or more user account attributes (e.g., height, weight, or the like) and/or by the user.

The blood pressure calculation system 1206 may be configured to calculate blood pressure values (e.g., systolic, diastolic), and generate messages or alerts based on those values. An example of the blood pressure calculation system 1206 is discussed further below with reference to FIG. 14.

The communication module 1208 may be configured to send requests to and receive data from one or a plurality of systems. The communication module 1208 may send requests to and receive data from a systems through a network or a portion of a network. Depending upon implementation-specific or other considerations, the communication module 1208 may send requests and receive data through a connection (e.g., the communication network 908, and/or the communication link 910), all or a portion of which may be a wireless connection. The communication module 1208 may request and receive messages, and/or other communications from associated systems.

Figure 13:
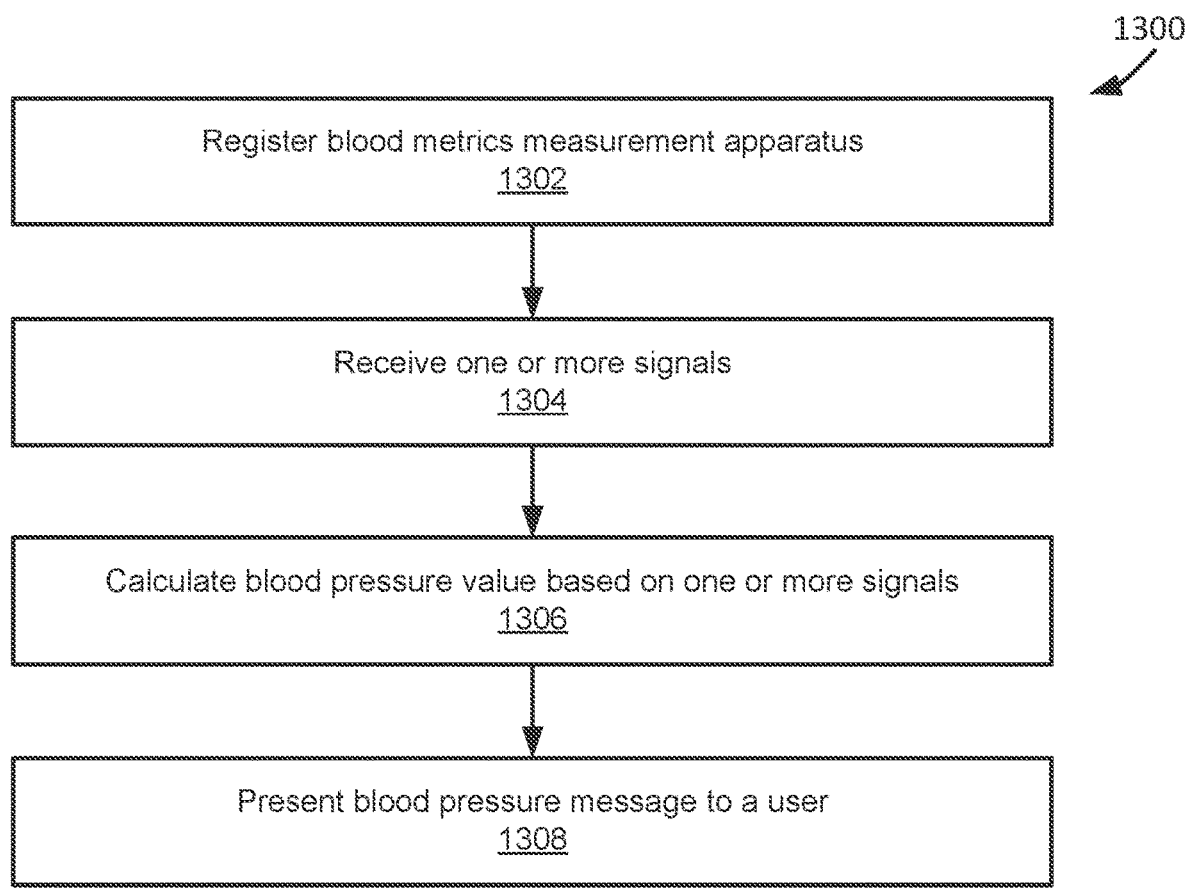
FIG. 13 depicts a flowchart of an example method of operation of a user device according to some embodiments.

FIG. 13 depicts a flowchart 1300 of an example method of operation of a user device (e.g. user device 904) according to some embodiments.

In step 1302, a user device registers a blood metrics measurement apparatus (e.g., blood metrics measurement apparatus 902). In some embodiments, input from a user is received by a user interface module (e.g., user interface module 1202) that triggers a registration module (e.g., registration module 1204) to generate a registration request to associate the blood metrics measurement apparatus with a user and/or the user device. The registration request may include, for example, one or more blood metrics measurement apparatus attributes. In some embodiments, a communication module (e.g., communication module 1208) provides the registration request to a blood metrics server (e.g., blood metrics server 906) for processing.

In step 1304, the user device receives one or more signals from the registered blood metrics measurement apparatus. In some embodiments, the one or more signals comprise optical signals (e.g., multi-channel PPG signals) and/or one or more non-optical signals (e.g., multi-channel pressure pulse signals). In some embodiments, the one or more signals may be received by the communication module.

In step 1306, the user device calculates one or more arterial blood pressure values (e.g., systolic values and/or diastolic values) based on the received one or more signals. In some embodiments, a blood pressure calculation system (e.g., blood pressure calculation system 1206) calculates the one or more arterial blood pressure values. Although this example depicts the user device calculating the one or more arterial blood pressure values, it will be appreciated that one or more other systems having the functionality of a blood pressure calculation system may perform the calculation. For example, in some embodiments, the blood pressure measurement apparatus and/or the blood metrics server may include such functionality and perform the calculation.

In step 1308, the user device presents a blood pressure message to the user based on at least one of the one or more calculated arterial blood pressure values. For example, the message may include some or all of the arterial blood pressure values, alerts (e.g., high BP, low BP, good BP, poor BP, etc.) based on one or more of the calculated values, and so forth. In some embodiments, the user device presents (e.g., via images, audio, vibrations, etc.) the blood pressure message or alert to the user via the user interface module, or other feature of the user device.

Figure 14:
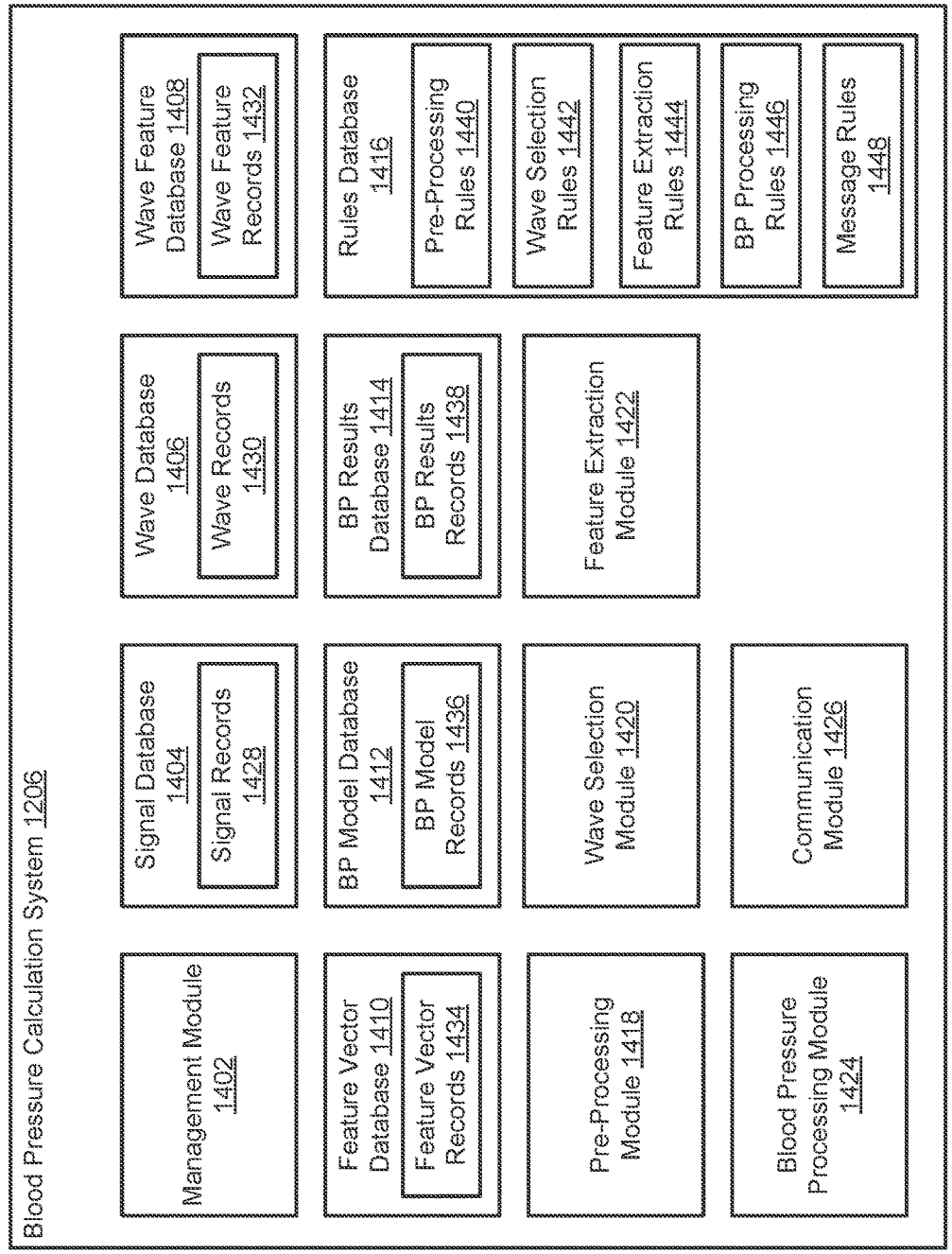
FIG. 14 depicts a block diagram of a blood pressure calculation system according to some embodiments.

FIG. 14 depicts a block diagram 1400 of a blood pressure calculation system 1206 according to some embodiments. Generally, the blood pressure calculation system 1206 may be configured to calculate arterial blood pressure values of a user. The blood pressure calculation system 1206 may also store calculated arterial blood pressure values (e.g., for health tracking, etc.), and communicate with other systems of the system and environment 900. In some embodiments, the blood pressure calculation system 1206 includes a management module 1402, a signal database 1404, a wave database 1406, a wave feature database 1408, a feature vector database 1410, a blood pressure model database 1412, a blood pressure results database 1414, a rules database 1416, a pre-processing module 1418, a wave selection module 1420, a feature extraction module 1422, a blood pressure processing module 1424, and a communication module 1426.

The management module 1402 may be configured to manage (e.g., create, read, update, delete, or access) signal records 1428 stored in the signal database 1404, wave records 1430 stored in the wave database 1406, wave feature records 1432 stored in the wave feature database 1408, feature vector records 1434 stored in the feature vector database 1410, empirical blood pressure model records 1436 stored in the blood pressure model database 1412, blood pressure result records 1438 stored in the blood pressure results database 1414, and/or rules 1440-1448 stored in rules database 1416. The management module 1402 may perform these operations manually (e.g., by an administrator interacting with a GUI) and/or automatically (e.g., by one or more of the modules 1418-1424). In some embodiments, the management module 1402 comprises a library of executable instructions which are executable by a processor for performing any of the aforementioned management operations. The databases 1404-1416 may be any structure and/or structures suitable for storing the records 1428-1438 and/or the rules 1440-1448 (e.g., an active database, a relational database, a table, a matrix, an array, a flat file, and the like).

The signal records 1428 may include a variety of signals, along with associated metadata. For example, the signals may comprise optical signals (e.g., single-channel and/or multi-channel PPG signals) and/or non-optical signals (e.g., pressure pulse signals). In some embodiments, the metadata may include information obtained from the signals, such as heart rate(s) of an associated user. For example, the signal records 1428 may store some or all of the following information:

Signal(s) Identifier: Identifier that identifies the stored signal(s).

Figure 21:
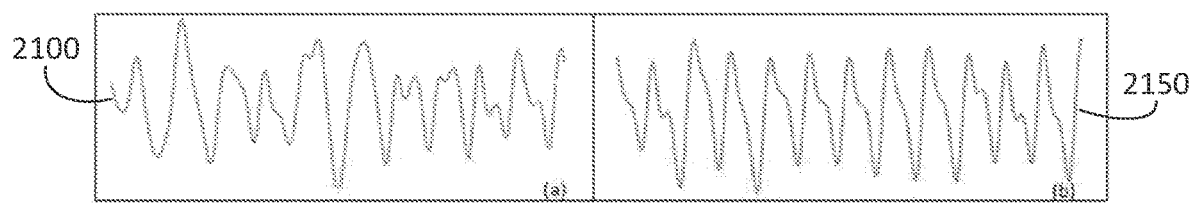
FIG. 21 depicts an example noisy PPG signal and an example filtered PPG signal according to some embodiments.

Signal(s): one or more signals. The signals may be raw signals (e.g., as detected by the associated blood pressure measurement apparatus), filtered or pre-processed signals (e.g., to remove noise from the signals), and/or normalized signal values (e.g., between 0-1). An example "noisy" (i.e., unfiltered) PPG signal and an example filtered PPG signal are shown in FIG. 21. It will be appreciated that as used in this paper, a "signal," such as a PPG signal or pressure pulse signal, generally refers to a filtered signal, although in some embodiments, it may also refer to an unfiltered signal instead of, or in addition to, the filtered signal.

Figure 22:
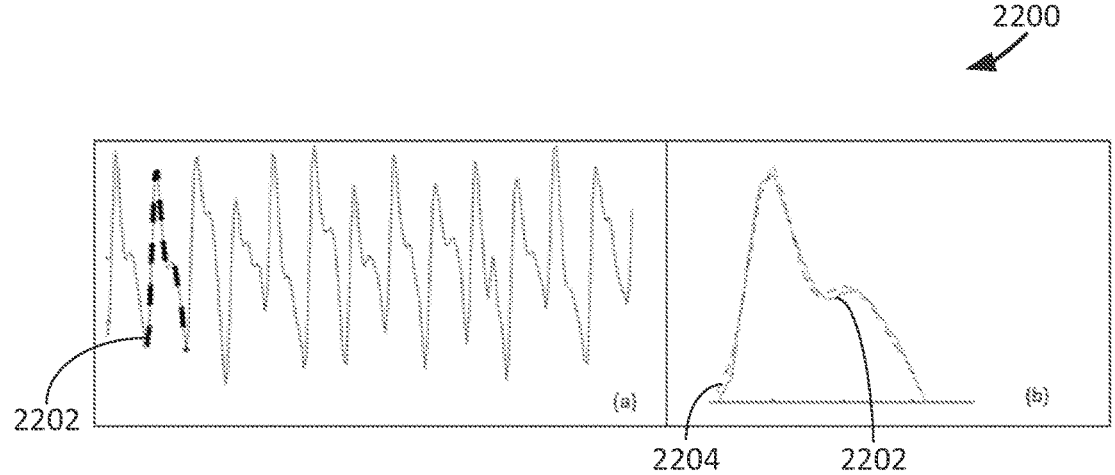
FIG. 22 depicts an example set of waves of a PPG signal and an example high quality wave selected from the set of waves according to some embodiments.

Set(s) of Waves: one or more sets of waves of a predetermined time series (e.g., 8 seconds) of the signal(s). The set of waves may include raw waves, filtered waves, and/or normalized wave values (e.g., between 0-1). An example set of waves is shown in FIG. 22.

Apparatus Identifier: Identifier that identifies the blood metrics measurement apparatus that generated the signals.

User Account Identifier: Identifier that identifies a user account associated with the blood metrics measurement apparatus that generated the signals.

Metadata: Metadata obtained from the signals, such as heart rate or other biometric data. The metadata may also include other information of the user, such as gender, age, height, weight, skin color (e.g., obtained from the user's account information). Such metadata values may be used by the blood pressure calculation module 1424 (discussed below) to facilitate calculation of arterial blood pressure values. In some embodiments, metadata values may be provided to an empirical blood pressure model (discussed below) via sets of feature vectors (discussed below) and/or be provided separately to the model.

The wave records 1430 may include sets of waves of a signal (e.g., a signal stored in the signal database 1404), along with subsets of those waves. The subsets of waves may comprise "high quality" waves obtained from the waves of the signal. These subsets of waves may provide, for example, a more accurate blood pressure calculation that just using the signal or waves of the signal. In some embodiments, the wave records 1430 may store some or all of the following information:

Signal Identifier: Identifier that identifies an associated signal.

Wave Identifier(s): Identifiers for subsets of waves of the associated signal.

Subset(s) of Waves: one or more subsets of waves of the associated signal.

The subsets of waves may include raw waves, filtered waves, and/or normalized wave values (e.g., between 0-1). The subsets of waves may be referred to as "high quality" waves. An example wave of a subset of waves is shown in FIG. 22.

Apparatus Identifier: Identifier that identifies the blood metrics measurement apparatus that generated the signals.

User Account Identifier: Identifier that identifies a user account associated with the blood metrics measurement apparatus that generated the signals.

The wave feature records 1432 may include wave features of associated subsets of waves of a signal. For example, wave features may include wave peaks, wave valleys, wave edges, and/or the like. In some embodiments, the wave feature records 1432 may store some or all of the following information:

Signal Identifier: Identifier that identifies an associated signal.

Wave Identifier(s): Identifiers for the subsets of waves of the associated signal.

Figures 23, 24:
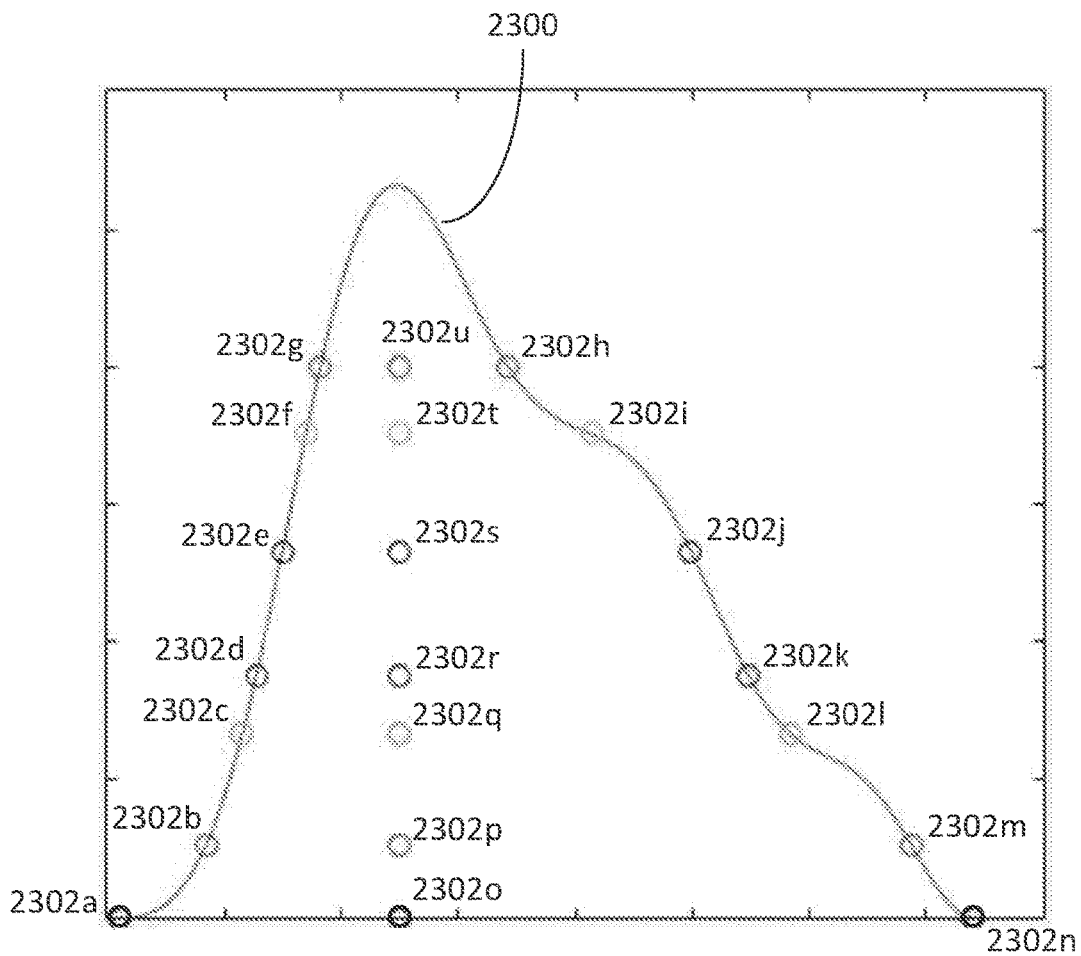
FIG. 23 depicts example feature points of a wave according to some embodiments.
FIG. 24 depicts an example feature vector according to some embodiments.

Wave Features: one or more features obtained from the waves within the associated subsets of waves. The wave features may include points of the waves, such as wave peaks, wave valleys, wave edges, and/or the like. The wave features may be stored as normalized wave values (e.g., between 0-1). Example wave features are shown in FIG. 23, and discussed elsewhere herein.

Apparatus Identifier: Identifier that identifies the blood metrics measurement apparatus that generated the signals.

User Account Identifier: Identifier that identifies a user account associated with the blood metrics measurement apparatus that generated the signals.

The feature vector records 1434 may include sets of features generated based on the wave features of associated subsets of waves of a signal. In some embodiments, the feature vector records 1434 may store some or all of the following information:

Signal Identifier: Identifier that identifies an associated signal.

Wave Identifier(s): Identifiers for the subsets of waves of the associated signal.

Set(s) of Feature Vectors: one or more sets of feature vectors, each feature vector comprising features extracted from a wave of an associated subset of waves. The values of a feature vector may include measurement values and metric values. For example, the measurement values may correspond to amplitude or location points of a particular wave, and the metric values may be generated from metric functions that use at least one of the measurement values. The values of a feature vector may comprise normalized values (e.g., between 0-1). An example feature vector 2400 is shown in FIG. 24.

Apparatus Identifier: Identifier that identifies the blood metrics measurement apparatus that generated the signals.

User Account Identifier: Identifier that identifies a user account associated with the blood metrics measurement apparatus that generated the signals.

The blood pressure model records 1436 may include one or more empirical blood pressure models (e.g., retrieved from the blood metrics server 906). The models may include various types of empirical blood pressure models. For example, a first type may be a "non-specific" model which does not require calibration in order to be used to calculate arterial blood pressure values. A second type may be a "specific" model which requires calibration in order to be used to calculate arterial blood pressure values. For example, models of the second type may require information about the user, such age, weight, height, gender, skin color, and/or the like. In some embodiments, the blood pressure records 1436 may store some or all of the following information:

Model Identifier: Identifies an empirical blood pressure model.

Model Type: Identifies a type of model (e.g., non-specific or specific).

Figure 26:
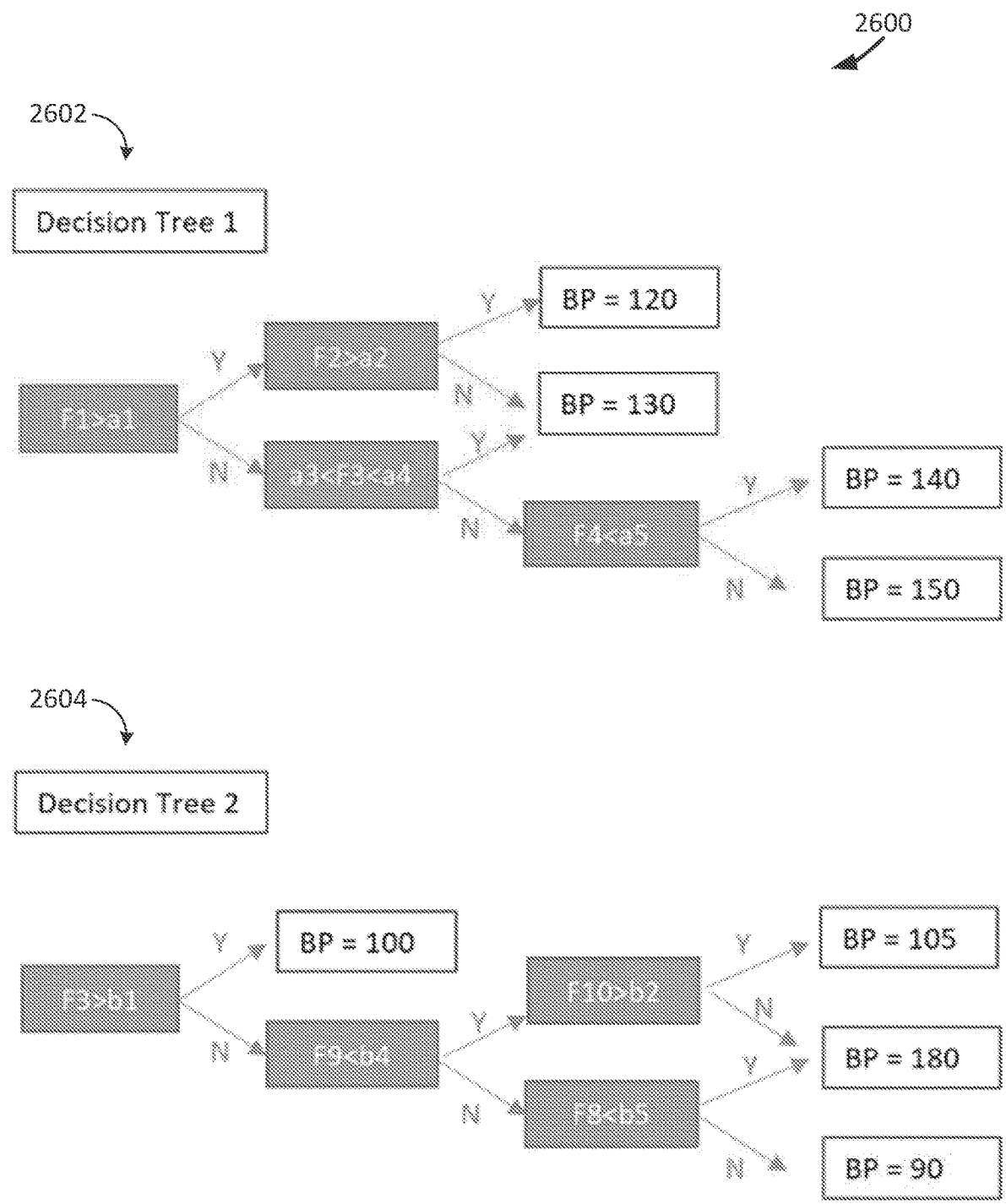
FIG. 26 depicts example tree structures of an example empirical blood pressure calculation model according to some embodiments.

Model Parameters: Various model parameters (e.g., decision node parameters) and tree structures used to calculate the arterial blood pressure values based on the sets of feature vectors and/or other related information (e.g., gender, age, weight, height, skin color, etc.). Example tree structures are shown in FIG. 26.

Apparatus Identifier(s): Identifier(s) that identify one or more blood metrics measurement apparatus' using the empirical blood pressure model.

User Account Identifier(s): Identifier(s) that identify one or more user account(s) associated with the blood metrics measurement apparatus that use the empirical blood pressure model.

The blood pressure results records 1438 may include one or more calculated arterial blood pressure values. In some embodiments, the blood pressure results records 1438 may store some or all of the following information:

Blood Pressure Result Identifier: Identifies a set of one or more calculated arterial blood pressure values.

Blood Pressure Values: one or more calculated arterial blood pressure values.

Date: A date and/or time the arterial blood pressure was calculated.

Messages: Message identifier and/or messages generated based on the calculated blood pressure values.

Signal Identifier: Identifier that identifies an associated signal.

Wave Identifier(s): Identifiers for the subsets of waves of the associated signal.

Feature Vectors Identifier(s): Identifiers for the one or more sets of feature vectors used to calculate the arterial blood pressure values.

Apparatus Identifier: Identifier that identifies the blood metrics measurement apparatus that generated the signals.

User Account Identifier: Identifier that identifies a user account associated with the blood metrics measurement apparatus that generated the signals.

Pre-Processing Rules 1440

The pre-processing rules 1440 define attributes and/or functions for filtering signals. For example, a signal may be corrupted with noise from various sources (e.g., high frequency ambient noise, electronic noise, and the like). In some embodiments, the signal may be the raw signal data from a photodiode, output of a pressure sensor, output of an accelerometer, output of a gyroscope, and the like. The signal may be filtered to remove corrupting noise, as well as enhance a strength of the signal.

The pre-processing module 1418 may be configured to execute the pre-processing rules 1440. Thus, for example, the pre-processing module 1418, using some or all of the associated signals and/or values stored in the signal records 1428, may filter signals and store the resulting filtered signals. The wave database 1406 may be configured to store the signals filtered by the pre-processing module 1418.

Wave Selection Rules 1442

The wave selection rules 1442 define attributes and/or functions for selecting (or, "extracting") high quality waves from a set of waves of a signal. The high quality waves may form a subset of waves.

In some embodiments, signal measurements are sensitive to motion, pressure, and ambient light distortions. Noise-removal filters may not be entirely effective when there is intense noise. It may be helpful to select high quality signal waves from measured time-series data to reduce or eliminate the effects of motion, pressure, and/or ambient light distortions.

In some embodiments, the wave selection rules 1442 identifies candidate waves from a signal, and determines whether any of the candidate waves satisfy a model match criterion (e.g., a Gaussian mixture model or group similarity model). Candidate waves that pass the model match criterion may be classified as high quality waves. In some embodiments, candidate waves includes waves having valleys whose frequency match, or substantially match, the heart rate of the user or other heart rate value (e.g. a default heart rate value).

Figure 28:
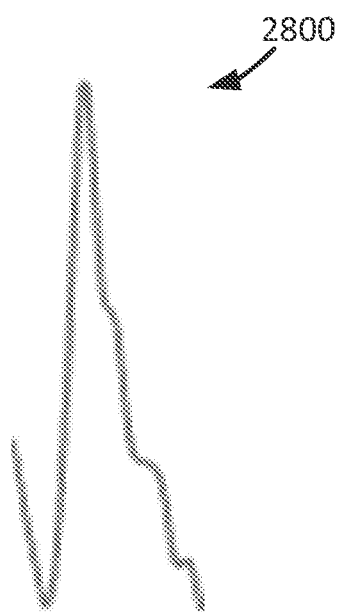
FIG. 28 depicts an example PPG signal including multiple reflections according to some embodiments.

A group similarity model may be preferable. For example, while a Gaussian mixture model may perform well with "smoothed" signals (e.g., low pass filtered at 4-6 Hz), the Gaussian mixture model may fail, or perform poorly, if the signal includes more features. FIG. 22 depicts an example smoothed signal 2202, and FIG. 28 depicts an example signal including more features (e.g., low pass filtered at 10 Hz revealing multiple reflections including, for example, secondary peaks, such as iliac and renal reflections). In some embodiments, the Gaussian mixture model may be unable to match more than 2 peak results in a reflection of waves that reveal features critical in the prediction (or, "estimation) of blood pressure. In some embodiments, additional Gaussian mixture models may be incorporated to address such issues, although this may lead to added complexity in optimization (e.g., model fitting), as well as added constraints to ensure specificity to physiologically meaningful signals against noise.

In some embodiments, a group similarity model may overcome some or all of the limitations described above. Generally, high quality (or high fidelity) waves that correspond with arterial blood flow corresponding to a single cycle typically occur in groups. In cases where there is motion, it may be unlikely that an individual wave would have a high quality when waves before it were not of high quality. In the group similarity model, candidate waves may be individually matched to an existing wave buffer (e.g., of the wave database 1406). In some embodiments, the wave buffer may include some or all previous candidates waves added in succession in a first in first out (FIFO) method. The size of the wave buffer may be set to include a predetermined number of waves (e.g., 15 waves), and may be altered. For example, increasing the wave buffer to include additional candidate waves may require that candidate waves match a larger set of previously extracted candidate waves. In some embodiments, in order to measure similarity, the candidate waves may be re-parameterized to a fixed length (e.g., using a cubic spline).

In various embodiments, the group similarity model applies a similarity measure to determine if, and to what extent, a candidate wave matches some or all of the existing waves in the wave buffer. In one example, the similarity measure may be an average correlation between the candidate wave and the individual waves in the wave buffer. In other embodiments, the similarity measure may include a like sum of squared differences, joint entropy or mutual information, and the like. In this example, if the similarity measure is greater than a threshold (e.g. 0.95 for correlation), this wave is selected for further processing. In some embodiments, both the candidate waves that are selected for further processing and the candidate waves that are not selected for further processing may be added to the wave buffer (e.g., for subsequent applications of the group similarity model).

The group similarity model may process waves with multiple reflections (e.g., as depicted in FIG. 28). In some embodiments, the group similarity model may continuously update a template (e.g., the wave buffer) against which incoming candidate waves are matched, and that template may indicate the true underlying signal, which may be different from user to user, instead of relying on a predetermined template. The group similarity model may reduce false positive identification of candidate waves relative to other models (e.g., Gaussian mixture model).

The wave selection module 1420 may be configured to execute the wave selection rules 1442. Thus, for example, the wave selection module 1420, using some or all of the associated waves and/or values stored in the signal records 1428, may identify one or more subsets of "high quality" waves. The wave database 1406 may be configured to store the subsets of waves identified by the wave selection module 1420. An example result of execution of the wave selection rules 1442 is shown in FIG. 22.

Feature Extraction Rules 1444

The feature extraction rules 1444 define attributes and/or functions for identifying (or, "extracting") features from waves (e.g., high quality waves). In some embodiments, features may be concatenated to form feature vectors.

Features may include, but are not limited to, pulse transit time (PTT) features, reflection features, signal level and range features, signal metric features, optical ratio features, heart rate features, wave width and derivative features, user information features, and/or pressure features. In some embodiments, PTT features include a transit time feature, joint entropy feature, and wave type feature. Pulse transit time may be measured as the time taken for the pulse pressure wave to propagate along the length of the arterial tree. For example, this may be the difference in time between the onset of the R-wave on ECG, and the pulse wave peak on the finger. In other embodiments, the transit time may be measured as the time taken for blood to travel from one LED-PD system to another LED-PD system (e.g., as depicted in FIG. 10B), which may be separated from each other by a predetermined distance (e.g., 15 mm). Sampling at a very high rate (>2 KHz) may help resolve features in both LED-PD systems. In some embodiments, the transit time may be measured as (1) the distance between the valleys in the corresponding waves in respective LED-PD systems at the start of the systolic cycle, and/or (2) the distance between the peaks in first derivatives between the two LED-PD systems. The transit time may be expressed in any units (e.g., milliseconds).

The joint entropy feature may be a measurement of similarity between fast channels of respective LED-PD systems. High pulse pressure may correlate with low entropy or high mutual information shared between the fast LED channels. The joint entropy feature may be expressed in bytes.

Wave type features may include different types of waves. For example, different types of waves may include slow type waves and fast type waves. In some embodiments, the wave types feature quantifies the relative position of the systolic peak within the wave (0<WaveType<1) for each of the fast channels in respective LED-PD systems, where small values correspond to a slow type waves and larger values correspond to fast type waves.

A pulse decomposition may track a pulse pressure wave. As the pressure wave travels in the arterial systems, it may encounter branching points where the diameter of arteries may decrease rapidly. The pressure wave may bounce on such branching points and send reflection waves in different (e.g., opposite) directions. In some embodiments, the original pressure wave plus the reflections may form the observed pressure pulse, which in turn may be observed in a signal (e.g., PPG signal). Multiple reflections (e.g., four reflections) may be used to identify multiple features and amplitudes (e.g., four features and four amplitudes). The time of occurrence of the systolic peak from the start of the systolic cycle (i.e., systolic peak time) may also be included as a feature. In some embodiments, a ratio between the second derivatives at the bottom and peak of the systolic cycle may be used as a feature. This feature may be correlated with arterial stiffness. In some embodiments, ten features may be individually identified for each LED channel.

The signal level and range features may comprise the mean value and range of a signal (e.g., PPG signal) determined for each of the channels. In some embodiments, the signal metrics features include Hjorth parameters, perfusion, kurtosis, and energy features. Hjorth parameters may describe activity, mobility and complexity of the signal, and are commonly used tools in EEG analysis. Perfusion may be measured as the ratio between the AC and DC components of the signal (i.e. the range of the signal and the mean). Kurtosis may be measured over the signal analysis window. Energy features may include variance of the signal measured over the analysis window. In some embodiments, optical ratio features may be calculated as the ratio of the range of the LEDs (measured in pairs across wavelengths) after normalization of the respective signals, and heart rate features may be an actual user heart rate or a default heart rate.

Figure 25A:
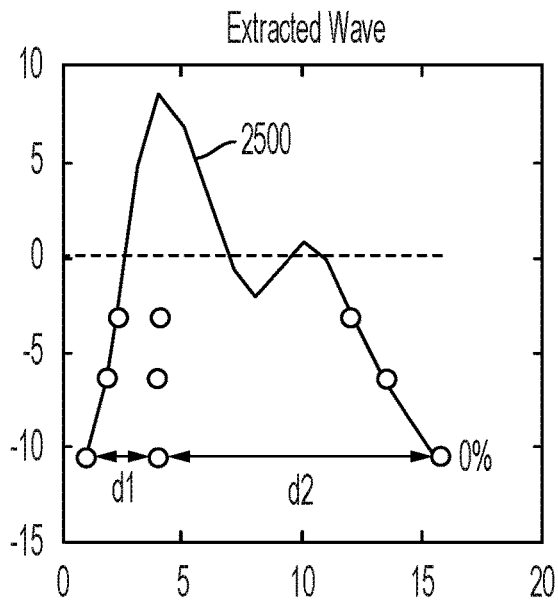
FIGS. 25A-C show an example selected high quality wave, the first derivative of the selected high quality wave, and the second derivative of the selected high quality wave according to some embodiments.

In some embodiments, the wave width and derivative features may include time distances within a wave to its main peak at different amplitude locations. One example is shown in FIG. 25A for 0% amplitude location. In FIG. 25A, d1 and d2 represent the distance between the rising (falling) edge value of the wave and its main (systolic) peak. The secondary (diastolic) peak may be extracted from the first order derivative (FOD) of the wave. For this, FOD may be smoothed (e.g., a simple moving average filter may be used). In some embodiments, after extracting main (systolic) and secondary (diastolic) peaks, reflection (augmentation) index (the ratio of diastolic peak and systolic peak amplitudes), inflection point area ratio (the ratio of areas under the wave that are separated by the diastolic inflection point), and/or stiffness index (the ratio of patient's height to the time distance between the systolic and diastolic peaks) may be determined from the first order derivative of the wave.

Figure 25B:
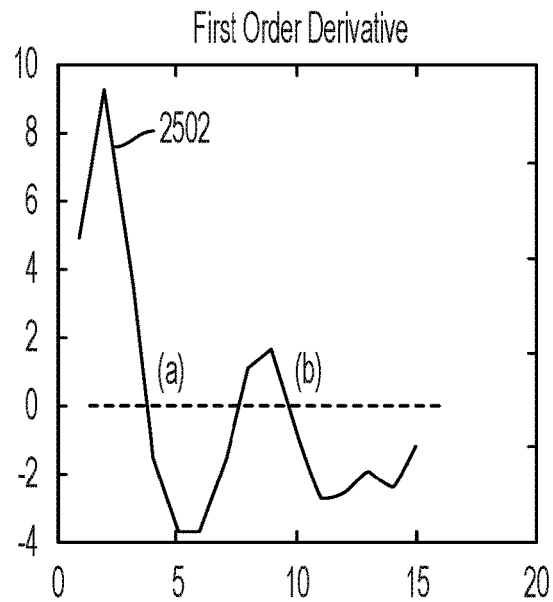
Figure 25C:
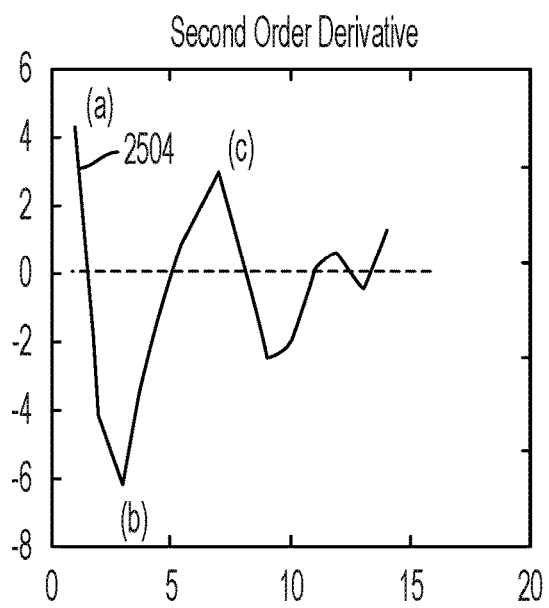

In the example of FIG. 25C, the second order derivative of the wave has multiple peaks and valley points (e.g., labeled (a), (b) and (e)). In some embodiments additional peak and valleys may be present. If the sampling frequency is low or under exercise conditions (e.g., about 25 Hz in FIG. 25C), only waves (a), (b) and (e) may be identifiable. In some embodiments, for higher sampling frequencies (e.g., >200 Hz), additional peaks and valleys may be identifiable. The ratio of these values may be included into a feature vector.

As indicated, an example selected (or, extracted) wave, first order derivative of the selected wave, and the second derivative of the selected wave are shown in FIGS. 25A-C, respectively.

In some embodiments, if two LEDs at the same wavelength are positioned at different locations of the same artery, a phase shift may be obtained between the measured signals (e.g., due to blood flow). This may facilitate calculation of pulse wave velocity (PWV) and/or pulse transit time (PTT), both of which may be included in a feature vector, and/or otherwise provided to the empirical blood pressure model used to calculate arterial blood pressure values.

The user information features may include, for example, a user's gender, age, skin color, height and/or weight. The user information may be included in a feature vector, and/or otherwise provided to the empirical blood pressure model used to calculate arterial blood pressure values. In some embodiments, pressure features may include the mean value of the pressure signal over the analysis window (or "baseline mean") and range of the pressure signal over the analysis window (or, "AC").

The feature extraction module 1422 may be configured to execute the feature extraction rules 1444. Thus, for example, the feature extraction module 1420, using some or all of the associated subsets of waves and/or values stored in the wave records 1430, may identify one or more feature of the waves within the subsets of waves, and generate corresponding sets of feature vectors. An example of a feature vector 2400 is shown in FIG. 24. The wave feature database 1408 may be configured to store the wave features identified by the feature extraction module 1422, and the feature vector database 1410 may be configured to store the generated sets of feature vectors.

Blood Pressure Processing Rules 1446

The blood pressure processing rules 1446 define attributes and/or functions for calculating arterial blood pressure values of a user. In some embodiments, the blood pressure processing rules 1446 specify, identify, and/or define the empirical blood pressure model to use for calculating arterial blood pressure of a user. The rules 1446 may further define input values for the empirical blood pressure model. For example, input values may comprises the sets of features vectors, and/or other attributes of the user (e.g., age, gender, height, weight, skin color, etc.), assuming such attributes have not been included in the feature vectors.

The blood pressure processing module 1424 may be configured to execute the blood pressure processing rules 1446. Thus, for example, the blood pressure processing module 1424, using an empirical blood pressure model stored in the blood pressure model database 1412, along with some or all of the associated sets of feature vectors and/or values stored in the feature vector records 1438, may calculate one or more arterial blood pressure values. The blood pressure results database 1414 may be configured to store the blood pressure values calculated by the blood pressure processing module 1424.

Message Rules 1448

The message rules 1448 define attributes and/or functions for generating messages and/or alerts based on arterial blood pressure values. In some embodiments, the message rules 1448 may define rules that cause the blood pressure calculation system 1206 to provide calculate blood pressure values to a user. In some embodiments, the message rules 1448 may include threshold values and/or conditions that when exceeded and/or satisfied, trigger a message or alert. For example, a threshold value (or value range) and/or threshold condition may be associated with varying blood pressure levels (e.g., hypotension, normal blood pressure, prehypertension, stage 1 hypertension, stage 2 hypertension, etc.), and a calculated blood pressure value which satisfies a corresponding threshold condition or value may trigger a message or alert (e.g., indicating the corresponding blood pressure level).

In some embodiments, the communication module 1426 may be configured to execute the message rules 1448. Thus, for example, the communication module 1420, using some or all of the blood pressure values stored in the blood pressure results records 1438, may generate one or more messages. The communication module 1426 may be configured to provide those messages to a user.

In some embodiments, the communication module 1426 may be configured to send requests to and receive data from one or a plurality of systems. The communication module 1426 may send requests to and receive data from a systems through a network or a portion of a network. Depending upon implementation-specific or other considerations, the communication module 1426 may send requests and receive data through a connection (e.g., the communication network 908, and/or the communication link 910), all or a portion of which may be a wireless connection. The communication module 1426 may request and receive messages, and/or other communications from associated systems.

Figure 15A:
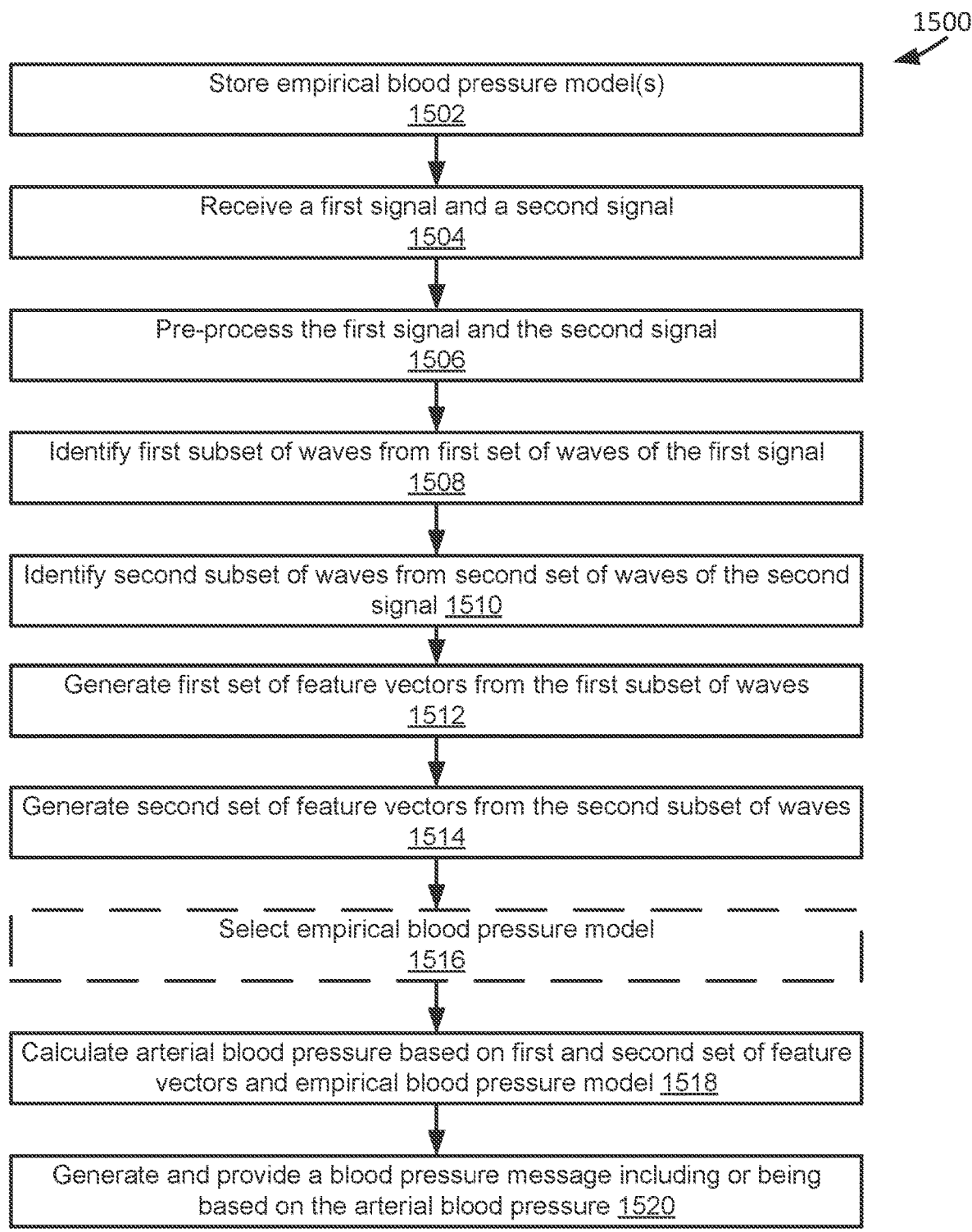
FIG. 15A depicts a flowchart of an example method of operation of a blood pressure calculation system according to some embodiments.

FIG. 15A depicts a flowchart 1500 of an example method of operation of a blood pressure calculation system (e.g., blood pressure calculation system 1206) according to some embodiments.

In step 1502, the blood pressure calculation system stores one or more empirical blood pressure models. For example, the one or more empirical blood pressure models may be received from a blood metrics server (e.g., blood metrics server 906), and may comprise specific or non-specific empirical blood pressure models. In some embodiments, a management module (e.g., management module 1402) stores the one or more empirical blood pressure models in a blood pressure model database (e.g., blood pressure results database 1414), and/or a communication module (e.g., communication module 1426) receives the one or more empirical blood pressure models.

In step 1504, the blood pressure calculation system receives a first signal (e.g., a single-channel or multi-channel PPG signal) and a second signal (e.g., a single-channel or multi-channel PPG signal). For example, the first signal may comprise a 7-channel PPG signal generated from light energy emitted at seven different wavelengths (e.g., 523 nm, 590 nm, 623 nm, 660 nm, 740 nm, 850 nm, 940 nm) from one or more light sources (e.g., seven different LEDs), and the second signal may comprise a PPG signal generated from light energy generated from an additional light source (e.g., LED) at the same, or substantially similar, wavelength as one the wavelengths of the first signal. Using multi-channel signals and/or different light sources may help ensure, for example, that good quality signals may be obtained in a variety of circumstances (e.g., a user moving, walking, running, sleeping, and so forth). By way of further example, the first and/or second signals may comprise a pressure pulse signal. In some embodiments, a communication module communication module (e.g., communication module 1426 and/or communication module 1208) receives the first and second signals from a blood metrics measurement apparatus (e.g., blood metrics measurement apparatus 902).

In step 1504, the blood pressure calculation system pre-processes (or, filters) the first and second signals. In some embodiments, a pre-processing module executes pre-processing rules to filter the first and second signals. An example filtering method is shown and described with reference to FIG. 15B.

In steps 1508-1510, the blood pressure calculation system identifies a first subset of waves (or, "high quality" waves) from a first set of waves of the first signal and a second subset of waves (or, "high quality" waves) from a second set of waves of the second signal. Each of the first subset of waves may represent a separate approximation of an average of the first set of waves over a first predetermined amount of time (e.g., 8 seconds). Similarly, each of the second subset of waves may represent a separate approximation of an average of the second set of waves over a second predetermined amount of time (e.g., 8 seconds). In some embodiments, the first and second predetermined amounts of time may be the same or they may be different. In some embodiments, a wave selection module (e.g., wave selection module 1420) identifies the subsets of waves.

In steps 1512-1514, the blood pressure calculation system generates a first set of feature vectors and a second set of feature vectors. The first set of feature vectors may be generated from the first subset of waves, and the second set of feature vectors may be generated from the second subset of waves. Each of the feature vectors may include measurement values and/or metric values. For example, the measurement values may correspond to amplitude (e.g., peak-to-peak amplitude, peak amplitude, semi-amplitude, root mean square amplitude, pulse amplitude, etc.) and/or location points of a particular wave (e.g., a corresponding high quality wave), and the metric values may be generated from metric functions that use at least one of the measurement values. In some embodiments, a feature extraction module (e.g., feature extraction module 1420) generates the sets of feature vectors.

In some embodiments, measurement values may include wave peak locations and/or amplitudes, wave valley locations and/or amplitudes, a wave's first or higher order derivative peak locations and/or amplitudes, a wave's first or higher order derivative valley locations and/or amplitudes, and/or or first or higher order moments of a wave. In various embodiments, the metric functions may include one or more particular metric functions that calculate a distance between a plurality of measurement values. For example, a metric function may calculate a distance between location points of a particular wave (e.g., a particular wave peak and a particular wave valley).

In step 1516, the blood pressure calculation system may select an empirical blood pressure model. For example, the blood pressure calculation system may select an empirical blood pressure model from the one or more empirical blood pressure models stored in the blood pressure model database. In some embodiments, a blood pressure processing module (e.g., blood pressure processing module 1422) selects the empirical blood pressure model.

In some embodiments, the blood pressure calculation system may operate in different modes. For example, in a first mode of operation, the blood pressure calculation system may utilize a non-specific type of empirical blood pressure model which does not require further calibration in order to be used to calculation arterial blood pressure values. Accordingly, in such a first mode of operation, selecting the empirical blood pressure model may comprise selecting the non-specific empirical blood pressure model from the empirical blood pressure models stored in the blood pressure database. To continue the example, in a second mode of operation, the blood pressure calculation system may utilize a specific type of empirical blood pressure model which requires at least some calibration prior to being used to calculate arterial blood pressure values. In such a second mode of operation, selecting an empirical blood pressure model may comprise selecting an empirical blood pressure model from the one or more blood pressure models stored in the blood pressure based on one or more attributes of the user (e.g., gender, weight, height, skin color, and/or age) and/or other parameters. In some embodiments, a blood pressure processing module (e.g., blood pressure processing module 1422) selects the empirical blood pressure model.

In step 1518, the blood pressure calculation system calculates one or more arterial blood pressure values based on the first set of feature vectors, the second set of feature vectors, and an empirical blood pressure calculation model (e.g., the model selected in step 1516). For example, the empirical blood pressure calculation model may be configured to receive the first set of feature vectors and the second set of feature vectors as input values. In some embodiments, the blood pressure processing module calculates the one or more arterial blood pressure values.

In step 1520, the blood pressure calculation system may generate and/or provide a message including or being based on the arterial blood pressure. In some embodiments, the communication module generates and/or provides the message to a user.

Figure 15B:
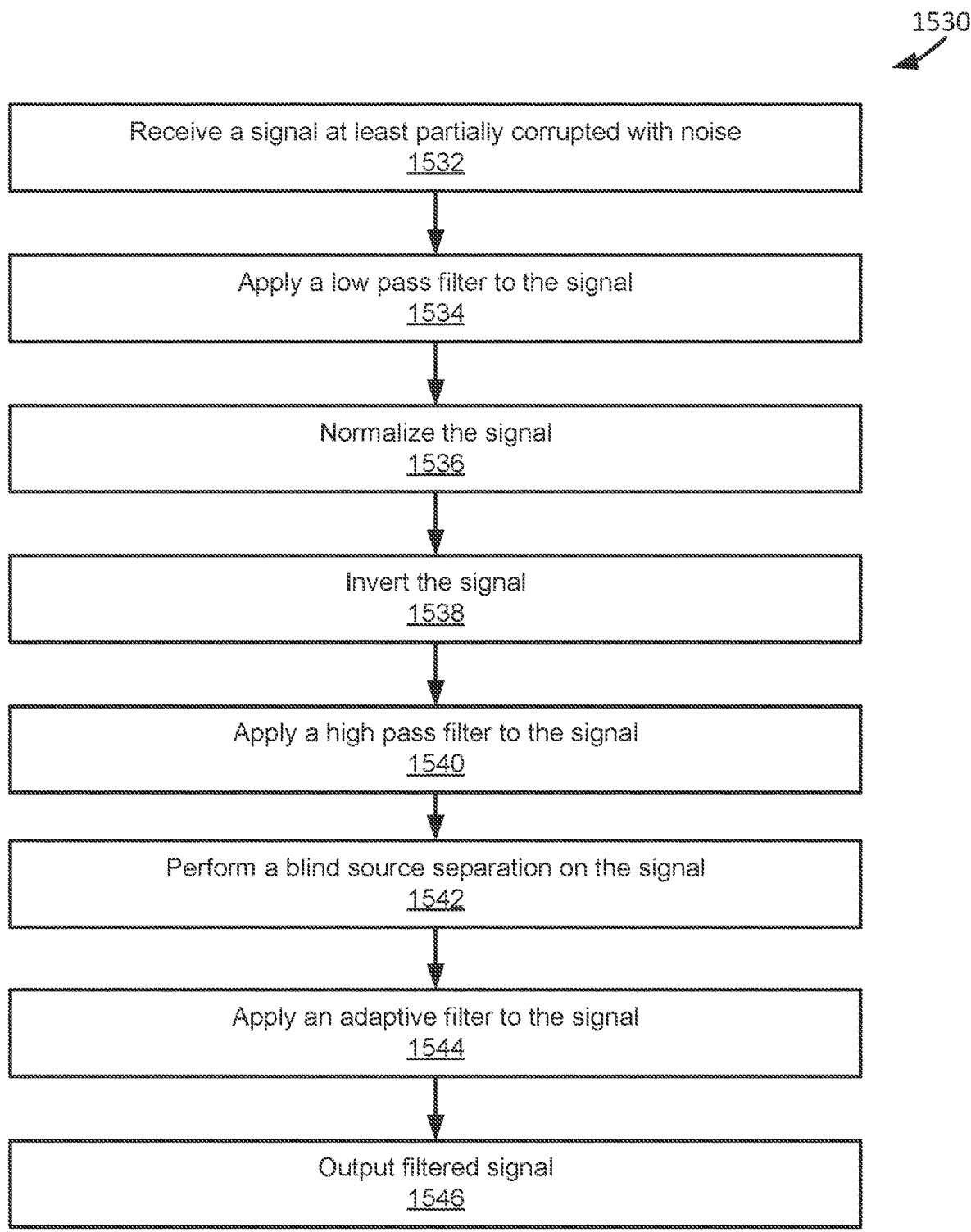
FIG. 15B depicts a flowchart of an example method of pre-processing (or, "filtering") a signal according to some embodiments.

FIG. 15B depicts a flowchart 1530 of an example method of pre-processing (or, "filtering") a signal according to some embodiments. Although only one signal is discussed here, it will be appreciated that multiple signals may be filtered (e.g., simultaneously) using some or all of the steps described below.

In step 1532, a blood pressure calculation system 1206 receives a signal at least partially corrupted with noise (or, a "noisy" signal). For example, the signal may be an output from a photodiode, a pressure sensor, an accelerometer, a gyroscope, or the like. The noise may include one or more types of noise, such as high frequency ambient noise, electronic noise, and so forth. For example, the noise may be motion-related noise associated with venous blood movement, changes in sensor coupling with the tissue of the user, and so forth. In some embodiments, a communication module (e.g., communication module 1426) receives the signal from a blood metrics measurement apparatus.

In step 1534, the blood pressure calculation system 1206 generates and/or applies a low pass filter to the signal. For example, the blood pressure calculation system 1206 may apply a finite impulse response (FIR) low pass filter with a predetermined cut off frequency (e.g., 10 Hz) or frequency range (e.g., 6 Hz-12 Hz). In some embodiments, the low pass filter may be configured to pass signals having a frequency lower than the predetermined cut off frequency, and/or configured to attenuate signals having frequencies higher than the cutoff frequency. In some embodiments, a pre-processing module applies the low pass filter.

In step 1536, the blood pressure calculation system 1206 normalizes the sign. For example, the blood pressure calculation system may normalizes the signal by subtracting and dividing by the mean (DC) value of the signal. In some embodiments, the pre-processing module 1418 normalizes the signal.

In step 1538, the blood pressure calculation system 1206 inverts the signal. For example, the blood pressure calculation system may invert the signal such that an increasing in amplitude corresponds with an increase in volume in the arteries. In some embodiments, the pre-processing module 1418 inverts the signal.

In step 1540, the blood pressure calculation system 1206 applies a high pass filter to the signal. In some embodiments, the high pass filter may be configured to pass signals having a frequency higher than a certain cutoff frequency, and/or configured to attenuate signals having frequencies lower than the cutoff frequency. For example, the high pass filter may be an FIR filter having a predetermined cut off frequency (e.g., 0.6 Hz). In another example, the high pass filter may be a Savitzksy-Golay filter configured to remove low frequency fluctuations arising from respiration rate.

In step 1542, the blood pressure calculation system 1206 performs a blind source separation on the signal to isolate signals associated with arteries from the venous pulsations. In some embodiments, this step does not apply to non-optical signals. In various embodiments, signals may typically contain both venous and arterial components to varying degrees, and signal data collected from a channel may be dependent on the position on the tissue of a user where the data is collected, as well as the wavelength of the light source, which may have an effect on the depth of penetration of that light wavelength into tissue, as well as scattering. If a channel is composed of two independent components (e.g., arterial and venous signals), the components may be isolated by using multiple channels using independent component analysis. In some embodiments, the pre-processing module performs the blind source separation.

In step 1544, the blood pressure calculation system 1206 generates and/or applies an adaptive filter to the signal. In some embodiments, the adaptive filter removes noise from the signal using one or more other signals that may be related to the noise as a noise reference. For example, the adaptive filter may be configured to remove motion related noise from the signal using an accelerometer signal as a noise reference. In some embodiments, motion information may be captured by an accelerometer along three axis (e.g., x, y, and z-axis). Motion along each access may be captured by a component of the accelerometer. In various embodiments, the blood pressure calculation system calculates a sum of the three accelerometer components, and uses the sum as a noise reference. Alternately, the blood pressure calculation system 1206 may determine the largest varying component and uses that component as the reference. In some embodiments, the blood pressure calculation system may use each component successively to form three adaptive filters in sequence. In some embodiments, the pre-processing module generates and/or applies the adaptive filter.

In step 1546, the blood pressure calculation system 1206 outputs a filtered signal (i.e., the signal filtered by some or all of the steps 1532-1544). In some embodiments, the pre-processing module 1418 outputs the filtered signal.

Figure 15C:
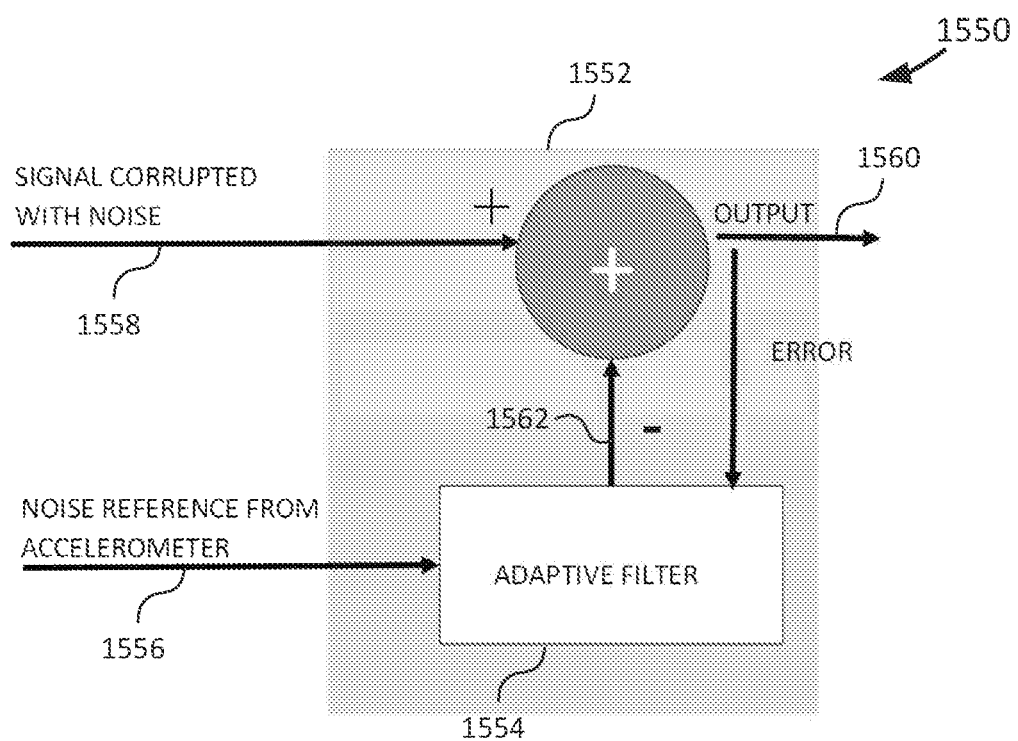
FIG. 15C depicts a blocks diagram of an example pre-processing system for filtering signals according to some embodiments.

FIG. 15C depicts a blocks diagram 1550 of an example filtering system 1552 for filtering signals according to some embodiments. The filtering system 1552 includes an adaptive filter 1554 that may be continuously updated. The adaptive filter 1554 may be dynamically modified such that its convolution with the noise reference 1556 creates a noise component that is maximally similar to the motion related noise in the signal 1558 corrupted with motion noise. The filtering system 1552 may be configured to optimize the adaptive filter 1552 to minimize the output signal 1560 from the adaptive filter 1552. For example, the output signal 1560 may be minimal when a filtered version 1562 of the noise reference 1556 has removed a threshold portion (e.g., greater than 80%) of the corresponding noise present in the noise-corrupted signal 1558. Various minimization methods may be used (e.g., recursive least square minimization) to produce the minimized output signal 1560.

Figure 16A:
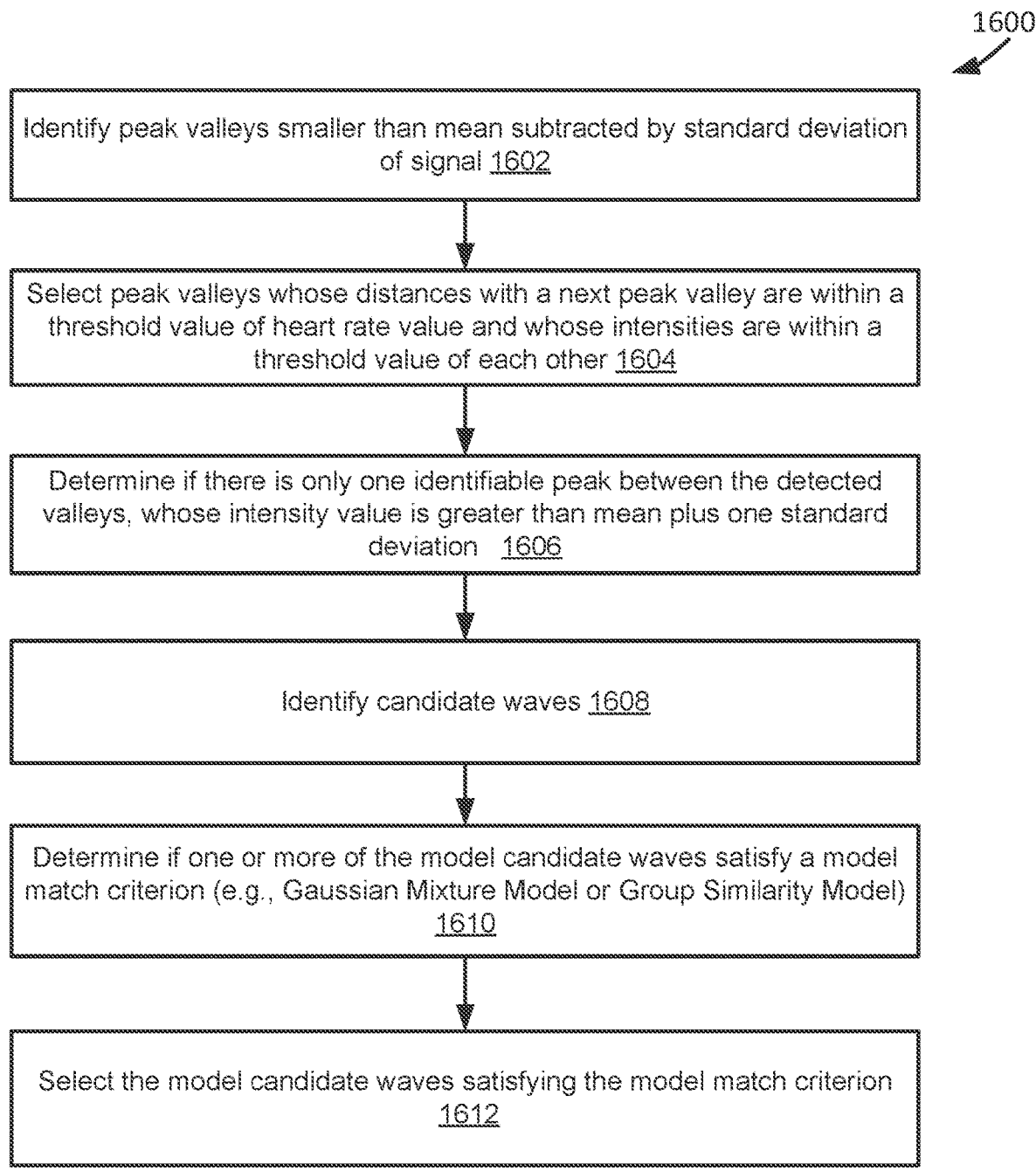
FIG. 16A depicts a flowchart of an example method for extracting high quality waves according to some embodiments.

FIG. 16A depicts a flowchart 1600 of an example method for extracting high quality waves according to some embodiments. For example, some or all of the following steps may be applied to a segment (e.g., an 8 second segment or 12 second segment) of each channel of a multi-channel signal to identify subsets of waves of the multi-channel signal.

In step 1602, the blood pressure calculation system (e.g., blood pressure calculating system 1206) identifies peak values smaller (or, less) than a mean subtracted by a standard deviation of the signal. In some embodiments, a wave selection module performs the identification.

In step 1604, the blood pressure calculation system selects peak valleys whose distances with a next peak valley are within a threshold value (e.g., 5%) of a heart rate value and whose intensities are within a threshold value (e.g., 5%) of each other. In some embodiments, the wave selection module performs the selection.

In step 1606, the blood pressure calculation system determines whether there is only one identifiable peak between the detected valleys, whose intensity value is greater than a mean plus one standard deviation. In some embodiments, the wave selection module performs the determination.

In step 1608, the blood pressure calculation system identifies one or more candidate waves. For example, the one or more candidate waves may be identified from steps 1602-1606. As used herein, it will be appreciated that candidate waves may also be referred to as "model candidate waves." In some embodiments, the wave selection module performs the identification.

Figure 16B:
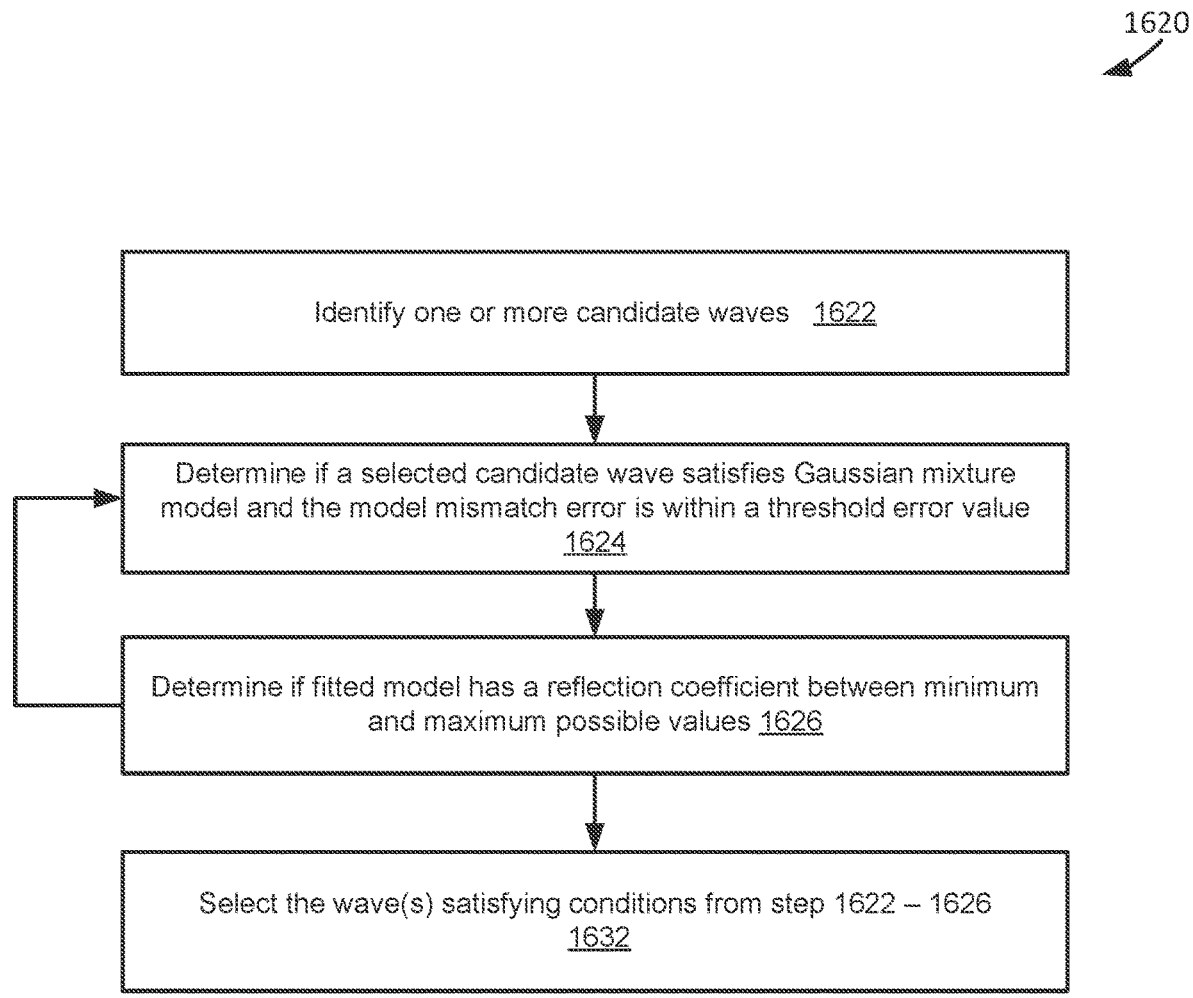
FIG. 16B depicts a flowchart of an example method for extracting high quality waves using a Gaussian mixture model according to some embodiments.
Figure 16C:
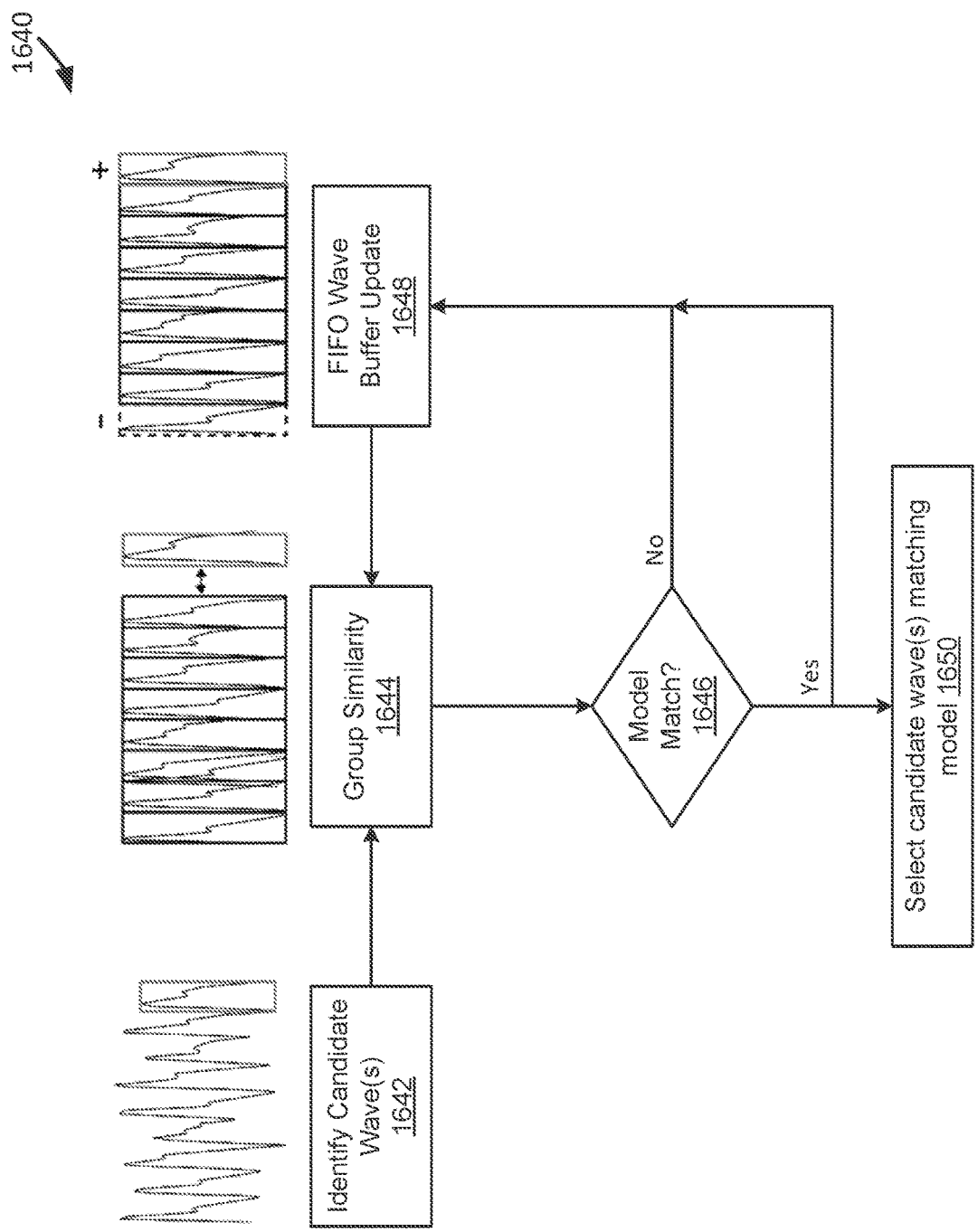
FIG. 16C depicts a flowchart of an example method of method for extracting high quality waves using a group similarity model according to some embodiments.

In step 1610, the blood pressure calculation system determines if one or more of the candidate waves satisfy a model match criterion (e.g., a Gaussian mixture model or a group similarity model). An example method using a Gaussian mixture model is depicted in FIG. 16B, and an example method using a group similarity model is depicted in FIG. 16C. In some embodiments, the wave selection module performs the determination.

In step 1612, the blood pressure calculation system selects the waves satisfying the model match criterion. The selected waves may be grouped into subsets of "high quality" waves. In some embodiments, the selected waves may be stored in a training dataset with the associated channel number. In some embodiments, the wave selection module performs the selection and/or storage.

FIG. 16B depicts a flowchart 1620 of an example method for extracting high quality waves using a Gaussian mixture model according to some embodiments. For example, some or all of the following steps may be applied to a segment of each channel of a multi-channel signal to identify subsets of waves of the multi-channel signal.

In step 1622, the blood pressure calculation system (e.g., blood pressure calculation system 1206) identifies one or more candidate waves. For example, the one or more candidate waves may be identified using steps 1602-1606. In some embodiments, a wave selection module performs the identification.

Figure 27:
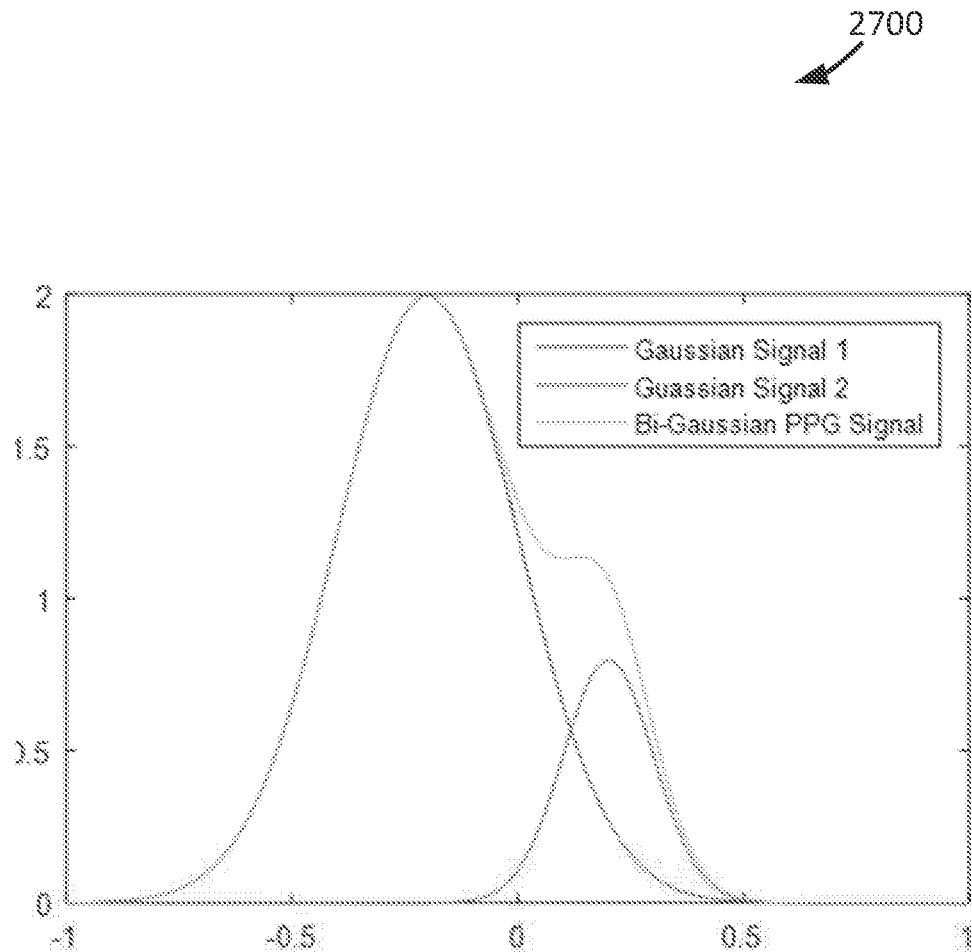
FIG. 27 depicts an example bi-Gaussian mixture model for a PPG signal according to some embodiments.

In step 1624, the blood pressure calculation system determines whether a candidate wave after normalization (e.g., 0-1), satisfies a bi-Gaussian mixture model and the model mismatch error is within a predetermined (e.g., user-defined) threshold value (e.g., 2%). In some embodiments, the wave selection module performs the determination. FIG. 27 depicts an example bi-Gaussian mixture model 2700 for a PPG signal.

In step 1626, the blood pressure calculation system determines whether the fitted model has a reflection coefficient between minimum and maximum possible values (e.g., 0.3-0.7), where the reflection coefficient is defined as the ratio of the diastolic peak to the systolic peak values. In some embodiments, the wave selection module performs the determination.

In step 1628, the blood pressure calculation system selects the candidate waves satisfying the conditions of steps 1622-1626. The selected candidate waves may comprise high quality waves. The high quality waves may be stored in a wave database. In some embodiments, the wave selection module performs the selection and/or storage.

FIG. 16C depicts a flowchart 1640 of an example method of method for extracting high quality waves using a group similarity model according to some embodiments. For example, some or all of the following steps may be applied to a segment of each channel of a multi-channel signal to identify subsets of waves of the multi-channel signal.

In step 1642, the blood pressure calculation system identifies one or more candidate waves. For example, the one or more candidate waves may be identified using steps 1602-1606. In some embodiments, a wave selection module performs the identification.

In step 1644, the blood pressure calculation system applies a similarity measure to determine if at least one of the one or more candidate waves match one or more other waves (e.g., waves stored in a wave buffer). In some embodiments, the wave selection module applies the similarity measure.

In step 1646, if at least one candidate wave matches the other waves, the blood pressure calculation system selects and identified the at least one candidate wave as high quality (step 1648), and stores the at least one candidate wave with the other waves (step 1650). The candidate waves that do not match may also be stored with the other waves (step 1650). In some embodiments, the wave selection performs the selection, identification, and/or storage.

Figure 17:
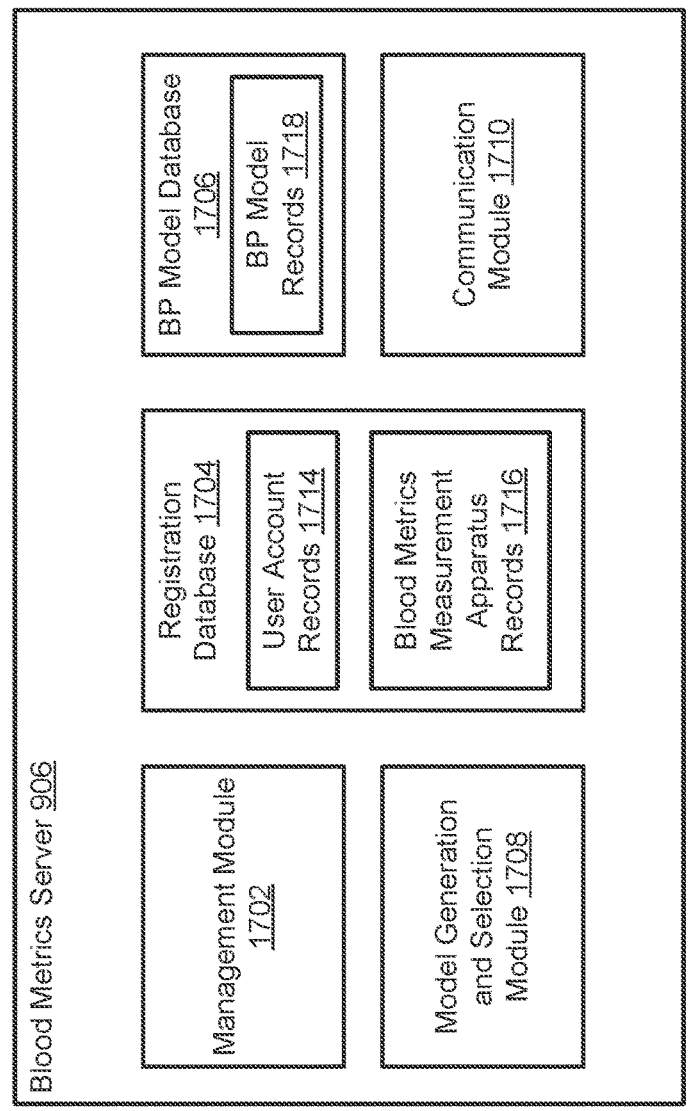
FIG. 17 depicts a block diagram of a blood metrics server according to some embodiments.

FIG. 17 depicts a block diagram 1700 of a blood metrics server 906 according to some embodiments. Generally, the blood metrics server 906 may be configured to generate and/or store empirical blood pressure models, provide empirical blood pressure models to a blood pressure calculation system, register user account and blood metrics measurement apparatus', and communicate with other systems of the system and environment 900. In some embodiments, the blood metrics server 906 includes a management module 1702, a registration database 1704, a blood pressure database 1706, a model generation and selection module 1708, and a communication module 1710.

The management module 1702 may be configured to manage (e.g., create, read, update, delete, or access) user account records 1714 and blood metrics measurement apparatus records 1716 stored in the registration database 1704, and blood pressure model records 1718 stored in the blood pressure model database 1706. The management module 1402 may perform these operations manually (e.g., by an administrator interacting with a GUI) and/or automatically (e.g., by one or more of the modules 1708 or 1710). In some embodiments, the management module 1702 comprises a library of executable instructions which are executable by a processor for performing any of the aforementioned management operations. The databases 1704 and 1706 may be any structure and/or structures suitable for storing the records 1714-1718 (e.g., an active database, a relational database, a table, a matrix, an array, a flat file, and the like).

The user account records 1714 may include a variety of information associated with users, user accounts, associated blood metrics measurement apparatus' and/or associated user devices. For example, the user account records 1714 may store some or all of the following information:

User Account Identifier: Identifier that identifies a user account.

Password: Password, or other personal identifier, used to authenticate the user account. For example, it may an alphanumerical password, biometric data (e.g., fingerprint, etc.). In some embodiments, readings or measurements from the blood metrics measurement apparatus 902 may be used to authenticate the user account.

Device Identifier(s): Identifier(s) that identify one or more blood metrics measurement apparatus' associated with the user account and/or user device.

Name: A name of the user.

DOB: A date of birth of the user.

Age: An age of the user.

Gender: Gender of the user (e.g., female, male, transgender, or the like).

Weight: A weight of the user.

Height: A height of the user.

Skin color: A skin color of the user.

Activity Level: An activity level of the user (e.g., sedentary, lightly active, active, very active, and so forth).

Geographic location: A location of the user (e.g., as determined by a location service and/or specified by the user).

Blood Pressure Profile: Hypertensive, Hypotensive, Normal or unknown.

Blood Glucose Profile (e.g., Diabetes information)

Wrist circumference: Circumference of the user's wrist.

The blood metrics measurement apparatus registration records 1716 may include a variety of information associated with users, user accounts, associated blood metrics measurement apparatus' and/or associated user devices. For example, the blood metrics measurement apparatus registration records 1716 may store some or all of the following information:

Apparatus Identifier: Identifier that identifies a blood metrics measurement apparatus.

User Account Identifier: Identifier that identifies a user account and/or user device associated with the blood metrics measurement apparatus.

Geographic location: A current location of the blood metrics measurement apparatus (e.g., as determined by a location service and/or specified by the user).

Settings: One or more settings of the blood measurement metrics apparatus. For example, some or all of the settings may be automatically determined based on one or more user account attributes (e.g., height, weight, etc.) and/or by the user.

The blood pressure model database 1706 may include one or more empirical blood pressure model records 1718. The models may include various types of empirical blood pressure models. For example, a first type may be a non-specific model which does not require calibration in order to be used to calculate arterial blood pressure values. A second type may be a specific model which requires calibration in order to be used to calculate arterial blood pressure values. For example, models of the second type may require information about the user, such age, weight, height, gender, skin color, and/or the like. In some embodiments, the blood pressure records 1718 may store some or all of the following information:

Model Identifier: Identifies an empirical blood pressure model.

Model Type: Identifies a type of model (e.g., non-specific or specific).

Model Parameters: Various model parameters (e.g., decision node parameters) and tree structures used to calculate the arterial blood pressure values based on the sets of feature vectors and/or other related information (e.g., gender, age, weight, height, skin color, etc.). Example tree structures are shown in FIG. 26.

Apparatus Identifier(s): Identifier(s) that identify one or more blood metrics measurement apparatus' using the empirical blood pressure model.

User Account Identifier(s): Identifier(s) that identify one or more user account(s) associated with the blood metrics measurement apparatus that use the empirical blood pressure model.

The model generation and selection module 1708 may be configured to generate empirical blood pressure models and/or identify an empirical blood pressure models stored in the records 1718 to provide to a blood pressure calculation system. For example, an empirical blood pressure model may be identified in response to a request from a user device or a blood pressure calculation system. In various embodiments, the model generation and selection module 1708 identifies a non-specific empirical blood pressure model which does not require further calibration prior to being used by a blood pressure calculation system to calculate arterial blood pressure values. In some embodiments, the model generation and selection module 1708 includes some or all of the functionality of a wave selection module, feature extraction module, blood pressure processing module, along with associated features and/or functionality (e.g., a signal database, wave database, and so forth).

In one example, an empirical blood pressure model may be identified from a set of models (e.g., stored in the records 1718) by the model generation and selection module 1708 based upon a modified Random Forests algorithm using random decision trees in a regression mode. For example, decision trees may comprise a plurality of nodes for decision making. Two examples of decision trees are shown in FIG. 26. Each internal node may correspond to one comparison point of the input values (e.g., one feature ($F_i$, i=1, ..., N) a feature vector) and edges may represent the path of the outcomes. Leaves (the end points) may represent desired target points. In this example, target points are equivalent to particular blood pressure values.

In some embodiments, a specified (or, predetermined) number of decision trees are constructed. Each decision tree may result in a blood pressure target, but majority voting may give a single blood pressure estimate (or, calculation). In a model training (or, "calibration") phase, the decision node parameters ($a_1, \ldots, a_N, b_1, \ldots, b_N, \ldots$), combination of features, and the structure of the decision trees may be learned, for example, by randomly subsampling the training data and the features, and tracking the error in an unobserved part of the training data. In some embodiments, these parameters and tree structures may comprise the empirical blood pressure models generated and/or stored the blood metrics server 906, and/or used by the blood pressure calculation system 1206 to calculate arterial blood pressure values.

In some embodiments, grown decision trees may learn highly complex patterns. However, they may be prone to overfitting (e.g., sensitive to noise). The model generation and selection module 1708 may address this problem. For example, a tree bagging (or, bootstrap aggregating) technique, in which samples are randomly selected with replacement or without replacement from a training list. The assignment of unseen samples may be performed by taking a majority vote. Although one decision tree may be sensitive to noise, using multiple decision trees and averaging results may significantly decrease the variance as long as the trees are not correlated. In some embodiments, the model generation and selection module 1708 combines tree bagging with feature bagging where the subset of features are also selected randomly with replacement. In some embodiments, the model generation and selection module 1708 may randomly subsample the training dataset without replacement. In some embodiments, the model generation and selection module 1708 may include several parameters to be tuned for a minimum number of leaves and/or number of trees.

In some embodiments, during a model calibration phase, the datasets coming from different subjects may be randomly partitioned to training sets and test sets. In some embodiments, generally, 70-80% of the datasets may be used in training, and the datasets of the same subject may not be both training and testing sets, i.e., test sets and training sets should be disjointed. If the size of the data (number of patients or users) is limited (e.g., ≤150), a bucketwise randomization may be applied (e.g., to help sure that there is enough training data for certain ranges of blood pressure). For example, the bucket edges may be selected as 80, 100, 130, 160, 180, 230. Then, for example, random partitioning may be separately applied to data sets within a certain bucket so that the ratio of training and test samples will be the same.

In some embodiments, the parameters of the tree bagging technique are optimized using k-fold cross validation. Generally, in k-fold cross validation, the existing dataset may be randomly partitioned into training and testing k-times (e.g., k≥1). This may be done, for example, to decrease the bias of the results to the selected test and training sets. Error metrics between the ground truth and estimated blood pressure values in test dataset are averaged k-times. Those metrics may include, and are not limited to, mean square error (MSE, Example Equation 1, shown below), root mean square error (RMSE, Example Equation 2, shown below), median absolute deviation (MAD, Example Equation 3, shown below), and/or coefficient of determination ($R^2$, Example Equation 4, shown below). In some embodiments, the model giving optimal (or, the lowest) error values may be selected and used by the blood pressure calculation system 1206 to calculate arterial blood pressure values.

$$MSE(\hat{y}) = \frac{1}{N}\sum_{i=1}^{N}(y_i - \hat{y}_i)^2 \quad \text{Example Equation 1}$$

$$RMSE(\hat{y}) = \sqrt{\frac{1}{N}\sum_{i=1}^{N}(y_i - \hat{y}_i)^2} \quad \text{Example Equation 2}$$

$$MAD(\hat{y}) = \text{median}(|y - \hat{y}|) \quad \text{Example Equation 3}$$

$$R^2(\hat{y}) = 1 - \frac{MSE(\hat{y})}{\text{var}(y)} \quad \text{Example Equation 4}$$

In some embodiments, the model generation and selection module 1708 minimizes overfitting. For example, each fold (or, k-fold) may be individually trained. Feature sets may be identified for each fold through backward or floating search optimizations where features are added or removed (e.g., to improve cost). In some embodiments, in order to enable cross-validation (CV) or bootstrapping (BS) performance match an unseen test set accurately, a measure of test-train cost may be calculated. This may be performed, for example, to inform feature selection approaches for adding or removal of features. For example, Test-Train cost may be defined as $$C_{TT} = 1 - \frac{RMSE_{Train}}{RMSE_{Test}},$$

where $C_{TT}$ may be close to "0" if test error and train error tracked each other closely, and may be "1" if train error was smaller than test (e.g., overfitting). This may be applied, for example, when a new feature is added (e.g., not present in the current optimal feature set), or when an existing featured is removed (e.g., from the current optimal feature set). In some embodiments, the corresponding condition which must be met to continue adding or removing a feature may be calculated as current cost <(previous cost+$\alpha F\ C_{TT}$), where $\alpha$ is the weight associated with the Test-Train cost, and F is "1" for testing feature removal and "−1" for testing feature addition. While this may have the effect of reducing model complexity while increasing RMSE, model complexity is not directly minimized, which could have the desired effect of allowing model complexity to be relatively large without penalty as long as $C_{TT}$ is relatively small.

In some embodiments, the communication module 1710 may be configured to send requests to and receive data from one or a plurality of systems. The communication module 1710 may send requests to and receive data from a systems through a network or a portion of a network. Depending upon implementation-specific or other considerations, the communication module 1710 may send requests and receive data through a connection (e.g., the communication network 908, and/or the communication link 910), all or a portion of which may be a wireless connection. The communication module 1710 may request and receive messages, and/or other communications from associated systems.

Figure 18:
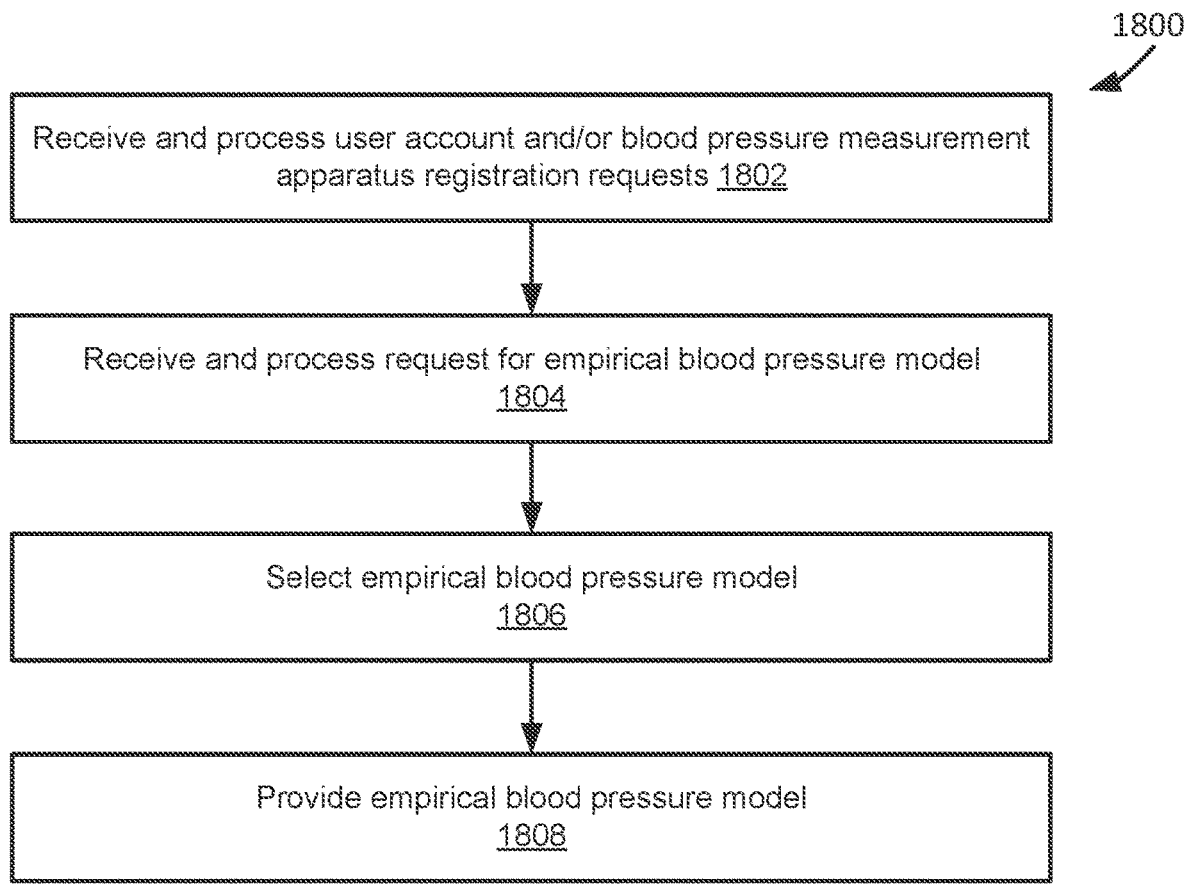
FIGS. 18-20 depict flowcharts of example methods of operation of a blood metrics server according to some embodiments.

FIG. 18 depicts a flowchart 1800 of an example method of operation of a blood metrics server (e.g., blood metrics server 906) according to some embodiments.

Figure 20:
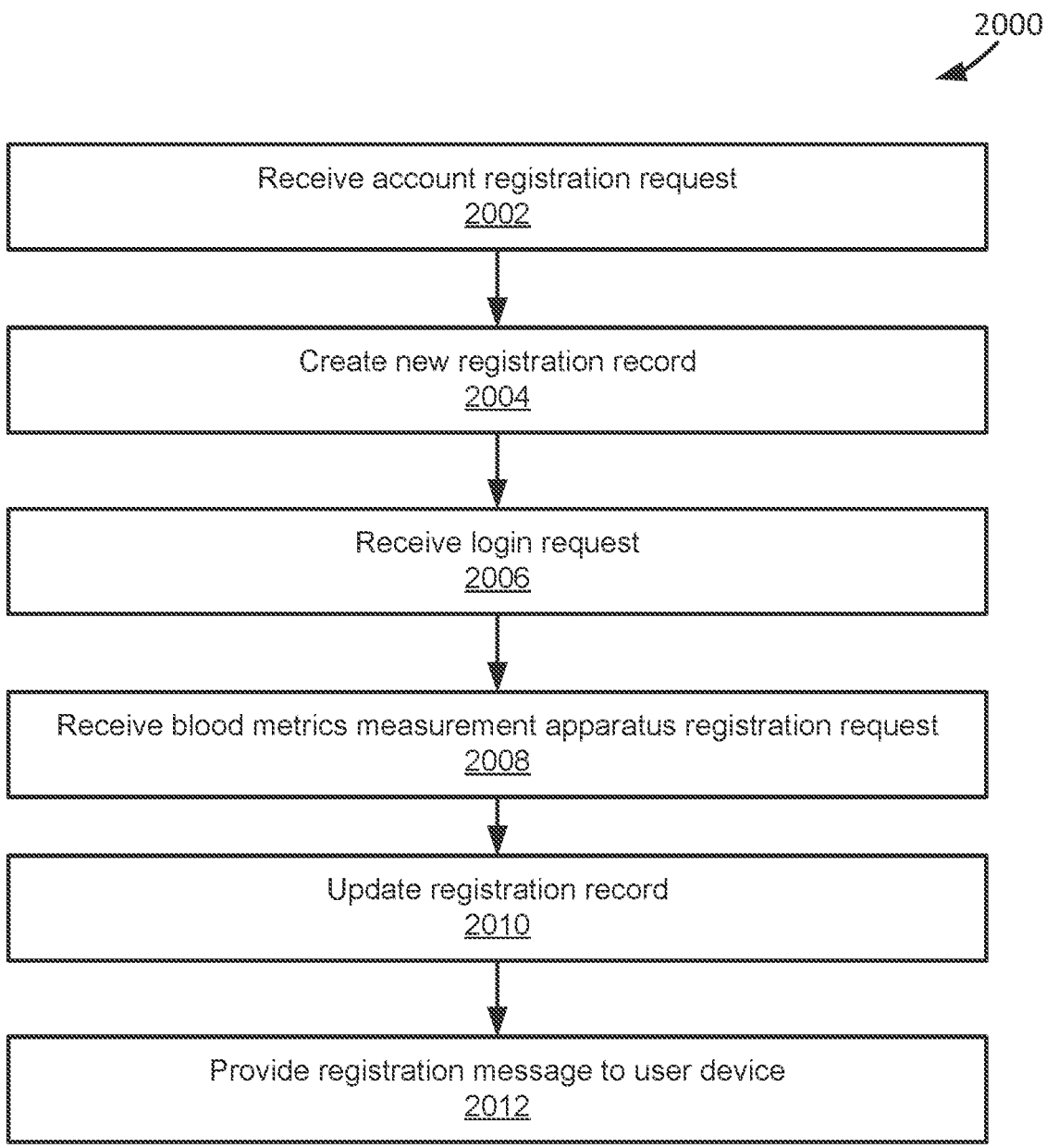

In step 1802, the blood metrics server receives and processes user account and/or blood pressure measurement apparatus registration requests. In some embodiments a communication module (e.g., communication module 1712) receives the requests. An example registration method is shown in FIG. 20.

In step 1804, the blood metrics server receives and processes a request for an empirical blood pressure model. In some embodiments, the communication module receives the request from a user device (e.g., user device 904) and/or blood pressure calculation system (e.g., blood pressure calculation system 1206). For example, the user device and/or blood pressure calculation system may periodically request an updated model.

In step 1806, the blood metrics server selects an empirical blood pressure model. For example, the model may be selected in response to the request, although in some embodiments, the blood metrics server may automatically select a model in order to push down an updated model to the user device. In some embodiments, a model generation and selection module (e.g., model selection 1708) performs the selection.

In step 1808, the blood metrics server provides the selected empirical blood pressure to the user device and/or blood pressure calculation system. In some embodiments, the communication module provides the selected empirical blood pressure model.

Figure 19:
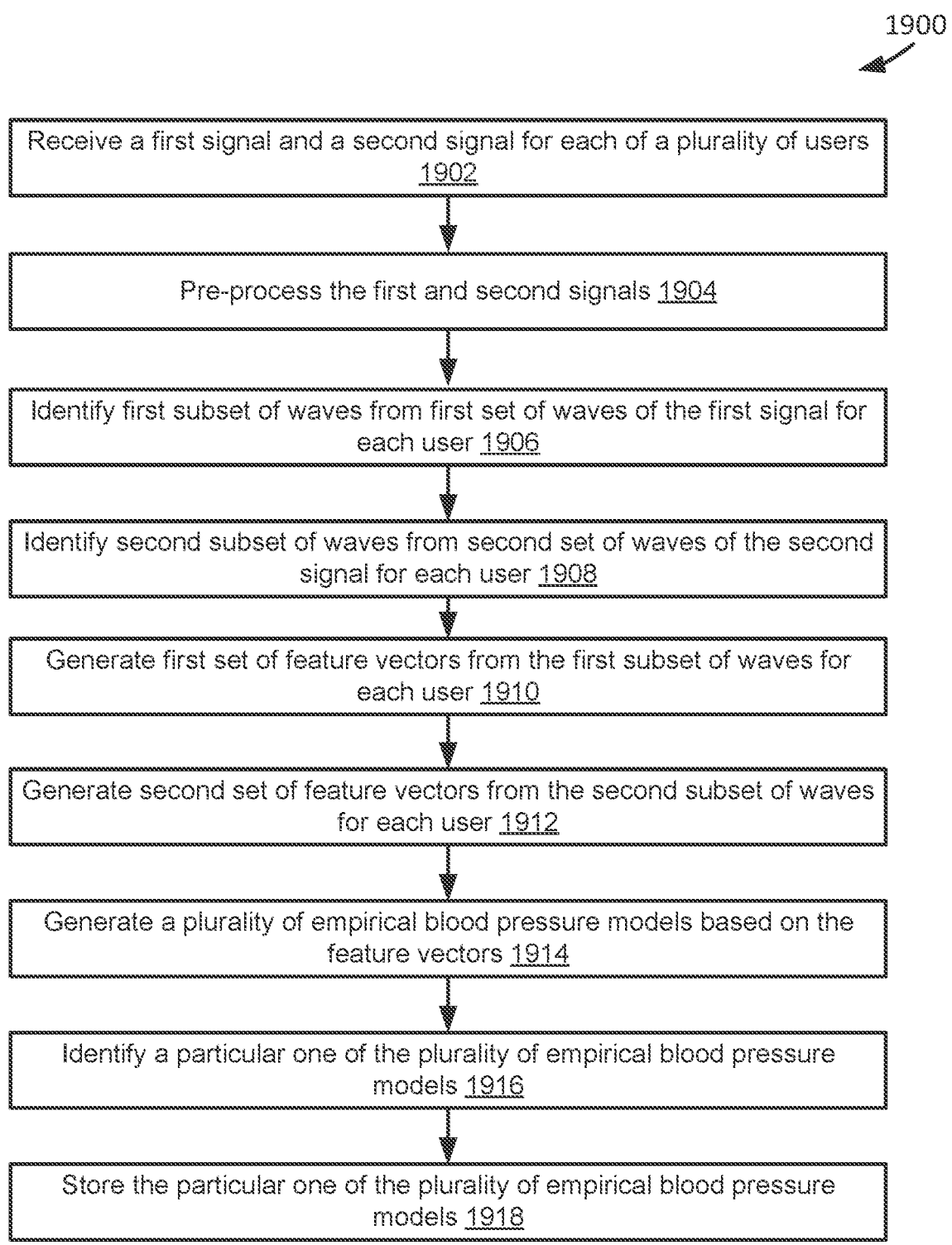

FIG. 19 depicts a flowchart 1900 of an example method of operation of a blood metrics server (e.g., blood metrics server 906) according to some embodiments.

In step 1902, the blood metrics server receives a first signal (e.g., a single-channel or multi-channel PPG signal) and a second signal (e.g., a single-channel or multi-channel PPG signal) for each of a plurality of users (e.g., training subjects). For example, the first signal may comprise a 7-channel PPG signal generated from light energy emitted at seven different wavelengths (e.g., 523 nm, 590 nm, 623 nm, 660 nm, 740 nm, 850 nm, 940 nm) from one or more light sources (e.g., seven different LEDs), and the second signal may comprise a single-channel PPG signal generated from light energy generated from an additional light source (e.g., LED) at the same, or substantially similar, wavelength as one the wavelengths of the first signal. Using multi-channel signals and/or different light sources may help ensure, for example, that good quality signals may be obtained in a variety of circumstances (a user moving, walking, running, sleeping, and so forth). In some embodiments, a communication module (e.g., communication module 1712) receives the first and second signals from a blood metrics measurement apparatus (e.g., blood metrics measurement apparatus 902) and/or other blood pressure measurement devices, such as other types of non-invasive devices (e.g., sphygmomanometer) and/or invasive devices (e.g., catheters, tubes, etc.).

In step 1904, the blood metrics server pre-processes (or filters) the first and second signals. In some embodiments, a pre-processing module filters the first and second signals.

In step 1906-1908, the blood metrics server identifies, for each of the plurality of users, a first subset of waves (or, "high quality" waves) from a first set of waves of the first signal and a second subset of waves (or, "high quality" waves) from a second set of waves of the second signal, each of the first subset of waves representing a separate approximation of an average of the first set of waves over a predetermined amount of time and each of the second subset of waves representing a separate approximation of an average of the second set of waves over the predetermined amount of time. In some embodiments, a model generation and selection module (e.g., model generation and selection module 1708) identifies the subsets of waves.

In step 19010-1912, the blood metrics server generates, for each of the plurality of users, a first set of feature vectors and a second set of feature vectors. The first set of feature vectors may be generated from the first subset of waves, and the second set of feature vectors may be generated from the second subset of waves. Each of the feature vectors may include measurement values and metric values. For example, the measurement values may correspond to amplitude (e.g., peak-to-peak amplitude, peak amplitude, semi-amplitude, root mean square amplitude, pulse amplitude, etc.) or location points of a particular wave (e.g., a corresponding high quality wave), and the metric values may be generated from metric functions that use at least one of the measurement values. In some embodiments, the model generation and selection module generates the sets of feature vectors.

In step 1914, the blood metrics server generates a plurality of empirical blood pressure models based on the feature vectors. In some embodiments, the model generation and selection module generates the models.

In step 1916, the blood metrics server identifies a particular one of the plurality of empirical blood pressure models. The identified model may be used to calculate arterial blood pressure values without requiring further calibration (e.g., a non-specific type of empirical blood pressure model). In some embodiments, the model generation and selection module performs the identification.

In step 1918, the blood metrics server stores the particular one of the plurality of empirical blood pressure models. In some embodiments, a management module (e.g., management module 1702) stores the particular model in a database (e.g., blood pressure model database 1706).

FIG. 20 depicts a flowchart 2000 of an example method of operation of a blood metrics server (e.g., blood metrics server 906) according to some embodiments.

In step 2002, the blood metrics server receives a user account registration request from a user device (e.g., user device 904) via a communication network (e.g., communication network 908). The user account registration request may include, for example, a username (e.g., "jsmith2015), password, full name (e.g., "John Smith"), birthdate, gender, physical characteristics (e.g., height, weight, etc.), and so forth. In some embodiments a communication module (e.g., communication module 1716) receives the user account registration request.

In step 2004, if the blood metrics server approves the registration request, the blood metrics server may create a new user account registration record (e.g., user account registration record 1714) in a registration database (e.g., registration database 1704) and/or an account for the user. In some embodiments, a management module (e.g., management module 1702) creates the user account registration record.

In step 2006, the blood metrics server receives a log-in request from the user device. The log-in request may include, for example, the username and password. If the log-in credentials are correct, the blood metrics server logs the user account into the user device. In some embodiments the communication module receives the log-in request.

In step 2008, the blood metrics server receives a blood metrics measurement apparatus registration request from the user device. The blood metrics measurement apparatus registration request may include, for example, an apparatus identifier that identifies the blood metrics measurement apparatus, and a user account identifier associated the user account and/or user device. The apparatus identifier may be obtained by the user device by a variety of methods such as scanning a physical feature (e.g., a tag, code, or the like) of the blood metrics measurement apparatus, entering the identifier manually via the user device, and/or the like. In some embodiments the communication module receives the blood metrics measurement apparatus registration request.

In step 2010, the blood metrics server updates the registration database with the blood metrics measurement apparatus registration request by either creating a new record (e.g., a record 1716) or, if the apparatus identifier is already stored in one of the records (e.g., records 1716), updating that particular record. In some embodiments, the management module updates the registration database.

In step 2012, the blood metrics server provides a registration success message to the user device when the registration database has been updated. In some embodiments the communication module provides the message.

FIG. 21 depicts an example noisy PPG signal 2100 and an example filtered PPG signal 2150 according to some embodiments.

FIG. 22 depicts an example set of waves 2200 of a PPG signal and an example high quality wave 2202 selected from the set of waves 2200 according to some embodiments. FIG. 22 further depicts an example bi-Gaussian fitted signal 2204 according to some embodiments.

FIG. 23 depicts example feature points 2302a-u of a wave 2300 according to some embodiments. For example, the feature points 2302a-u may comprise location points and/or amplitudes. In some embodiments, some or all of the features points 2302a-u may correspond to measurement values which may be used by one or more metric functions.

FIGS. 25A-C show an example selected high quality wave 2500, the first derivative 2502 of the selected high quality wave 2500, and the second derivative 2504 of the selected high quality wave 2500 according to some embodiments.

FIG. 26 depicts example tree structures 2602 and 2604 of an example empirical blood pressure calculation model 2600 according to some embodiments.

It will be appreciated that a "user device," "apparatus," "server," "module," "system," and/or "database" may comprise software, hardware, firmware, and/or circuitry. In one example, one or more software programs comprising instructions capable of being executable by a processor may perform one or more of the functions of the user devices, servers, modules, systems, and/or databases described herein. In another example, circuitry may perform the same or similar functions. Alternative embodiments may comprise more, less, or functionally equivalent user devices, apparatus, servers, modules, systems, and/or databases, and still be within the scope of present embodiments. For example, the blood metrics measurement apparatus 902 may include some or all of the functionality of the user device 904 (e.g., user interface module 1202, blood pressure calculation system 1206, etc.), the blood metrics server 906 may include some or all of the functionality of the blood pressure calculation system 1206, and so forth.

The present invention(s) are described above with reference to example embodiments. It will be appreciated that various modifications may be made and other embodiments may be used without departing from the broader scope of the present invention(s). Therefore, these and other variations upon the example embodiments are intended to be covered by the present invention(s).

The invention claimed is:

1. A wearable non-invasive blood pressure measurement system with motion artifact removal, comprising:
   a wearable medical device comprising
      an accelerometer configured to generate accelerometer signals indicative of motion,
      an energy receiver configured to receive light reflected from tissue of a patient, and
      a processor operatively coupled to the energy receiver and configured to generate one or more noise-corrupted optical signals associated with arterial blood pressure of the patient based on the received light, and
   a blood pressure calculation system in communication with the wearable medical device, wherein the blood pressure calculation system comprises
      a filtering system comprising an adaptive filter configured to apply the accelerometer signals indicative of motion as a noise reference, and
   wherein the blood pressure calculation system is configured to
      receive the one or more noise-corrupted optical signals,
      filter, using the filtering system, the one or more noise-corrupted optical signals based on the adaptive filter, to provide non-corrupted optical signals,
      select a subset of waves of the non-corrupted optical signals over a predetermined amount of time,
      obtain feature vectors from the subset of waves associated with the arterial blood pressure of the patient, and
      input the obtained feature vectors into an empirical blood pressure calculation model to calculate one or more arterial blood pressure values.

2. The blood pressure measurement system of claim 1, wherein the accelerometer is configured to capture components of the accelerometer signals indicative of motion along three axes.

3. The blood pressure measurement system of claim 2, wherein the blood pressure calculation system is configured to calculate a sum of the components and use the sum as the noise reference.

4. The blood pressure measurement system of claim 2, wherein the blood pressure calculation system is configured to select a largest one of the components for use as the noise reference.

5. The blood pressure measurement system of claim 1, wherein the subset of waves is selected using a group similarity model.

6. The blood pressure measurement system of claim 5, wherein the subset of waves includes candidate waves configured to be individually matched to a wave buffer according to the group similarity model.

7. The blood pressure measurement system of claim 6, wherein the wave buffer includes at least some of the candidate waves added in succession in a first in, first out (FIFO) method.

8. The blood pressure measurement system of claim 6, wherein the wave buffer includes a predetermined number of waves.

9. The blood pressure measurement system of claim 8, wherein the group similarity model is configured to apply a similarity measure to determine if a particular one of the candidate waves matches a plurality of the waves in the wave buffer.

10. The blood pressure measurement system of claim 9, wherein the particular one of the candidate waves is selected for further processing if the similarity measure exceeds a predetermined threshold.

11. The blood pressure measurement system of claim 1, wherein the wearable medical device further comprises an energy transmitter configured to project light at a predetermined at least one wavelength into the tissue of the patient.

12. The blood pressure measurement system of claim 11, wherein the energy transmitter includes a first light source and a second light source, the first light source configured to project the light at a first wavelength, and the second light source configured to project the light at a second wavelength, into the tissue of the patient.

13. The blood pressure measurement system of claim 12, wherein the first light source and the second light source are spaced at a predetermined distance from each other, and the first and second light sources are associated with corresponding photodiodes of the energy receiver.

14. The blood pressure measurement system of claim 12, wherein the light projected by the first and second light sources have the same wavelength.

15. The blood pressure measurement system of claim 11, wherein the energy receiver is configured to receive the light transmitted through the tissue of the patient.

16. The blood pressure measurement system of claim 1, wherein the feature vectors are extracted from the subset of waves, and include measurement values and metric values.

17. The blood pressure measurement system of claim 16, wherein the measurement values correspond to amplitude or location points of a particular wave of the subset of waves.

18. The blood pressure measurement system of claim 17, wherein the metric values are generated from metric functions that use at least one of the measurement values.

19. The blood pressure measurement system of claim 1, wherein the wearable medical device is a wrist-worn device.

20. The blood pressure measurement system of claim 19, wherein the wrist-worn device comprises a central unit, a sensory array coupled to the central unit and comprising at least an energy transmitter and the energy receiver, and a display mounted on the central unit.

21. The blood pressure measurement system of claim 19, wherein the blood pressure calculation system is configured to provide a message via a display of the wrist-worn device including or being based on the one or more arterial blood pressure values.

22. A non-transitory computer readable medium storing executable computer program instructions, the computer program instructions comprising instructions that when executed cause a computer processor to:

receive one or more noise-corrupted optical signals from a wearable medical device, the one or more noise-corrupted optical signals being generated based on light reflected by tissue of a patient and associated with arterial blood pressure of the patient;

filter, by a filtering system, the one or more noise-corrupted optical signals to provide non-corrupted optical signals, wherein the filtering system comprises an adaptive filter configured to receive accelerometer signals indicative of motion from an accelerometer of the wearable medical device and apply the signals indicative of motion as a noise reference;

select a subset of waves of the non-corrupted optical signals over a predetermined amount of time;

obtain feature vectors from the subset of waves associated with the arterial blood pressure of the patient; and input the obtained feature vectors into an empirical blood pressure calculation model to calculate one or more arterial blood pressure values.

23. The non-transitory computer readable medium of claim 22, wherein the computer program instructions are configured to be executed on a digital device.

24. The non-transitory computer readable medium of claim 23, wherein the digital device is a mobile device that includes an application interface configured to execute the computer program instructions.

25. The non-transitory computer readable medium of claim 23, wherein the digital device is operably connected to the wearable medical device.

26. The non-transitory computer readable medium of claim 25, wherein the digital device is configured to receive one or more blood metric measurements from the wearable medical device and perform analysis of the one or more blood metric measurements.

27. The non-transitory computer readable medium of claim 22, wherein the accelerometer is configured to capture components of the accelerometer signals indicative of motion along three axes.

28. The non-transitory computer readable medium of claim 27, wherein the computer program instructions are configured to calculate a sum of the components and use the sum as the noise reference.

29. The non-transitory computer readable medium of claim 27, wherein the computer program instructions are configured to select a largest one of the components for use as the noise reference.

30. The non-transitory computer readable medium of claim 22, wherein the subset of waves is selected using a group similarity model.

31. The non-transitory computer readable medium of claim 30, wherein the subset of waves includes candidate waves configured to be individually matched to a wave buffer according to the group similarity model.

32. The non-transitory computer readable medium of claim 31, wherein the wave buffer includes at least some of the candidate waves added in succession in a first in, first out (FIFO) method.

33. The non-transitory computer readable medium of claim 31, wherein the wave buffer includes a predetermined number of waves.

34. The non-transitory computer readable medium of claim 33, wherein the group similarity model is configured to apply a similarity measure to determine if a particular one of the candidate waves matches some or all of the waves in the wave buffer.

35. The non-transitory computer readable medium of claim 34, wherein the particular one of the candidate waves is selected for further processing if the similarity measure exceeds a predetermined threshold.

36. The non-transitory computer readable medium of claim 22, wherein the feature vectors are extracted from the subset of waves, and include measurement values and metric values.

37. The non-transitory computer readable medium of claim 36, wherein the measurement values correspond to amplitude or location points of a particular wave of the subset of waves.

38. The non-transitory computer readable medium of claim 37, wherein the metric values are generated from metric functions that use at least one of the measurement values.

* * * * *

UNITED STATES PATENT AND TRADEMARK OFFICE
CERTIFICATE OF CORRECTION

PATENT NO. : 11,963,799 B2
APPLICATION NO. : 18/151576
DATED : April 23, 2024
INVENTOR(S) : Elad Ferber et al.

It is certified that error appears in the above-identified patent and that said Letters Patent is hereby corrected as shown below:

In the Drawings

Sheet 30, FIG. 27, delete "Guassian" and insert -- Gaussian --

In the Specification

Column 1, Line 23, delete "RAIL" and insert -- RATE --

Column 5, Line 30, delete "the the" and insert -- the --

Column 15, Line 31, delete "filer" and insert -- filter --

Column 16, Lines 10-11, delete "peturbation," and insert -- perturbation, --

Column 17, TABLE 3, Line 6, under header "symbol" delete "$I_{HR}^{Harmonic}$" and insert -- $I_{Harmonic}^{HR}$ --

Column 17, TABLE 3, Lines 17-18, delete "nonlincarity" and insert -- nonlinearity --

Column 19, TABLE 3-continued, Line 32, delete "X=" and insert -- $\lambda$ = --

Column 31, Line 33, delete "filer" and insert -- filter --

Columns 33, TABLE 3, Line 6, delete "$I_{HR}$" and insert -- $I_{Harmonic}^{HR}$ --

Columns 33, TABLE 3, Lines 17-18, delete "nonlincarity" and insert -- nonlinearity --

Column 33, Table 3, Line 21, under header "Equation" delete "$\alpha_r$," and insert -- $\alpha_r$ --

Column 34, TABLE 2-continued, Line 8, below "Frequency" delete "Parameter  $|v|_{GPS}$"

Signed and Sealed this
Eighteenth Day of February, 2025

Coke Morgan Stewart
*Acting Director of the United States Patent and Trademark Office*

Column 34, TABLE 2-continued, Lines 9-12, delete

"
| GPS velocity | $\|alt\|_{GPS}$ |
| GPS altitude | $\|\alpha\|_{GPS}$ |
| GPS acceleration | $\|incline\|_{GPS}$ |
| GPS incline | pH |

" and insert

| GPS velocity | $\|v\|_{GPS}$ |
| GPS altitude | $\|alt\|_{GPS}$ |
| GPS acceleration | $\|a\|_{GPS}$ |
| GPS incline | $\|incline\|_{GPS}$ |

--

Column 35, Line 38, delete "X=" and insert -- λ= --

Column 37, Line 5, delete

"$$\frac{\epsilon_{Hb}^{CO_2} - \epsilon_{Hb}^{Hb} * I_{\lambda_{CO_2}}^{AC} * I_{\lambda_1}^{DC}/(I_{\lambda_1}^{AC} * I_{\lambda_{CO_2}}^{DC})}{\epsilon_{Hb}^{CO_2} - \epsilon_{CO_2}^{CO_2} + (\epsilon_{CO_2}^{Hb} - \epsilon_{Hb}^{Hb}) * I_{\lambda_{CO_2}}^{AC} * I_{\lambda_1}^{DC}/(I_{\lambda_1}^{AC} * I_{\lambda_{CO_2}}^{DC})}$$" and insert $$\frac{\epsilon_{Hb}^{O_2} - \epsilon_{Hb}^{Hb} * I_{\lambda_{O_2}}^{AC} * I_{\lambda_1}^{DC}/(I_{\lambda_1}^{AC} * I_{\lambda_{O_2}}^{DC})}{\epsilon_{Hb}^{O_2} - \epsilon_{O_2}^{O_2} + (\epsilon_{O_2}^{Hb} - \epsilon_{Hb}^{Hb}) * I_{\lambda_{O_2}}^{AC} * I_{\lambda_1}^{DC}/(I_{\lambda_1}^{AC} * I_{\lambda_{O_2}}^{DC})}$$

--

Column 37, Line 62, delete "FIG." and insert -- FIGS. --

Column 38, Line 66, delete "information)" and insert -- information). --

Column 50, Line 57, delete "Savitzksy-" and insert -- Savitzky- --

Column 54, Line 13, delete "information)" and insert -- information). --